United States Patent
Wang

(12) 
(10) Patent No.: US 6,346,607 B1
(45) Date of Patent: Feb. 12, 2002

(54) APAF-1 AN ACTIVATOR OF CASPASE-3

(75) Inventor: Xiaodong Wang, Dallas, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 09/435,115

(22) Filed: Nov. 5, 1999

Related U.S. Application Data

(62) Division of application No. 09/092,508, filed on Jun. 5, 1998.
(60) Provisional application No. 60/055,258, filed on Aug. 7, 1997, and provisional application No. 60/048,807, filed on Jun. 5, 1997.

(51) Int. Cl.[7] ............ C07K 14/00; C08H 1/00; C12N 9/00; C12Q 1/00
(52) U.S. Cl. ............ 530/350; 530/409; 435/183; 435/4
(58) Field of Search ................ 530/350, 409; 435/183, 4

(56) References Cited

FOREIGN PATENT DOCUMENTS

WO    WO 93 25685    12/1993

OTHER PUBLICATIONS

Hillier L. et al., Apr. 18, 1996, *EMEST7 database*, (Rel. 47, Created) "Accession No. N92067".

Spector MS et al., Feb. 13, 1997, *Nature* 385 (6617) p653–6, "Interaction between the C. elegans cell–death regulators CED–9 and CED–4,".

Zou H. et al., Aug. 8, 1997, *Cell* 90 (3) p405–13, "Apaf–1, a human protein homologous to C. elegans CED–4, participates in cytochrome c–dependent activation of caspase–3".

*Primary Examiner*—Ponnathapu Achutamurthy
*Assistant Examiner*—Peter P. Tung
(74) *Attorney, Agent, or Firm*—Richard Aron Osman

(57) ABSTRACT

Novel polypeptides, designated Apaf-1, which are capable of modulating apoptosis are provided. Compositions including Apaf-1 chimeras, nucleic acid encoding Apaf-1, and antibodies to Apaf-1 are also provided.

12 Claims, 31 Drawing Sheets

FIG. 4

Fractions | 10 | 11 | 12 | 13 | 14 | 15 | 16 | 17 | 18 |

KDa
200 —
116 —           ← Apaf - 1
80 —
66 —

```
AAGAAGAGGT AGCGAGTGGA CGTGACTGCT CTATCCCGGG CAAAAGGGAT AGAACCAGAG    60
GTGGGGAGTC TGGGCAGTCG GCGACCCGCG AAGACTTGAG GTGCCGCAGC GGCATCCGGA   120
GTAGCGCCGG GCTCCCTCCG GGGTGCAGCC GCCGTCGGGG GAAGGGCGCC ACAGGCCGGG   180
AAGACCTCCT CCCTTTGTGT CCAGTAGTGG GGTCCACCGG AGGGCGGCCC GTGGGCCGGG   240
CCTCACCGCG GCGCTCCGGG ACTGTGGGGT CAGGCTGCGT TGGGTGGACG CCCACCTCGC   300
CAACCTTCGG AGGTCCCTGG GGGTCTTCGT GCGCCCCGGG GCTGCAGAGA TCCAGGGGAG   360
GCGCCTGTGA GGCCCGGACC TGCCCCGGGG CGAAGGGTAT GTGGCGAGAC AGAGCCCTGC   420
ACCCCTAATT CCCGGTGGAA AACTCCTGTT GCCGTTTCCC TCCACCGGCC TGGAGTCTCC   480
CAGTCTTGTC CCGGCAGTGC CGCCCTCCCC ACTAAGACCT AGGCGCAAAG GCTTGGCTCA   540
TGGTTGACAG CTCAGAGAGA GAAAGATCTG AGGGAAG ATG GAT GCA AAA GCT CGA   595
                                          Met Asp Ala Lys Ala Arg
                                           1               5

AAT TGT TTG CTT CAA CAT AGA GAA GCT CTG GAA AAG GAC ATC AAG ACA    643
Asn Cys Leu Leu Gln His Arg Glu Ala Leu Glu Lys Asp Ile Lys Thr
            10              15              20

TCC TAC ATC ATG GAT CAC ATG ATT AGT GAT GGA TTT TTA ACA ATA TCA    691
Ser Tyr Ile Met Asp His Met Ile Ser Asp Gly Phe Leu Thr Ile Ser
        25              30              35

GAA GAG GAA AAA GTA AGA AAT GAG CCC ACT CAA CAG CAA AGA GCA GCT    739
Glu Glu Glu Lys Val Arg Asn Glu Pro Thr Gln Gln Gln Arg Ala Ala
    40              45              50

ATG CTG ATT AAA ATG ATA CTT AAA AAA GAT AAT GAT TCC TAC GTA TCA    787
Met Leu Ile Lys Met Ile Leu Lys Lys Asp Asn Asp Ser Tyr Val Ser
55              60              65              70

TTC TAC AAT GCT CTA CTA CAT GAA GGA TAT AAA GAT CTT GCT GCC CTT    835
Phe Tyr Asn Ala Leu Leu His Glu Gly Tyr Lys Asp Leu Ala Ala Leu
        75              80              85

CTC CAT GAT GGC ATT CCT GTT GTC TCT TCT TCC AGT GTA AGG ACA GTC    883
Leu His Asp Gly Ile Pro Val Val Ser Ser Ser Ser Val Arg Thr Val
            90              95             100

CTG TGT GAA GGT GGA GTA CCA CAG AGG CCA GTT GTT TTT GTC ACA AGG    931
Leu Cys Glu Gly Gly Val Pro Gln Arg Pro Val Val Phe Val Thr Arg
        105             110             115

AAG AAG CTG GTG AAT GCA ATT CAG CAG AAG CTC TCC AAA TTG AAA GGT    979
Lys Lys Leu Val Asn Ala Ile Gln Gln Lys Leu Ser Lys Leu Lys Gly
    120             125             130

GAA CCA GGA TGG GTC ACC ATA CAT GGA ATG GCA GGC TGT GGG AAG TCT   1027
Glu Pro Gly Trp Val Thr Ile His Gly Met Ala Gly Cys Gly Lys Ser
135             140             145             150

GTA TTA GCT GCA GAA GCT GTT AGA GAT CAT TCC CTT TTA GAA GGT TGT   1075
Val Leu Ala Ala Glu Ala Val Arg Asp His Ser Leu Leu Glu Gly Cys
        155             160             165

TTC CCA GGG GGA GTG CAT TGG GTT TCA GTT GGG AAA CAA GAC AAA TCT   1123
Phe Pro Gly Gly Val His Trp Val Ser Val Gly Lys Gln Asp Lys Ser
            170             175             180
```

FIG. 5B

```
GGG CTT CTG ATG AAA CTG CAG AAT CTT TGC ACA CGG TTG GAT CAG GAT    1171
Gly Leu Leu Met Lys Leu Gln Asn Leu Cys Thr Arg Leu Asp Gln Asp
        185             190             195

GAG AGT TTT TCC CAG AGG CTT CCA CTT AAT ATT GAA GAG GCT AAA GAC    1219
Glu Ser Phe Ser Gln Arg Leu Pro Leu Asn Ile Glu Glu Ala Lys Asp
    200             205             210

CGT CTC CGC ATT CTG ATG CTT CGC AAA CAC CCA AGG TCT CTC TTG ATC    1267
Arg Leu Arg Ile Leu Met Leu Arg Lys His Pro Arg Ser Leu Leu Ile
215             220             225             230

TTG GAT GAT GTT TGG GAC TCT TGG GTG TTG AAA GCT TTT GAC AGT CAG    1315
Leu Asp Asp Val Trp Asp Ser Trp Val Leu Lys Ala Phe Asp Ser Gln
                235             240             245

TGT CAG ATT CTT CTT ACA ACC AGA GAC AAG AGT GTT ACA GAT TCA GTA    1363
Cys Gln Ile Leu Leu Thr Thr Arg Asp Lys Ser Val Thr Asp Ser Val
        250             255             260

ATG GGT CCT AAA TAT GTA GTC CCT GTG GAG AGT TCC TTA GGA AAG GAA    1411
Met Gly Pro Lys Tyr Val Val Pro Val Glu Ser Ser Leu Gly Lys Glu
        265             270             275

AAA GGA CTT GAA ATT TTA TCC CTT TTT GTT AAT ATG AAG AAG GCA GAT    1459
Lys Gly Leu Glu Ile Leu Ser Leu Phe Val Asn Met Lys Lys Ala Asp
    280             285             290

TTG CCA GAA CAA GCT CAT AGT ATT ATA AAA GAA TGT AAA GGC TCT CCC    1507
Leu Pro Glu Gln Ala His Ser Ile Ile Lys Glu Cys Lys Gly Ser Pro
295             300             305             310

CTT GTA GTA TCT TTA ATT GGT GCA CTT TTA CGT GAT TTT CCC AAT CGC    1555
Leu Val Val Ser Leu Ile Gly Ala Leu Leu Arg Asp Phe Pro Asn Arg
                315             320             325

TGG GAG TAC TAC CTC AAA CAG CTT CAG AAT AAG CAG TTT AAG AGA ATA    1603
Trp Glu Tyr Tyr Leu Lys Gln Leu Gln Asn Lys Gln Phe Lys Arg Ile
        330             335             340

AGG AAA TCT TCG TCT TAT GAT TAT GAG GCT CTA GAT GAA GCC ATG TCT    1651
Arg Lys Ser Ser Ser Tyr Asp Tyr Glu Ala Leu Asp Glu Ala Met Ser
        345             350             355

ATA AGT GTT GAA ATG CTC AGA GAA GAC ATC AAA GAT TAT TAC ACA GAT    1699
Ile Ser Val Glu Met Leu Arg Glu Asp Ile Lys Asp Tyr Tyr Thr Asp
    360             365             370

CTT TCC ATC CTT CAG AAG GAC GTT AAG GTG CCT ACA AAG GTG TTA TGT    1747
Leu Ser Ile Leu Gln Lys Asp Val Lys Val Pro Thr Lys Val Leu Cys
375             380             385             390

ATT CTC TGG GAC ATG GAA ACT GAA GAA GTT GAA GAC ATA CTG CAG GAG    1795
Ile Leu Trp Asp Met Glu Thr Glu Glu Val Glu Asp Ile Leu Gln Glu
                395             400             405

TTT GTA AAT AAG TCT CTT TTA TTC TGT GAT CGG AAT GGA AAG TCG TTT    1843
Phe Val Asn Lys Ser Leu Leu Phe Cys Asp Arg Asn Gly Lys Ser Phe
        410             415             420
```

FIG. 5C

```
CGT TAT TAT TTA CAT GAT CTT CAA GTA GAT TTT CTT ACA GAG AAG AAT    1891
Arg Tyr Tyr Leu His Asp Leu Gln Val Asp Phe Leu Thr Glu Lys Asn
        425                 430                 435

TGC AGC CAG CTT CAG GAT CTA CAT AAG AAG ATA ATC ACT CAG TTT CAG    1939
Cys Ser Gln Leu Gln Asp Leu His Lys Lys Ile Ile Thr Gln Phe Gln
    440                 445                 450

AGA TAT CAC CAG CCG CAT ACT CTT TCA CCA GAT CAG GAA GAC TGT ATG    1987
Arg Tyr His Gln Pro His Thr Leu Ser Pro Asp Gln Glu Asp Cys Met
455                 460                 465                 470

TAT TGG TAC AAC TTT CTG GCC TAT CAC ATG GCC AGT GCC AAG ATG CAC    2035
Tyr Trp Tyr Asn Phe Leu Ala Tyr His Met Ala Ser Ala Lys Met His
                475                 480                 485

AAG GAA CTT TGT GCT TTA ATG TTT TCC CTG GAT TGG ATT AAA GCA AAA    2083
Lys Glu Leu Cys Ala Leu Met Phe Ser Leu Asp Trp Ile Lys Ala Lys
            490                 495                 500

ACA GAA CTT GTA GGC CCT GCT CAT CTG ATT CAT GAA TTT GTG GAA TAC    2131
Thr Glu Leu Val Gly Pro Ala His Leu Ile His Glu Phe Val Glu Tyr
        505                 510                 515

AGA CAT ATA CTA GAT GAA AAG GAT TGT GCA GTC AGT GAG AAT TTT CAG    2179
Arg His Ile Leu Asp Glu Lys Asp Cys Ala Val Ser Glu Asn Phe Gln
    520                 525                 530

GAG TTT TTA TCT TTA AAT GGA CAC CTT CTT GGA CGA CAG CCA TTT CCT    2227
Glu Phe Leu Ser Leu Asn Gly His Leu Leu Gly Arg Gln Pro Phe Pro
535                 540                 545                 550

AAT ATT GTA CAA CTG GGT CTC TGT GAG CCG GAA ACT TCA GAA GTT TAT    2275
Asn Ile Val Gln Leu Gly Leu Cys Glu Pro Glu Thr Ser Glu Val Tyr
                555                 560                 565

CAG CAA GCT AAG CTG CAG GCC AAG CAG GAG GTC GAT AAT GGA ATG CTT    2323
Gln Gln Ala Lys Leu Gln Ala Lys Gln Glu Val Asp Asn Gly Met Leu
            570                 575                 580

TAC CTG GAA TGG ATA AAC AAA AAA AAC ATC ACG AAT CTT TCC CGC TTA    2371
Tyr Leu Glu Trp Ile Asn Lys Lys Asn Ile Thr Asn Leu Ser Arg Leu
        585                 590                 595

GTT GTC CGC CCC CAC ACA GAT GCT GTT TAC CAT GCC TGC TTT TCT GAG    2419
Val Val Arg Pro His Thr Asp Ala Val Tyr His Ala Cys Phe Ser Glu
    600                 605                 610

GAT GGT CAG AGA ATA GCT TCT TGT GGA GCT GAT AAA ACC TTA CAG GTG    2467
Asp Gly Gln Arg Ile Ala Ser Cys Gly Ala Asp Lys Thr Leu Gln Val
615                 620                 625                 630

TTC AAA GCT GAA ACA GGA GAG AAA CTT CTA GAA ATC AAG GCT CAT GAG    2515
Phe Lys Ala Glu Thr Gly Glu Lys Leu Leu Glu Ile Lys Ala His Glu
                635                 640                 645

GAT GAA GTG CTT TGT TGT GCA TTC TCT ACA GAT GAC AGA TTT ATA GCA    2563
Asp Glu Val Leu Cys Cys Ala Phe Ser Thr Asp Asp Arg Phe Ile Ala
            650                 655                 660
```

FIG. 5D

| | | | | | | | | | | | | | | | | |
|---|---|---|---|---|---|---|---|---|---|---|---|---|---|---|---|---|
| ACC | TGC | TCA | GTG | GAT | AAA | AAA | GTG | AAG | ATT | TGG | AAT | TCT | ATG | ACT | GGG | 2611 |
| Thr | Cys | Ser | Val | Asp | Lys | Lys | Val | Lys | Ile | Trp | Asn | Ser | Met | Thr | Gly | |
| | | 665 | | | | 670 | | | | | | 675 | | | | |
| GAA | CTA | GTA | CAC | ACC | TAT | GAT | GAG | CAC | TCA | GAG | CAA | GTC | AAT | TGC | TGC | 2659 |
| Glu | Leu | Val | His | Thr | Tyr | Asp | Glu | His | Ser | Glu | Gln | Val | Asn | Cys | Cys | |
| | 680 | | | | | 685 | | | | | 690 | | | | | |
| CAT | TTC | ACC | AAC | AGT | AGT | CAT | CAT | CTT | CTC | TTA | GCC | ACT | GGG | TCA | AGT | 2707 |
| His | Phe | Thr | Asn | Ser | Ser | His | His | Leu | Leu | Leu | Ala | Thr | Gly | Ser | Ser | |
| 695 | | | | 700 | | | | | 705 | | | | | 710 | | |
| GAC | TGC | TTC | CTC | AAA | CTT | TGG | GAT | TTG | AAT | CAA | AAA | GAA | TGT | CGA | AAT | 2755 |
| Asp | Cys | Phe | Leu | Lys | Leu | Trp | Asp | Leu | Asn | Gln | Lys | Glu | Cys | Arg | Asn | |
| | | | | 715 | | | | | 720 | | | | | 725 | | |
| ACC | ATG | TTT | GGT | CAT | ACA | AAT | TCA | GTC | AAT | CAC | TGC | AGA | TTT | TCA | CCA | 2803 |
| Thr | Met | Phe | Gly | His | Thr | Asn | Ser | Val | Asn | His | Cys | Arg | Phe | Ser | Pro | |
| | | | 730 | | | | | 735 | | | | | 740 | | | |
| GAT | GAT | AAG | CTT | TTG | GCT | AGT | TGT | TCA | GCT | GAT | GGA | ACC | TTA | AAG | CTT | 2851 |
| Asp | Asp | Lys | Leu | Leu | Ala | Ser | Cys | Ser | Ala | Asp | Gly | Thr | Leu | Lys | Leu | |
| | | 745 | | | | | 750 | | | | | 755 | | | | |
| TGG | GAT | GCG | ACA | TCA | GCA | AAT | GAG | AGG | AAA | AGC | ATT | AAT | GTG | AAA | CAG | 2899 |
| Trp | Asp | Ala | Thr | Ser | Ala | Asn | Glu | Arg | Lys | Ser | Ile | Asn | Val | Lys | Gln | |
| | 760 | | | | | 765 | | | | | 770 | | | | | |
| TTC | TTC | CTA | AAT | TTG | GAG | GAC | CCT | CAA | GAG | GAT | ATG | GAA | GTG | ATA | GTG | 2947 |
| Phe | Phe | Leu | Asn | Leu | Glu | Asp | Pro | Gln | Glu | Asp | Met | Glu | Val | Ile | Val | |
| 775 | | | | | 780 | | | | | 785 | | | | | 790 | |
| AAG | TGT | TGT | TCG | TGG | TCT | GCT | GAT | GGT | GCA | AGG | ATA | ATG | GTG | GCA | GCA | 2995 |
| Lys | Cys | Cys | Ser | Trp | Ser | Ala | Asp | Gly | Ala | Arg | Ile | Met | Val | Ala | Ala | |
| | | | 795 | | | | | 800 | | | | | 805 | | | |
| AAA | AAT | AAA | ATC | TTT | TTG | TGG | AAT | ACA | GAC | TCA | CGT | TCA | AAG | GTG | GCT | 3043 |
| Lys | Asn | Lys | Ile | Phe | Leu | Trp | Asn | Thr | Asp | Ser | Arg | Ser | Lys | Val | Ala | |
| | | | 810 | | | | | 815 | | | | | 820 | | | |
| GAT | TGC | AGA | GGA | CAT | TTA | AGT | TGG | GTT | CAT | GGT | GTG | ATG | TTT | TCT | CCT | 3091 |
| Asp | Cys | Arg | Gly | His | Leu | Ser | Trp | Val | His | Gly | Val | Met | Phe | Ser | Pro | |
| | | 825 | | | | | 830 | | | | | 835 | | | | |
| GAT | GGA | TCA | TCA | TTT | TTG | ACA | TCT | TCT | GAT | GAC | CAG | ACA | ATC | AGG | CTC | 3139 |
| Asp | Gly | Ser | Ser | Phe | Leu | Thr | Ser | Ser | Asp | Asp | Gln | Thr | Ile | Arg | Leu | |
| | 840 | | | | | 845 | | | | | 850 | | | | | |
| TGG | GAG | ACA | AAG | AAA | GTA | TGT | AAG | AAC | TCT | GCT | GTA | ATG | TTA | AAG | CAA | 3187 |
| Trp | Glu | Thr | Lys | Lys | Val | Cys | Lys | Asn | Ser | Ala | Val | Met | Leu | Lys | Gln | |
| 855 | | | | | 860 | | | | | 865 | | | | | 870 | |
| GAA | GTA | GAT | GTT | GTG | TTT | CAA | GAA | AAT | GAA | GTG | ATG | GTC | CTT | GCA | GTT | 3235 |
| Glu | Val | Asp | Val | Val | Phe | Gln | Glu | Asn | Glu | Val | Met | Val | Leu | Ala | Val | |
| | | | | 875 | | | | | 880 | | | | | 885 | | |
| GAC | CAT | ATA | AGA | CGT | CTG | CAA | CTC | ATT | AAT | GGA | AGA | ACA | GGT | CAG | ATT | 3283 |
| Asp | His | Ile | Arg | Arg | Leu | Gln | Leu | Ile | Asn | Gly | Arg | Thr | Gly | Gln | Ile | |
| | | | 890 | | | | | 895 | | | | | 900 | | | |

FIG. 5E

```
GAT TAT CTG ACT GAA GCT CAA GTT AGC TGC TGT TGC TTA AGT CCA CAT    3331
Asp Tyr Leu Thr Glu Ala Gln Val Ser Cys Cys Cys Leu Ser Pro His
        905                 910                 915

CTT CAG TAC ATT GCA TTT GGA GAT GAA AAT GGA GCC ATT GAG ATT TTA    3379
Leu Gln Tyr Ile Ala Phe Gly Asp Glu Asn Gly Ala Ile Glu Ile Leu
        920                 925                 930

GAA CTT GTA AAC AAT AGA ATC TTC CAG TCC AGG TTT CAG CAC AAG AAA    3427
Glu Leu Val Asn Asn Arg Ile Phe Gln Ser Arg Phe Gln His Lys Lys
935                 940                 945                 950

ACT GTA TGG CAC ATC CAG TTC ACA GCC GAT GAG AAG ACT CTT ATT TCA    3475
Thr Val Trp His Ile Gln Phe Thr Ala Asp Glu Lys Thr Leu Ile Ser
                955                 960                 965

AGT TCT GAT GAT GCT GAA ATT CAG GTA TGG AAT TGG CAA TTG GAC AAA    3523
Ser Ser Asp Asp Ala Glu Ile Gln Val Trp Asn Trp Gln Leu Asp Lys
                970                 975                 980

TGT ATC TTT CTA CGA GGC CAT CAG GAA ACA GTG AAA GAC TTT AGA CTC    3571
Cys Ile Phe Leu Arg Gly His Gln Glu Thr Val Lys Asp Phe Arg Leu
        985                 990                 995

TTG AAA AAT TCA AGA CTG CTT TCT TGG TCA TTT GAT GGA ACA GTG AAG    3619
Leu Lys Asn Ser Arg Leu Leu Ser Trp Ser Phe Asp Gly Thr Val Lys
     1000                1005                1010

GTA TGG AAT ATT ATT ACT GGA AAT AAA GAA AAA GAC TTT GTC TGT CAC    3667
Val Trp Asn Ile Ile Thr Gly Asn Lys Glu Lys Asp Phe Val Cys His
1015                1020                1025                1030

CAG GGT ACA GTA CTT TCT TGT GAC ATT TCT CAC GAT GCT ACC AAG TTT    3715
Gln Gly Thr Val Leu Ser Cys Asp Ile Ser His Asp Ala Thr Lys Phe
                1035                1040                1045

TCA TCT ACC TCT GCT GAC AAG ACT GCA AAG ATC TGG AGT TTT GAT CTC    3763
Ser Ser Thr Ser Ala Asp Lys Thr Ala Lys Ile Trp Ser Phe Asp Leu
                1050                1055                1060

CTT TTG CCA CTT CAT GAA TTG AGG GGC CAC AAC GGC TGT GTG CGC TGC    3811
Leu Leu Pro Leu His Glu Leu Arg Gly His Asn Gly Cys Val Arg Cys
        1065                1070                1075

TCT GCC TTC TCT GTG GAC AGT ACC CTG CTG GCA ACG GGA GAT GAC AAT    3859
Ser Ala Phe Ser Val Asp Ser Thr Leu Leu Ala Thr Gly Asp Asp Asn
        1080                1085                1090

GGA GAA ATC AGG ATA TGG AAT GTC TCA AAC GGT GAG CTT CTT CAT TTG    3907
Gly Glu Ile Arg Ile Trp Asn Val Ser Asn Gly Glu Leu Leu His Leu
1095                1100                1105                1110

TGT GCT CCG CTT TCA GAA GAA GGA GCT GCT ACC CAT GGA GGC TGG GTG    3955
Cys Ala Pro Leu Ser Glu Glu Gly Ala Ala Thr His Gly Gly Trp Val
        1115                1120                1125

ACT GAC CTT TGC TTT TCT CCA GAT GGC AAA ATG CTT ATC TCT GCT GGA    4003
Thr Asp Leu Cys Phe Ser Pro Asp Gly Lys Met Leu Ile Ser Ala Gly
        1130                1135                1140
```

FIG. 5F

| | |
|---|---|
| GGA TAT ATT AAG TGG TGG AAC GTT GTC ACT GGG GAA TCC TCA CAG ACC<br>Gly Tyr Ile Lys Trp Trp Asn Val Val Thr Gly Glu Ser Ser Gln Thr<br>    1145             1150             1155 | 4051 |
| TTC TAC ACA AAT GGA ACC AAT CTT AAG AAA ATA CAC GTG TCC CCT GAC<br>Phe Tyr Thr Asn Gly Thr Asn Leu Lys Lys Ile His Val Ser Pro Asp<br>    1160             1165             1170 | 4099 |
| TTC AAA ACA TAT GTG ACT GTG GAT AAT CTT GGT ATT TTA TAT ATT TTA<br>Phe Lys Thr Tyr Val Thr Val Asp Asn Leu Gly Ile Leu Tyr Ile Leu<br>1175             1180             1185             1190 | 4147 |
| CAG ACT TTA GAA TAAAATAGTT AAGCATTAAT GTAGTTGAAC TTTTTAAATT TTTGA<br>Gln Thr Leu Glu<br>         1 | 4204 |

| | |
|---|---|
| ATTGGAAAAA AATTCTAATG AAACCCTGAT ATCAACTTTT TATAAAGCTC TTAATTGTTG | 4264 |
| TGCAGTATTG CATTCATTAC AAAAGTGTTT GTGGTTGGAT GAATAATATT AATGTAGCTT | 4324 |
| TTTCCCAAAT GAACATACCT TTAATCTTGT TTTTCATGAT CATCATTAAC AGTTTGTCCT | 4384 |
| TAGGATGCAA ATGAAAATGT GAATACATAC CTTGTTGTAC TGTTGGTAAA ATTCTGTCTT | 4444 |
| GATGCATTCA AAATGGTTGA CATAATTAAT GAGAAGAATT TGGAAGAAAT TGGTATTTTA | 4504 |
| ATACTGTCTG TATTTATTAC TGTTATGCAG GCTGTGCCTC AGGGTAGCAG TGGCCTGCTT | 4564 |
| TTTGAACCAC ACTTACCCCA AGGGGGTTTT GTTCTCCTAA ATACAATCTT AGAGGTTTTT | 4624 |
| TGCACTCTTT AAATTTGCTT TAAAAATATT GTGTCTGTGT GCATAGTCTG CAGCATTTCC | 4684 |
| TTAATTGAC TCAATAAGTG AGTCTTGGAT TTAGCAGGCC CCCCCACCTT TTTTTTTTGT | 4744 |
| TTTTGGAGAC AGAGTCTTGC TTTGTTGCCA GGCTGGAGTG CAGTGGCGCG ATCTCGGCTC | 4804 |
| ACCACAATCG CTGCCTCCTG GGTTCAAGCA ATTCTCCTGC CTCAGCCTCC CGAGTAGCTG | 4864 |
| GGACTACAGG TGTGCGCACA TGCCAGGCTA ATTTTTGTAT TTTTAGTAGA GACGGGGTTT | 4924 |
| CACCATGTTG GCCGGGATGG TCTCGATCTC TTGACCTCAT GATCTACCCG CCTTGGCCTC | 4984 |
| CCAAAGTGCT GAGATTACAG GCGTGAGCCA CCGTGCCTGG CCAGGCCCCT CTCTTTTAA | 5044 |
| TGGAGACAGG GTCTTGCACT ATCACCCAGG CTGGAGTGCA GTGGCATAAT CATACCTCAT | 5104 |
| TGCAGCCTCA GACTCCTGGG TTCAAGCAAT CCTCCTGCCT CAGCCTCCCA AGTAGCTGAG | 5164 |
| ACTGCAGGCA CGAGCCACCA CACCCAGCTA ATTTTTAAGT TTTCTTGTAG AGACAGGGTC | 5224 |
| TCACTATGTT GTCTAGGCTG GTCTTGAACT CTTGGCCTCA AGTAATCCTC CTGCCTCAGC | 5284 |
| CTCCCAAAGT GTTGGGATTG CAGATATGAG CCACTGGCCT GGCCTTCAGC AGTTCTTTTT | 5344 |
| GTGAAGTAAA ACTTGTATGT TGGAAAGAGT AGATTTTATT GGTCTACCCT TTTCTCACTG | 5404 |
| TAGCTGCTGG CAGCCCTGTG CCATATCTGG ACTCTAGTTG TCAGTATCTG AGTTGGACAC | 5464 |
| TATTCCTGCT CCCTCTTGTT TCTTACATAT CAGACTTCTT ACTTGAATGA AACCTGATCT | 5524 |
| TTCCTAATCC TCACTTTTTT CTTTTTTAAA AAGCAGTTTC TCCACTGCTA AATGTTAGTC | 5584 |
| ATTGAGGTGG GGCCAATTTT AATCATAAGC CTTAATAAGA TTTTTCTAAG AAATGTGAAA | 5644 |
| TAGAACAATT TTCATCTAAT TCCATTTACT TTTAGATGAA TGGCATTGTG AATGCCATTC | 5704 |
| TTTTAATGAA TTTCAAGAGA ATTCTCTGGT TTTCTGTGTA ATTCCAGATG AGTCACTGTA | 5764 |
| ACTCTAGAAG ATTAACCTTC CAGCCAACCT ATTTTCCTTT CCCTTGTCTC TCTCATCCTC | 5824 |
| TTTTCCTTCC TTCTTTCCTT TCTCTTCTTT TATCTCCAAG GTTAATCAGG AAAAATAGCT | 5884 |
| TTTGACAGGG GAAAAAACTC AATAACTAGC TATTTTTGAC CTCCTGATCA GGAACTTTAG | 5944 |
| TTGAAGCGTA AATCTAAAGA AACATTTTCT CTGAAATATA TTATTAAGGG CAATGGAGAT | 6004 |
| AAATTAATAG TAGATGTGGT TCCCAGAAAA TATAATCAAA ATTCAAAGAT TTTTTTTGTT | 6064 |
| TCTGTAACTG GAACTAAATC AAATGATTAC TAGTGTTAAT AGTAGATAAC TTGTTTTTAT | 6124 |
| TGTTGGTGCA TATTAGTATA ACTGTGGGGT AGGTCGGGGA GAGGGTAAGG GAATAGATCA | 6184 |
| CTCAGATGTA TTTTAGATAA GCTATTTAGC CTTTGATGGA ATCATAAATA CAGTGAATAC | 6244 |
| AATCCTTTGC ATTGTTAAGG AGGTTTTTTG TTTTTAAATG GTGGGTCAAG GAGCTAGTTT | 6304 |
| ACAGGCTTAC TGTGATTTAA GCAAATGTGA AAAGTGAAAC CTTAATTTTA TCAAAAGAAA | 6364 |
| TTTCTGTAAA TGGTATGTCT CCTTAGAATA CCCAAATCAT AATTTTATTT GTACACACTG | 6424 |
| TTAGGGGCTC ATCTCATGTA GGCAGAGTAT AAAGTATTAC CTTTTGGAAT TAAAAGCCAC | 6484 |

```
TGACTGTTAT AAAGTATAAC AACACACATC AGGTTTTAAA AAGCCTTGAA TGGCCCTTGT    6544
CTTAAAAAGA AATTAGGAGC CAGGTGCGGT GGCACGTGCC TGTAGTCCCA GCTCCTTGGG    6604
AGGCTGAGAC AGGAGGATTC CTTGAGCCCT GGAGTTTGAG TCCAGCCTGG GTGACATAGC    6664
AAGACCCTGT CTTAAAAGAA AAATGGGAAG AAAGACAAGG TAACATGAAG AAAGAAGAGA    6724
TACCTAGTAT GATGGAGCTG CAAATTTCAT GGCAGTTCAT GCAGTCGGTC AAGAGGAGGA    6784
TTTTGTTTTG TAGTTTGCAG ATGAGCATTT CTAAAGCATT TCCCTTGCT GTATTTTTTT     6844
GTATTATAAA TTACATTGGA CTTCATATAT ATAATTTTTT TTTACATTAT ATGTCTCTTG    6904
TATGTTTTGA AACTCTTGTA TTTATGATAT AGCTTATATG ATTTTTTTGC CTTGGTATAC    6964
ATTTTAAAAT ATGAATTTAA AAAATTTTTG TAAAAATAAA ATTCACAAAA TTGTTTTGAA    7024
AAACAAAAAA AAAAAAA                                                    7042
```

```
MDAKARNCLLQHREALEKDIKTSYIMDHMISDGFLTISEE      40
EKVRNEPTQQQRAAMLIKMILKKDNDSYVSFYNALLHEGY      80
KDLAALLHDGIPVVSSSSVRTVLCEGGVPQRPVVFVTRKK     120
LVNAIQQKLSKLKGEPGWVTIHGMAGCGKSVLAAEAVRDH     160
SLLEGCFPGGVHWVSVGKQDKSGLLMKLQNLCTRLDQDES     200
FSQRLPLNIEEAKDRLRILMLRKHPRSLLILDDVWDSWVL     240
KAFDSQCQILLTTRDKSVTDSVMGPKYVVPVESSLGKEKG     280
LEILSLFVNMKKADLPEQAHSIIKECKGSPLVVSLIGALL     320
RDFPNRWEYYLKQLQNKQFKRIRKSSSYDYEALDEAMSIS     360
VEMLREDIKDYYTDLSILQKDVKVPTKVLCILWDMETEEV     400
EDILQEFVNKSLLFCDRNGKSFRYYLHDLQVDFLTEKNCS     440
QLQDLHKKIITQFQRYHQPHTLSPDQEDCMYWYNFLAYHM     480
ASAKMHKELCALMFSLDWIKAKTELVGPAHLIHEFVEYRH     520
ILDEKDCAVSENFQEFLSLNGHLLGRQPFPNIVQLGLCEP     560
ETSEVYQQAKLQAKQEVDNGMLYLEWINKKNITNLSRLVV     600
RPHTDAVYHACFSEDGQRIASCGADKTLQVFKAETGEKLL     640
EIKAHEDEVLCCAFSTDDRFIATCSVDKKVKIWNSMTGEL     680
VHTYDEHSEQVNCCHFTNSSHHLLLATGSSDCFLKLWDLN     720
QKECRNTMFGHTNSVNHCRFSPDDKLLASCSADGTLKLWD     760
ATSANERKSINVKQFFLNLEDPQEDMEVIVKCCSWSADGA     800
RIMVAAKNKIFLWNTDSRSKVADCRGHLSWVHGVMFSPDG     840
SSFLTSSDDQTIRLWETKKVCKNSAVMLKQEVDVVFQENE     880
VMVLAVDHIRRLQLINGRTGQIDYLTEAQVSCCCLSPHLQ     920
YIAFGDENGAIEILELVNNRIFQSRFQHKKTVWHIQFTAD     960
EKTLISSSDDAEIQVWNWQLDKCIFLRGHQETVKDFRLLK    1000
NSRLLSWSFDGTVKVWNIITGNKEKDFVCHQGTVLSCDIS    1040
HDATKFSSTSADKTAKIWSFDLLLPLHELRGHNGCVRCSA    1080
FSVDSTLLATGDDNGEIRIWNVSNGELLHLCAPLSEEGAA    1120
THGGWVTDLCFSPDGKMLISAGGYIKWWNVVTGESSQTFY    1160
TNGTNLKKIHVSPDFKTYVTVDNLGILYILQTLE         1194
```

FIG. 8

```
Apaf-1   1  MDAKARNCLLQHREAL-EKDIKTSYIMDHMISDGFLTISEE
CED-1    1  MMRQDRRSLLERNIMFSSHLKVDEILEVLIAKQVINSDNG Apaf-1  40  EKVRNEPTQQQRAAMLIKMILKKDNDSYVSFYNALHEGYK
CED-3   41  DMINSCGTVREKRRELVKAVQRRGDVAFDAFYDALRSTGHE Apaf-1  80  DIAALI         85
CED-3   81  GIAFVL         86
```

FIG. 9

```
Apaf-1  92  PVVSSSVRTVLCEGGVPQRPVVFVTRKKLVNAIQQKLSK
CED-4  108  PQFSRQMLDRKLLIGNVPKQMTCYI-REYHVDRMIKKLDE Apaf-1 132  L-KGEPGWVIIHGMAGCGKSVIAEAVRDHSLIEGCFPGG
CED-4 147  MCDLDSFFLFLHGRAGSGKSVIASQALSKSDQLIGINYDS Apaf-1 171  VHWV-SVGKQDKSGILMKLQNLCTRLDQESFS-QRLPLN
CED-4 188  IVWLKDSGTAPKSIEDLFTDILMLKSEDDLLNFPSVEHV Apaf-1 209  IEEAKDRIRILMLRKHPRSLLIIDDVWDSWVLK-AFDSQ
CED-4 227  TSVVLKRMICNALIDRPNILFVFDDVQEETIRMAQEIRL Apaf-1 248  QILTTRDKSVTDSVMGPKYVVPVESSLGKEKGLEILSLF
CED-4 265  RCLMTTRDVELSNAASQTCEFIFV-ISLEIDECYDFLEAY Apaf-1 288  -VNMKKADLPEQA-HSIIKECKGSP--LVVSIIGALLRDF
CED-4 306  GMPMPVGEKEEDVLNKTIELSSGNPATLMFEKSCEPKTE Apaf-1 324  PNRW-EYYLKQLQNKQFKRIRKSSSYDYEALDEAMSISVE
CED-4 346  -EKMAQLNNK-LESRGLVGECITPYSYKSLAMALQRCVE Apaf-1 363  MLREDIKDYYTDLSIIQKDVKVFTKVL-CILW-DMETEEV
CED-4 384  VLSDEDRSALAFAVMPPGVDIPVKLWSCVIPVDICSNEE Apaf-1 401  EDILQEFVNKSL
CED-4 424  EQ-LDDEVADRL
```

FIG. 16A

Apaf-IL

| | |
|---|---|
| Contig Length: | 7810 bases |
| Average Length/Sequence: | 660 bases |
| Total Sequence Length: | 42284 bases |
| Top Strand: | 34 sequences |
| Bottom Strand: | 30 sequences |
| Total: | 64 sequences |

```
            10        20        30        40
            |         |         |         |
    AAGAAGAGGTAGCGAGTGGACGTGACTGCTCTATCCCGGG   40
    CAAAAGGGATAGAACCAGAGGTGGGGAGTCTGGGCAGTCG   80
    GCGACCCGCGAAGACTTGAGGTGCCGCAGCGGCATCCGGA  120
    GTAGCGCCGGGCTCCCTCCGGGGTGCAGCCGCCGTCGGGG  160
    GAAGGGCGCCACAGGCCGGGAAGACCTCCTCCCTTTGTGT  200

210       220       230       240
            |         |         |         |
    CCAGTAGTGGGGTCCACCGGAGGGCGGCCCGTGGGCCGGG  240
    CCTCACCGCGGCGCTCCGGGACTGTGGGGTCAGGCTGCGT  280
    TGGGTGGACGCCCACCTCGCCAACCTTCGGAgGTCCCTGG  320
    GGGTCTTCGTGCGCCCCGGGGCTGCAGAGATCCAGGGGAG  360
    GCGCCTGTGAGGCCCGGACCTGCCCCGGGGCGAAGGGTAT  400

410       420       430       440
            |         |         |         |
    GTGGCGAGACAGAGCCCTGCACCCCTAATTCCCGGTGGAA  440
    AACTCCTGTTGCCGTTTCCCTCCACCGGCCTGGAGTCTCC  480
    CAGTCTTGTCCCGGCAGTGCCGCCCTCCCCACTAAGACCT  520
    AGGCGCAAAGGCTTGGCTCATGGTTGACAGCTCAGAGAGA  560
START GAAAGATCTGAGGGAAG[ATG]GATGCAAAAGCTCGAAATTG  600
578
            610       620       630       640
            |         |         |         |
    TTTGCTTCAACATAGAGAAGCTCTGGAAAAGGACATCAAG  640
    ACATCCTACATCATGGATCACATGATTAGTGATGGATTTT  680
    TAACAATATCAGAAGAGGAAAAGTAAGAAATGAGCCCAC   720
    TCAACAGCAAAGAGCAGCTATGCTGATTAAAATGATACTT  760
    AAAAAAGATAATGATTCCTACGTATCATTCTACAATGCTC  800
```

FIG. 16 B

```
          810       820       830       840
           |         |         |         |
TACTACATGAAGGATATAAAGATCTTGCTGCCCTTCTCCA  840
TGATGGCATTCCTGTTGTCTCTTCTTCCAGTGGTAAAGAT  880
TCAGTTAGTGGAATAACTTCGTATGTAAGGACAGTCCTGT  920
GTGAAGGTGGAGTACCACAGAGGCCAGTTGTTTTTGTCAC  960
AAGGAAGAAGCTGGTGAATGCAATTCAGCAGAAGCTCTCC 1000

1010      1020      1030      1040
           |         |         |         |
AAATTGAAAGGTGAACCAGGATGGGTCACCATACATGGAA 1040
TGGCAGGCTGTGGGAAGTCTGTATTAGCTGCAGAAGCTGT 1080
TAGAGATCATTCCTTTTAGAAGGTTGTTTCCCAGGGGGA  1120
GTGCATTGGGTTTCAGTTGGGAAACAAGACAAATCTGGGC 1160
TTCTGATGAAACTGCAGAATCTTTGCACACGGTTGGATCA 1200

1210      1220      1230      1240
           |         |         |         |
GGATGAGAGTTTTTCCCAGAGGCTTCCACTTAATATTGAA 1240
GAGGCTAAAGACCGTCTCCGCATTCTGATGCTTCGCAAAC 1280
ACCCAAGGTCTCTCTTGATCTTGGATGATGTTTGGGACTC 1320
TTGGGTGTTGAAAGCTTTTGACAGTCAGTGTCAGATTCTT 1360
CTTACAACCACAGACAAGAGTGTTACAGATTCAGTAATGG 1400

1410      1420      1430      1440
           |         |         |         |
GTCCTAAATATGTAGTCCCTGTGGAGAGTTCCTTAGGAAA 1440
GGAAAAGGACTTGAAATTTATCCTTTTTGTTAATATG    1480
AAGAAGGCAGATTTGCCAGAACAAGCTCATAGTATTATAA 1520
AAGAATGTAAAGGCTCTCCCCTTGTAGTATCTTTAATTGG 1560
TGCACTTTTACGTGATTTTCCCAATCGCTGGGAGTACTAC 1600

1610      1620      1630      1640
           |         |         |         |
CTCAAACAGCTTCAGAATAAGCAGTTTAAGAGAATAAGGA 1640
AATCTTCGTCTTATGATTATGAGGCTCTAGATGAAGCCAT 1680
GTCTATAAGTGTTGAAATGCTCAGAGAAGACATCAAAGAT 1720
TATTACACAGATCTTTCCATCCTTCAGAAGGACGTTAAGG 1760
TGCCTACAAAGGTGTTATGTATTCTCTGGGACATGGAAAC 1800
```

FIG. 16C

```
          1810        1820        1830        1840
           |           |           |           |
  TGAAGAAGTTGAAGACATACTGCAGGAGTTTGTAAATAAG  1840
  TCTCTTTTATTCTGTGATCGGAATGGAAAGTCGTTTCGTT  1880
  ATTATTTACATGATCTTCAAGTAGATTTTCTTACAGAGAA  1920
  GAATTGCAGCCAGCTTCAGGATCTACATAAGAAGATAATC  1960
  ACTCAGTTTCAGAGATATCACCAGCCGCATACTCTTTCAC  2000

2010        2020        2030        2040
           |           |           |           |
  CAGATCAGGAAGACTGTATGTATTGGTACAACTTTCTGGC  2040
  CTATCACATGGCCAGTGCCAAGATGCACAAGGAACTTTGT  2080
  GCTTTAATGTTTTCCCTGGATTGGATTAAAGCAAAAACAG  2120
  AACTTGTAGGCCCTGCTCATCTGATTCATGAATTTGTGGA  2160
  ATACAGACATATACTAGATGAAAGGATTGTGCAGTCAGT   2200

2210        2220        2230        2240
           |           |           |           |
  GAGAATTTTCAGGAGTTTTTATCTTTAAATGGACACCTTC  2240
  TTGGACGACAGCCATTTCCTAATATTGTACAACTGGGTCT  2280
  CTGTGAGCCGGAAACTTCAGAAGTTTATCAGCAAGCTAAG  2320
  CTGCAGGCCAAGCAGGAGGTCGATAATGGAATGCTTTACC  2360
  TGGAATGGATAAACAAAAAAACATCACGAATCTTTCCCG   2400

2410        2420        2430        2440
           |           |           |           |
  CTTAGTTGTCCGCCCCACACAGATGCTGTTTACCATGCC   2440
  TGCTTTTCTGAGGATGGTCAGAGAATAGCTTCTTGTGGAG  2480
  CTGATAAAACCTTACAGGTGTTCAAAGCTGAAACAGGAGA  2520
  GAAACTTCTAGAAATCAAGGCTCATGAGGATGAAGTGCTT  2560
  TGTTGTGCATTCTCTACAGATGACAGATTTATAGCAACT   2600

2610        2620        2630        2640
           |           |           |           |
  GCTCAGTGGATAAAAAGTGAAGATTTGGAATTCTATGAC   2640
  TGGGGAACTAGTACACACCTATGATGAGCACTCAGAGCAA  2680
  GTCAATTGCTGCCATTTCACCAACAGTAGTCATCATCTTC  2720
  TCTTAGCCACTGGGTCAAGTGACTGCTTCCTCAAACTTTG  2760
  GGATTTGAATCAAAAGAATGTCGAAATACCATGTTTGGT   2800
```

FIG. 16D

```
         2810      2820      2830      2840
CATACAAATTCAGTCAATCACTGCAGATTTTCACCAGATG 2840
ATAAGCTTTTGGCTAGTTGTTCAGCTGATGGAACCTTAAA 2880
GCTTTGGGATGCGACATCAGCAAATGAGAGGAAAAGCATT 2920
AATGTGAAACAGTTCTTCCTAAATTTGGAGGACCCTCAAG 2960
AGGATATGGAAGTGATAGTGAAGTGTTGTTCGTGGTCTGC 3000

3010      3020      3030      3040
TGATGGTGCAAGGATAATGGTGGCAGCAAAAAATAAAATC 3040
TTTTTGTGGAATACAGACTCACGTTCAAGGTGGCTGATT 3080
GCAGAGGACaTTTAAGTTGGGTTCATGGTGTGATGTTTTC 3120
TCCTGATGGATCATCATTTTGACATCTTCTGATGACCAG 3160
ACAATCAGGCTCTGGGAGACAAGAAAGTATGTAAGAACT 3200

3210      3220      3230      3240
CTGCTGTAATGTTAAAGCAAGAAGTAGATGTTGTGTTTCA 3240
AGAAAATGAAGTGATGGTCCTTGCAGTTGACCATATAAGA 3280
CGTCTGCAACTCATTAATGGAAGAACAGGTCAGATTGATT 3320
ATCTGACTGAAGCTCAAGTTAGCTGCTGTTGCTTAAGTCC 3360
ACATCTTCAGTACATTGCATTTGGAGATGAAAATGGAGCC 3400

3410      3420      3430      3440
ATTGAGATTTTAGAACTTGTAAACAATAGAATCTTCCAGT 3440
CCAGGTTTCAGCACAAGAAAACTGTATGGCACATCCAGTT 3480
CACAGCCGATGAGAAGACTCTTATTTCAAGTTCTGATGAT 3520
GCTGAAATTCAGGTATGGAATTGGCAATTGGACAAATGTA 3560
TCTTTCTACCAGGCCATCAGGAACAGTGAAAGAcTTTAG 3600

3610      3620      3630      3640
ACTCTTGAAAAATTCAAGACTGCTTTCTTGGTCATTTGAT 3640
GGAACAGTGAAGGTATGGAATATTATTACTGGAAATAAAG 3680
AAAAAGACTTTGTCTGTCACCAGGGTACAGTACTTTCTTG 3720
TGACATTTCTCACGATGCTACCAAGTTTTCATCTACCTCT 3760
GCTGACAAGACTGCAAACATCTGGAGTTTTGATCTCCTTT 3800
```

FIG. 16E

```
       3810      3820      3830      3840
        |         |         |         |
TGCCACTTCATGAATTGAGGGGCCACAACGGCTGTGCG  3840
CTGCTCTGCCTTCTCTGTGGACAGTACCTGCTGGCAACG 3880
GGAGATGACAATGGAGAAATCAGGATATGGAATGTCTCAA 3920
ACGGTGAGCTTCTTCATTTGTGTGCTCCGCTTTCAGAAGA 3960
AGGAGCTGCTACCCATGGAGGCTGGGTGACTGACCTTTGC 4000

4010      4020      4030      4040
        |         |         |         |
TTTTCTCCAGATGGCAAAATGCTTATCTCTGCTGGAGGAT 4040
ATATTAAGTGGTGGAACGTTGTCACTGGGGAATCCTCACA 4080
GACCTTCTACACAAATGGAACCAATCTTAAGAAAATACAC 4120
GTGTCCCTGACTTCAAAACATATGTGACTGTGGATAATC 4160
TTGGTATTTTATATATTTTACAGACTTTAGAATAAAATAG 4200   4192=end
                                STOP 4210      4220      4230      4240
        |         |         |         |
TTAAGCATTAATGTAGTTGAACTTTTTAAATTTTTGAATT 4240
GGAAAAAAATTCTAATGAAACCCTGATATCAACTTTTTAT 4280
AAAGCTCTTAATTGTTGTGCAGTATTGCATTCATTACAAA 4320
AGTGTTTGTGGTTGGATGAATAATATTAATGTAGCTTTTT 4360
CCCAAATGAACATACCTTTAATCTTGTTTTCATGATCAT  4400

4410      4420      4430      4440
        |         |         |         |
CATTAACAGTTTGTCCTTAGGATGCAAATGAAAATGTGAA 4440
TACATACCTTGTTGTACTGTTGGTAAAATTCTGTCTTGAT 4480
GCATTCAAAATGGTTGACATAATTAATGAGAAGAATTTGG 4520
AAGAAATTGGTATTTAATACTGTCTGTATTTATTACTGT  4560
TATGCAGGCTGTGCCTCAGGGTAGCAGTGGCCTGCTTTTT 4600

4610      4620      4630      4640
        |         |         |         |
GAACCACACTTACCCCAAGGGGGTTTTGTTCTCCTAAATA 4640
CAATCTTAGAGGTTTTTGCACTCTTTAAATTTGCTTTAA  4680
AAATATTGTGTCTGTGTGCATAGTCTGCAGCATTTCCTTT 4720
AATTGACTCAATAAGTGAGTCTTGGATTTAGCAGGCCCCC 4760
CCACCTTTTTTTTTGTTTTGGAGACAGAGTCTTGCTTT   4800
```

FIG. 16F

```
         4810      4820      4830      4840
GTTGCCAGGCTGGAGTGCAGTGGCGCGATCTCGGCTCACC  4840
ACAATCGCTGCCTCCTGGGTTCAAGCAATTCTCCTGCCTC  4880
AGCCTCCCGAGTAGCTGGGACTACAGGTGTGCGCACATGC  4920
CAGGCTAATTTTTGTATTTTTAGTAGAGACGGGGTTTCAC  4960
CATGTTGGCCGGGATGGTCTCGATCTCTTGACCTCATGAT  5000

5010      5020      5030      5040
CTACCGCCTTGGCCTCCCAAAGTGCTGAGATTACAGGCG   5040
TGAGCCACCGTGCCTGGCCAGGCCCCTTCTCTTTTAATGG  5080
AGACAGGGTCTTGCACTATCACCCAGGCTGGAGTGCAGTG  5120
GCATAATCATACCTCATTGCAGCCTCAGACTCCTGGGTTC  5160
AAGCAATCCTCCTGCCTCAGCCTCCCAAGTAGCTGAGACT  5200

5210      5220      5230      5240
GCAGGCACGAGCCACCACACCCAGCTAATTTTTAAGTTTT  5240
CTTGTAGAGACAGGGTCTCACTATGTTGTCTAGGCTGGTC  5280
TTGAACTCTTGGCCTCAAGTAATCCTCCTGCCTCAGCCTC  5320
CCAAAGTGTTGGGATTGCAGATATGAGCCACTGGCCTGGC  5360
CTTCAGCAGTTCTTTTGTGAAGTAAAACTTGTATGTTGG   5400

5410      5420      5430      5440
AAAGAGTAGATTTTATTGGTCTACCCTTTTCTCACTGTAG  5440
CTGCTGGCAGCCCTGTGCCATATCTGGACTCTAGTTGTCA  5480
GTATCTGAGTTGGACACTATTCCTGCTCCTCTTGTTTCT   5520
TACATATCAGACTTCTTACTTGAATGAAACCTGATCTTTC  5560
CTAATCCTCACTTTTTCTTTTTAAAAGCAGTTTCTCC     5600

5610      5620      5630      5640
ACTGCTAAATGTTAGTCATTGAGGTGGGGCCAATTTTAAT  5640
CATAAGCCTTAATAAGATTTTTCTAAGAAATGtGAAATAG  5680
AACAATTTTCATCTAATTCCATTTACTTTTAGATGAATGG  5720
CATTGTGAATGCCATTCTTTTAATGAATTTCAAGAGAATT  5760
CTCTGGTTTTCTGTGTAATTCCAGATGAGTCACTGTAACT 5800
```

FIG. 16G

```
          5810      5820      5830      5840
           |         |         |         |
CTAGAAGATTAACCTTCCAGCCAACCTATTTTCCTTTCCC  5840
TTGTCTCTCTCATCCTCTTTTCCTTCCTTCTTTCCTTTCT  5880
CTTCTTTTATCTCCAAGGTTAATCAGGAAAATAGCTTTT   5920
GACAGGGgAAAAACTCAATAACTAGCTATTTTGACCTC    5960
CTGATCAGGAACTTTAGTTGAAGCGTAAATCTAAAGAAAC  6000

6010      6020      6030      6040
           |         |         |         |
ATTTTCTCTGAAATATATTATTAAGGGCAATGGAGATAAA  6040
TTAATAGTAGATGTGGTTCCCAGAAAATATAATCAAAATT  6080
CAAAGATTTTTTTGTTTCTGTAACTGGAACTAAATCAAA   6120
TGATTACTAGTGTTAATAGTaGATAACTTGTTTTTATTGT  6160
TGGTGCATATTAGTATAACTGTGGGTAGGTCGGGGAGAG   6200

6210      6220      6230      6240
           |         |         |         |
GGTAAGGGAATAGATCACTCAGATGTATTTTAGATAAGCT  6240
ATTTAGCCTTTGATGGAATCATAAATACAGTGAATACAAT  6280
CCTTTGCATTGTTAAGGAGGTTTTTGTTTTAAATGGTG    6320
GGTCAAGGAGCTAGTTTACAGGCTTACTGTGATTTAAGCA  6360
AATGTGAAAGTGAAACCTTAATTTTATCAAAAGAAATTT   6400

6410      6420      6430      6440
           |         |         |         |
CTGTAAATGGTATGTCTCCTTAGAATACCCAAATCATAAT  6440
TTTATTTGTACACACTGTTAGGGgCTCATCTCATGTAGGC  6480
AGAGTATAAAGTATTACCTTTTGGAATTAAAAGCCACTGA  6520
CTGTTATAAAGTATAACAACACACATCAGGTTTTAAAAAG  6560
CCTTGAATGGCCCTTGTCTTAAAAGAAATTAGGAGCCAG   6600

6610      6620      6630      6640
           |         |         |         |
GTGCGGTGGCACGTGCCTGTAGTCCCAGCTCCTTGGGAGG  6640
CTGAGACAGGAGGATTCCTTGAGCCCTGGAGTTTGAGTCC  6680
AGCCTGGGTGACATAGCAAGACCCTGTCTTAAAAGAAAA   6720
TGGAAGAAAGACAAGGTAACATGAAGAAGAAGAGATAC    6760
CTAGTATGATGGAGCTGCAAATTTCATGGCAGTTCATGCA  6800
```

FIG. 16 H

```
         6810        6820        6830        6840
          |           |           |           |
GTCGGTCAAGAGGAGGATTTTGTTTTGTAGTTTGCAGATG  6840
AGCATTTCTAAAGCATTTTCCCTTGCTGTATTTTTTTGTA  6880
TTATAAATTACATTGGACTTCATATATAAtTTTTTTTT    6920
ACATTATATGTCTCTTGTATGTTTGAAACTCTTGTATTT   6960
ATGATATAGCTTATATGATTTTTTGCCTTGGTATACATT   7000

7010        7020        7030        7040
          |           |           |           |
TTAAAATATGAATTTAAAAATTTTTGTAAAAATAAAATT   7040
CACAAAATTGTTTTGAAAACAAAAAAAAAAAAA         7075
```

FIG. 17

| | |
|---|---|
| MDAKARNCLLQHREALEKDIKTSYIMDHMISDGFLTISEE | 40 |
| EKVRNEPTQQQRAAMLIKMILKKDNDSYVSFYNALLHEGY | 80 |
| KDLAALLHDGIPVVS<u>SSSGKDSVSGITSY</u>VRTVLCEGGVP | 120 |
| QRPVVFVTRKKLVNAIQQKLSKLKGEPGWVTIHGMAGCGK | 160 |
| SVLAAEAVRDHSLLEGCFPGGVHWVSVGKQDKSGLLMKLQ | 200 |
| NLCTRLDQDESFSQRLPLNIEEAKDRLRILMLRKHPRSLL | 240 |
| ILDDVWDSWVLKAFDSQCQILLTTRDKSVTDSVMGPKYVV | 280 |
| PVESSLGKEKGLEILSLFVNMKKADLPEQAHSIKECKGS | 320 |
| PLVVSLIGALLRDFPNRWEYYLKQLQNKQFKRIRKSSSYD | 360 |
| YEALDEAMSISVEMLREDIKDYYTDLSILQKDVKVPTKVL | 400 |
| CILWDMETEEVEDILQEFVNKSLLFCDRNGKSFRYYLHDL | 440 |
| QVDFLTEKNCSQLQDLHKKIITQFQRYHQPHTLSPDQEDC | 480 |
| MYWYNFLAYHMASAKMHKELCALMFSLDWIKAKTELVGPA | 520 |
| HLIHEFVEYRHILDEKDCAVSENFQEFLSLNGHLLGRQPF | 560 |
| PNIVQLGLCEPETSEVYQQAKLQAKQEVDNGMLYLEWINK | 600 |
| KNITNLSRLVVRPHTDAVYHACFSEDGQRIASCGADKTLQ | 640 |
| VFKAETGEKLLEIKAHEDEVLCCAFSTDDRFIATCSVDKK | 680 |
| VKIWNSMTGELVHTYDEHSEQVNCCHFTNSSHHLLLATGS | 720 |
| SDCFLKLWDLNQKECRNTMFGHTNSVNHCRFSPDDKLLAS | 760 |
| CSADGTLKLWDATSANERKSINVKQFFLNLEDPQEDMEVI | 800 |
| VKCCSWSADGARIMVAAKNKIFLWNTDSRSKVADCRGHLS | 840 |
| WVHGVMFSPDGSSFLTSSDDQTIRLWETKKVCKNSAVMLK | 880 |
| QEVDVVFQENEVMVLAVDHIRRLQLINGRTGQIDYLTEAQ | 920 |
| VSCCCLSPHLQYIAFGDENGAIEILELVNNRIFQSRFQHK | 960 |
| KTVWHIQFTADEKTLISSSDDAEIQVWNWQLDKCIFLRGH | 1000 |
| QETVKDFRLLKNSRLLSWSFDGTVKVWNIITGNKEKDFVC | 1040 |
| HQGTVLSCDISHDATKFSSTSADKTAKIWSFDLLLPLHEL | 1080 |
| RGHNGCVRCSAFSVDSTLLATGDDNGEIRIWNVSNGELLH | 1120 |
| LCAPLSEEGAATHGGWVTDLCFSPDGKMLISAGGYIKWWN | 1160 |
| VVTGESSQTFYTNGTNLKKIHVSPDFKTYVTVDNLGILYI | 1200 |
| LQTLE | 1205 |

APAF-1 AN ACTIVATOR OF CASPASE-3

This a divisional application under 35 U.S.C. §120 of U.S. Ser. No. 09/092,508, filed Jun. 5, 1998, which claims benefit of applications U.S. Ser. No. 60/055,258, filed Aug. 7, 1997 and U.S. Ser. No. 60/048,807, filed Jun. 5, 1997, which are incorporated herein by reference.

FIELD OF THE INVENTION

The present invention relates generally to the identification, isolation, and recombinant production of a novel protein, designated herein as "Apaf-1".

BACKGROUND OF THE INVENTION

Apoptosis or "Programmed Cell Death"

Control of cell numbers in mammals is believed to be determined, in part, by a balance between cell proliferation and cell death. One form of cell death, sometimes referred to as necrotic cell death, is typically characterized as a pathologic form of cell death resulting from some trauma or cellular injury. In contrast, another "physiologic" form of cell death usually proceeds in an orderly or controlled manner. This orderly or controlled form of cell death is often referred to as "apoptosis" (see, e.g., Barr, et al., *Bio/Technology*, 12:487–493 (1994); Steller, et al., *Science*, 267:1445–1449 (1995)).

Apoptotic cell death naturally occurs in many physiological processes, including embryonic development and clonal selection in the immune system (Itoh, et al., *Cell*, 66:233–243 (1991)). Decreased levels of apoptotic cell death have been associated with a variety of pathological conditions, including cancer, lupus, and herpes virus infection (Thompson. *Science*, 267:1456–1462 (1995)). Increased levels of apoptotic cell death may be associated with a variety of other pathological conditions, including AIDS, Alzheimer's disease, Parkinson's disease, amyotrophic lateral sclerosis, multiple sclerosis, retinitis pigmentosa, cerebella degeneration, aplastic anemia, myocardial infarction, stroke, reperfusion injury, and toxin-induced liver disease (see, Thompson, Supra).

Apoptotic cell death is typically accompanied by one or more characteristic morphological and biochemical changes in cells, such as condensation of cytoplasm, loss of plasma membrane microvilli, segmentation of the nucleus, degradation of chromosomal DNA or loss of mitochondrial function. A recognized biochemical marker of apoptosis is the cleavage of chromatin into nucleosomal fragments.

A variety of extrinsic and intrinsic signals are believed to trigger or induce such morphological and biochemical cellular changes (Raff, *Nature*, 356:397400 (1992); Steller, Supra; Sachs, et al.,*Blood,* 82:15 (1993)). For instance, they can be triggered by hormonal stimuli, such as glucocorticoid hormones for immature thymocytes, as well as withdrawal of certain growth factors (Watanabe-Fukunaga, et al., *Nature*, 356:314–317 (1992)). Also, some identified oncogenes such as myc, rel, and EIA, and tumor suppressers, like p53, have been reported to have a role in inducing apoptosis, Certain chemotherapy drugs and some forms of radiation have likewise been observed to have apoptosis-inducing activity (Thompson, Supra). Apoptosis is also triggered by the activation of a family of cysteine proteases having specificity for aspartic acid residues, including Ced-3 of *C. elegans,* CCP32 (now caspase-3), Yama/Apopain of humans, and DCP-1 of Drosophila. These proteases are designated as caspases (Alnemri, et al., *Cell,* 87:171, (1996)).

The Apoptosis-Inducing Signaling Complex

As presently understood, the apoptosis program contains at least three important elements—activators, inhibitors, and effectors. In *C. elegans,* these elements are encoded respectively by three genes, Ced-4, Ced-9 and Ced-3 (Steller, *Science,* 267:1445 (1995); Chinnaiyan, et al., *Science.* 275:1122–1126 (1997)). Two genes, Ced-3 and Ced-4, are required to initiate apoptosis (Yuan and Horvitz, *Development* 116:309–320, (1990)), Ced-9, which functions upstream of Ced-3 and Ced4, negatively regulates the apoptotic program by preventing activation of Ced-3 and Ced4 (Hengartner, et al., *Cell* 76:665–676 (1994)).

The apoptotic program delineated in *C. elegans* is conserved in mammalian cells which contain homologues of Ced-9 and Ced-3. One of these homologues, Bcl-2. can partially substitute for Ced-9 in preventing apoptosis in *C. elegans* (Hengartner and Horvitz, 1994, *Cell* 76:665–676). The other homologues are cysteine proteases that are closely related to Ced-3, including caspase-3 (Yuan, et al., *Cell* 75:641–652 (1993): Xue, et al., *Genes & Dev.* 10:1073–1083 (1996)). Ced-4 is the only remaining *C. elegans* general apoptosis gene of which the mammalian counterpart had not been found. This gene is believed to function downstream of Ced-9 but upstream of Ced-3 in the *C. elegans* apoptosis pathway (Shaham and Horvitz, *Genes & Dev.* 10:578–591, (1996), *Cell* 86:201–208 (1996)).

In mammalian cells, caspase-3 normally exists in the cytosolic fraction as a 32 kDa inactive precursor which is converted proteolytically to a 20 kDa and a 10 kDa active heterodimer when cells are signaled to die (Schlegel, et al., *Bio. Chem.* 271:1841–1844, (1996); Wang, et al., *EMBO J.* 15:1012–1020, (1996)). Bcl-2, located on the outer membrane of mitochondria, prevents the activation of caspase-3. It appears to do this by blocking the mitochondria from releasing cytochrome c, a necessary co-factor for caspase-3 activation (Liu, et al., *Cell* 86:147–157, (1996); Yang, et al., *Science* 275:1129–1132, (1997); Kluck, et al., *Science* 275:1132–1136, (1997)). Deletion of caspase-3 from the mouse genome through homologous recombination results in excessive accumulation of neuronal cells, due to a lack of apoptosis in the brain (Kuida, et al., *Nature* 384:368–372 (1996),. Addition of active caspase-3 to normal cytosol activates the apoptotic program (Enari, et al., *Nature* 380:723–726 (1996)). Thus, caspase-3 is both necessary and sufficient to trigger apoptosis.

Identified substrates for caspase-3 include poly (ADP-ribose) polymerase (PARP), sterol-regulatory element binding proteins (SREBPs), the U1-associated 70 kDa protein, N4-GD1, huntingtin and DNA dependent protein kinase (Casicola-Rosen, et al.,*J. Exp. Med* 183:1957–1964 (1996); Na. et al., *J. Biol. Chem.* 271:11209–11213 (1996); Goldberg, et al., *Nat. Genet.* 13(4):442–449 (1996); Wang, et al. *EMBO J.* 15:1012–1020 (1996); Nicholson, et al., *Nature* 376:37–43, (1995)).

Applicants recently established an in vitro apoptosis system to study apoptosis using cytosolic fractions from normally growing HeLa cells. Using this system, two protein factors involved in mammalian apoptosis were identified: cytochrome c (Liu. et al., 1996, Supra) and DNA fragmentation factor (DFF), a novel heterodimer of 45 kDa and 40 kDa subunits, DFF functions downstream of caspase-3 to trigger fragmentation of genomic DNA into nucleosomal segments, a hallmark of apoptosis (Wyllie, *Nature* 284:555–556, (1980); Liu. et al., 1997 Supra).

SUMMARY OF THE INVENTION

Applicants have identified a DNA sequence (SEQ ID NO:1) that encodes a novel protein (SEQ ID NO:2), designated in the present application as "Apaf-1." It is believed that Apaf-1 is a mammalian homologue of Ced-4. The native sequence of human Apaf-1 is a novel 130 kDa polypeptide containing a Ced-3 homologous domain at the N-terminus, followed by a Ced-4 homologous domain and multiple WD40 repeats at the C-terminus. It has been found that Apaf-1 can form a complex with cytochrome-c, and activates caspase-3 in the apoptotic pathway.

An alternatively spliced transcript, Apaf-1L has also been discovered. Its novel nucleic acid sequence (SEQ ID NO:15) and encoded protein (SEQ ID NO:16) have similar activities and, for purposes of the invention, included within the invention as an optional Apaf-1 polypeptide.

The invention provides isolated Apaf-1 protein. In particular, the invention provides an isolated native sequence Apaf-1 protein, which includes an amino acid sequence comprising residues 1 to 1194 of FIGS. 5A–5O and FIG. 6 (SEQ ID NO:2). In other embodiments, the isolated Apaf-1 protein comprises at least about 80% amino acid sequence identity with native sequence Apaf-1 protein comprising residues 1 to 1194 of FIGS. 5A–5O and FIG. 6 (SEQ ID NO:2).

In another embodiment, the invention provides an isolated nucleic acid molecule encoding Apaf-1 protein (SEQ ID NO:1). The nucleic acid molecule is an RNA or DNA encoding an Apaf-1 protein or a particular domain of Apaf-1, such as a cytochrome c binding domain or an ATP binding domain, or is complementary to such encoding nucleic acid sequence, and remains stably bound to it under at least moderate, and optionally, under high stringency conditions. In one embodiment, the nucleic acid sequence is selected from:
(a) the coding region of the nucleic acid sequence of FIGS. 5A–5O (SEQ ID NO:1) that codes for amino acid residues 1 to 1194 (i.e., nucleotides 578 through 4159), inclusive;
(b) the enlarged cDNA sequence of FIGS. 5A–5O (SEQ ID NO:1) encoding amino acids 1 to 1194, and including further nucleic acids positioned 5' of the translation initiation site and/or 3' of the stop codon sequences (i.e.; nucleotides 1 to 7042);
(c) the coding region of the nucleic acid sequence of FIGS. 16A–16H (SEQ ID NO:15) that codes for amino acid residues 1 to 1205 (i.e., nucleotides 578 through 4192), inclusive;
(d) the enlarged cDNA sequence of FIGS. 16A–16H (SEQ ID NO:15) encoding amino acids 1 to 1205, and including further nucleic acids positioned 5' of the translation initiation site and/or 3' of the stop codon sequences (i.e.; nucleotides 1 to 7075); and
(e) a sequence corresponding to the sequence of (a), (b), (c), or (d) and is within the scope of degeneracy of the genetic code.

In a further embodiment, the invention provides a vector comprising the nucleic acid molecule encoding the Apaf-1 protein or particular domain of Apaf-1. A host cell comprising the vector or the nucleic acid molecule is also provided. A method of producing Apaf-1 is further provided.

In a further embodiment, the invention provides vectors and gene constructs comprising a nucleic acid sequence encoding Apaf-1 or a portion thereof In another embodiment, the invention provides an antibody which specifically binds to Apaf-1. The antibody may be an agonistic, antagonistic or neutralizing antibody.

A further embodiment of the invention provides articles of manufacture and kits that include Apaf-1 protein, nucleic acid sequences encoding Apaf-1, or anti-Apaf-1 antibodies.

The novel gene, protein, and antibodies of the invention are particularly useful for screening and identifying cells signaled for apoptosis. In addition, the gene and protein of the invention are particularly useful for screening of candidate compounds to identify agents useful in modulating apoptosis.

BRIEF DESCRIPTION OF THE DRAWINGS

FIG. 4 shows Apaf-1 protein of the column fractions described for FIG. 3 in a silverstained PAGE gel (8%), having a molecular weight of approximately 130 kDa.

FIGS. 5A–5G shows the DNA sequence and deduced amino acid sequence of human Apaf-1.

FIG. 6 shows the protein sequence of Apaf-1. Previously sequenced 14 tryptic and Lys-C peptides (Table-1) are underlined. The putative WD-repeats are boxed.

FIG. 8 shows those amino acid sequences of Apaf-1 that share homology with the N-terminal pro-domain of Ced-3 (Yuan, et al., Supra (1993)). Identical amino acids are shown in bold. Conserved amino acids are boxed.

FIG. 9 shows those amino acid sequence of Apaf-1 that share homology with amino acids of Ced4 (Yuan and Horvitz, Supra (1992)).

FIGS. 16A–16H show the nucleic acid sequence encoding Apaf-1L. The additional 33 nucleic acids as compared with Apaf-1 are underlined.

FIG. 17 shows the amino acid sequence of Apaf-1L. The additional 11 amino acids are underlined.

DETAILED DESCRIPTION OF THE PREFERRED EMBODIMENTS

I. Definitions

Figure 1:
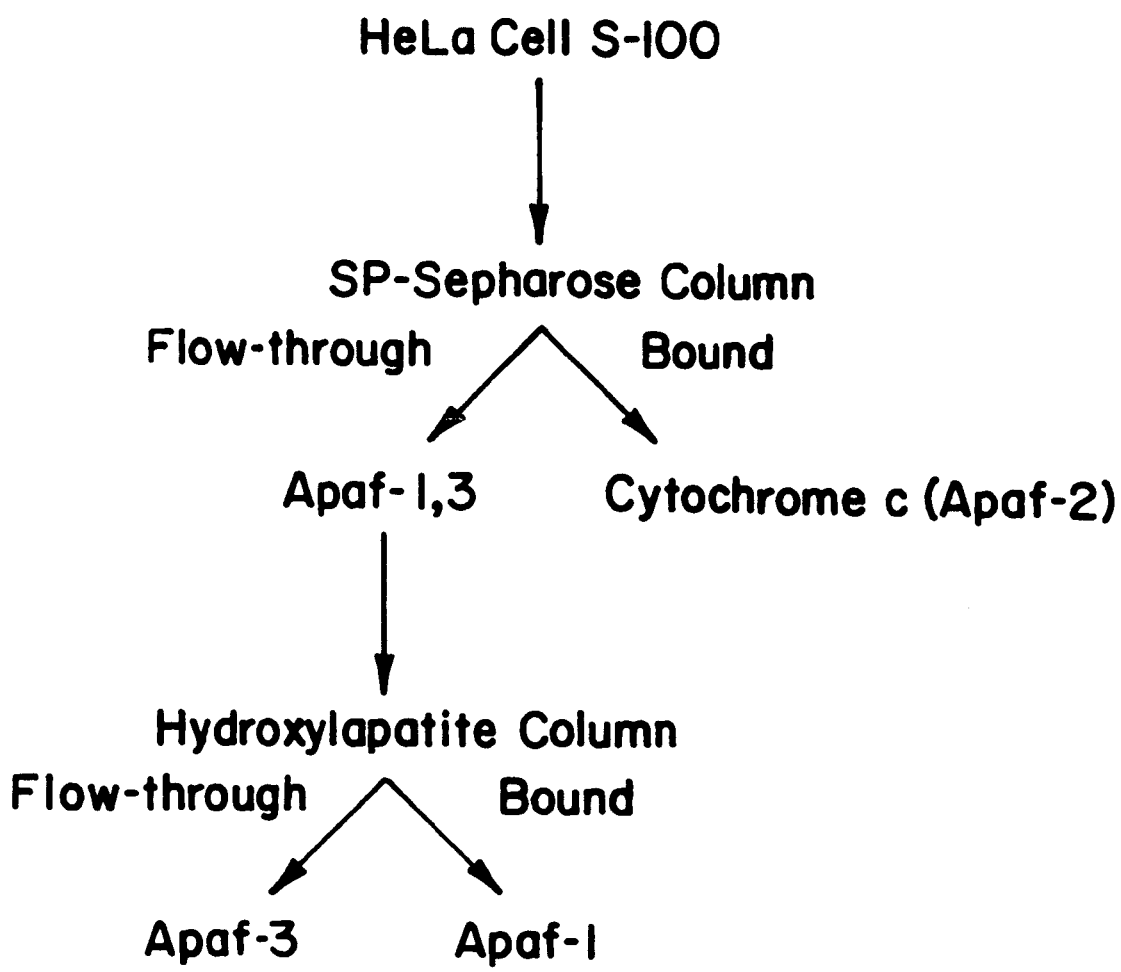
FIG. 1 shows a schematic outline of the purification procedure leading to the purification of Apaf-1.

The terms "Apaf-1 protein" and "Apaf-1" when used herein encompass native sequence Apaf-1, alternative splice variants such as Apaf-1L (described more fully in the Examples below), and other Apaf-1 variants (which are further defined herein). These terms encompass Apaf-1 from a variety of mammals, including humans. The Apaf-1 may be isolated from a variety of sources, such as from human tissue types or from another source, or prepared by recombinant or synthetic methods.

A "native sequence Apaf-1" comprises a polypeptide having the same amino acid sequence as an Apaf-1 derived from nature. Thus, a native sequence Apaf-1 can have the amino acid sequence of naturally-occurring Apaf-1 from any mammal. Such native sequence Apaf-1 can be isolated from nature or can be produced by recombinant or synthetic means. The term "native sequence Apaf-1" specifically encompasses naturally-occurring truncated or secreted forms of the Apaf-1, naturally-occurring variant forms (e.g., alternatively spliced forms), and naturally-occurring allelic variants of the Apaf-1.

"Apaf-1 variant" means a biologically active Apaf-1 as defined below having at least about 80% amino acid sequence identity with the Apaf-1 having the deduced amino acid sequence shown in FIGS. 5A–5G (SEQ ID NO:2) or in FIG. 17 (SEQ ID NO:16). Such Apaf-1 variants include, for instance, Apaf-1 proteins wherein one or more amino acid residues are added or deleted at the N- or C-terminus of the sequence of FIGS. 5A–5O (SEQ ID NO:2) or in FIG. 17 (SEQ ID NO:16). Ordinarily, an Apaf-1 variant will have at least about 80% amino acid sequence identity, more preferably at least about 90% amino acid sequence identity, and even more preferably at least about 95% amino acid sequence identity with the amino acid sequence of FIGS. 5A–5O (SEQ ID NO:2) or in FIG. 17 (SEQ ID NO:16).

"Percent (%) amino acid sequence identity" with respect to the Apaf-1 sequences identified herein is defined as the percentage of amino acid residues in a candidate sequence that are identical with the amino acid residues in the Apaf-1 sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as ALIGN™ or Megalign (DNASTAR) software. Those skilled in the art can determine appropriate parameters for measuring alignment, including any algorithms needed to achieve maximal alignment over the full length of the sequences being compared.

The term "epitope tagged" when used herein refers to a chimeric polypeptide comprising Apaf-1, or a domain sequence thereof, fused to a "tag polypeptide". The tag polypeptide has enough residues to provide an epitope against which an antibody can be made, yet is short enough such that it does not interfere with activity of the Apaf-1. The tag polypeptide preferably also is fairly unique so that the antibody does not substantially cross-react with other epitopes. Suitable tag polypeptides generally have at least six amino acid residues and usually between about 8 to about 50 amino acid residues (preferably, between about 10 to about 20 residues).

"Isolated", when used to describe the protein disclosed herein, means a polypeptide or protein that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the Apaf-1 natural environment will not be present. Ordinarily, however, isolated polypeptide will be prepared by at least one purification step.

An "isolated" Apaf-1 nucleic acid molecule is a nucleic acid molecule that is identified and separated from at least one contaminant nucleic acid molecule with which it is ordinarily associated in the natural source of the Apaf-1 nucleic acid. An isolated Apaf-1 nucleic acid molecule is other than in the form or setting in which it is found in nature. Isolated Apaf-1 nucleic acid molecules therefore are distinguished from the Apaf-1 nucleic acid molecule as it exists in natural cells. However, an isolated Apaf-1 nucleic acid molecule includes Apaf-1 nucleic acid molecules contained in cells that ordinarily express Apaf-1 where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adapters or linkers are used in accordance with conventional practice.

The term "antibody" is used in the broadest sense and specifically covers single anti-Apaf-1 monoclonal antibodies (including agonist, antagonist, and neutralizing antibodies) and anti-Apaf-1 antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-Apaf-1 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. See, e.g. U.S. Pat. No. 4,816,567 and Mage et al., in *Monoclonal Antibody Production Techniques and Applications*, pp. 79–97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature*, 256:495 (1975), or may be made by recombinant DNA methods such as described in U.S. Pat. No. 4,816,567. The "monoclonal antibodies" may also be isolated from phage libraries generated using the techniques described in McCafferty, et al., *Nature*, 348:552–554 (1990), for example.

"Humanized" forms of non-human (e.g. murine) antibodies are specific chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin.

"Biologically active" and "desired biological activity" for the purposes herein mean having the ability to modulate apoptosis (in an agonistic or stimulating manner) in at least one type of mammalian cell in vivo or ex vivo or in the cell-free assay system described herein. In particular, the biological activity of Apaf-1 is the activation of caspase-3 to trigger apoptotic events.

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays, FACS analysis or DNA electrophoresis, all of which are known in the art. In particular, apoptosis can be measured in the cell free system described in the examples below and in Liu, et al., Supra.

The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

II. Compositions and Methods of the Invention

The present invention provides a newly identified and isolated Apaf-1 protein. In particular, Applicants have identified and isolated a human Apaf-1 protein. The properties and characteristics of this Apaf-1 protein are described in further detail in the Examples below. Based upon the properties and characteristics of the Apaf-1 protein disclosed herein, it is Applicants' present belief that Apaf-1 is a mammalian homologue of Ced-4.

A. Apaf-1 is a Mammalian Homologue of Ced-4

Several lines of evidence suggest that Apaf-1 is the mammalian homologue of Ced4. First, Apaf-1 shows significant sequence homology with Ced4 over more than 300 amino acids; second, several important regions of Ced4, including conserved nucleotide binding regions, and an isoleucine at position 258, are conserved in Apaf-1 (FIG. 8); third, the biochemical function of Apaf-1, which is to mediate the activation of caspase-3, is consistent with the function of Ced4 as delineated by genetic studies. The genetic studies indicate that Ced-4 functions downstream of Ced-9, but upstream of Ced-3, since the killing of the *C. elegans* ALM neurons by overexpression of Ced-4 is greatly reduced in Ced-3 mutant, whereas killing of these neurons by overexpression of Ced-3 is unaffected by mutations in Ced-4 (Hengartner, et al., Supra; Shaham and Horvitz, Supra). Similarly, bcl-2 functions upstream of Apaf-1 by controlling the release of cytochrome c, a co-factor for Apaf-1 activity (Kluck, et al., Supra; Yang, et al., Supra).

B. Mechanism for Triggering Caspase-3 Activation

Apaf-1 itself does not appear to be a caspase. The conserved active site pentapeptide QACR (or Q/G)G that is present in all identified caspases is not present in Apaf-1. Most of the WD repeat-containing proteins are regulatory in function rather than enzymatic (Neer, et al., 1994, *Nature* 371:297–300). The identification of the regions that are conserved among proteins that utilize ATP is consistent with the requirement of dATP in the caspase-3 activation reaction. In this case, dATP is preferred over ATP.

Apaf-1 appears to be a key factor in the initiation of apoptosis. Apaf-1 binds cytochrome c and dATP, both important factors in triggering apoptosis. Together, Apaf-1, cytochrome c. dATP and Apaf-3 form a unique model system for apoptosis, in a cell-free system or within cells and tissues.

A description follows as to how Apaf-1, as well as Apaf-1 chimeric molecules and anti-Apaf-1 antibodies, may be prepared.

C. Preparation of Apaf-1

The description below relates primarily to production of Apaf-1 by culturing cells transformed or transfected with a vector containing Apaf-1 nucleic acid. It is of course, contemplated that alternative methods, which are well known in the art, may be employed to prepare Apaf-1.

1. Isolation of DNA Encoding Apaf-1

The DNA encoding Apaf-1 may be obtained from any cDNA library prepared from tissue believed to possess the Apaf-1 mRNA and to express it at a detectable level. Accordingly, human Apaf-1 DNA can be conveniently obtained from a cDNA library prepared from human tissues, such as the libraries of human HeLa cell cDNA described in Example 2, and others, particularly DNA libraries produced from tissues known for high apoptotic activity such as spleen, fetal brain, and the like. Such DNA libraries are commercially available, e.g. from CloneTech and Stratagene. The Apaf-1-encoding gene may also be obtained from a genomic library or by oligonucleotide synthesis.

Libraries can be screened with probes (such as antibodies to the Apaf-1 or oligonucleotides of at least about 20–80 bases) designed to identify the gene of interest or the protein encoded by it. Screening the cDNA or genomic library, with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding Apaf-1 is to use PCR methodology (Sambrook. et al., Supra; Dieffenbach, et al., *PCR Primer:A Laboratory Manual* (Cold Spring Harbor Laboratory Press, 1995)).

A preferred method of screening employs selected oligonucleotide sequences to screen cDNA libraries from various human tissues. Example 2 below describes techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook, et al., Supra.

Nucleic acid having all the protein coding sequence may be obtained by screening selected cDNA or genomic libraries using the deduced amino acid sequence disclosed herein for the first time, and, if necessary, using conventional primer extension procedures as described in Sambrook, et al., Supra, to detect precursors and processing intermediates of mRNA that may not have been reverse-transcribed into cDNA.

Apaf-1 variants can be prepared by introducing appropriate nucleotide changes into the Apaf-1 DNA, or by synthesis of the desired Apaf-1 polypeptide. Those skilled in the art will appreciate that amino acid changes may alter post-translational processes of the Apaf-1, such as changing the number or position of glycosylation sites or altering the membrane anchoring characteristics.

Variations in the native full-length sequence Apaf-1 or in various domains of the Apaf-1 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the Apaf-1 that results in a change in the amino acid sequence of the Apaf-1 as compared with the native sequence Apaf-1. Optionally the variation is by substitution of at least one amino acid with any other amino acid in one or more of the domains of the Apaf-1 molecule. The variations can be made using methods known in the art such as oligonucleotide-mediated (site-directed) mutagenesis, alanine scanning, and PCR mutagenesis. Site-directed mutagenesis (Carter, et al., *Nucl. Acids Res.,* 13:4331 (1986): Zoller, et al., *Nucl. Acids Res.,* 10:6487 (1987)) cassette mutagenesis (Wells, et al., *Gene.* 34:315 (1985)), restriction selection mutagenesis (Wells, et al., *Philos. Trans. R. Soc. London SerA,* 317:415 (1986)) or other known techniques can be performed on the cloned DNA to produce the Apaf-1 variant DNA.

Scanning amino acid analysis can also be employed to identify one or more amino acids along a contiguous sequence which are involved in the interaction with a particular ligand or receptor. Among the preferred scanning amino acids are relatively small, neutral amino acids. Such amino acids include alanine, glycine, serine, and cysteine. Alanine is the preferred scanning amino acid among this group because it eliminates the side-chain beyond the beta-carbon and is less likely to alter the main-chain conformation of the variant. Alanine is also preferred because it is the most common amino acid. Further, it is frequently found in both buried and exposed positions (Creighton, *The Proteins,* (W. H. Freeman & Co., N.Y.); Chothia, *J. Mol. Biol.,* 150:1 (1976)). If alanine substitution does not yield adequate amounts of variant, an isoteric amino acid can be used.

Once selected Apaf-1 variants are produced, they can be screened, for example, by their activity in the activation of caspase-3, for example, in the cell free assay described herein and as described in Example 3 below.

2. Insertion of Nucleic Acid into A Replicable Vector

The nucleic acid (e.g. cDNA or genomic DNA) encoding Apaf-1 may be inserted into a replicable vector for further cloning (amplification of the DNA) or for expression. Various vectors are publicly available. The vector components generally include, but are not limited to, one or more of the following: a signal sequence, an origin of replication, one or more marker genes, an enhancer element, a promoter, and a transcription termination sequence, each of which is described below.

(i) Signal Sequence Component

The Apaf-1 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the Apaf-1 DNA that is inserted into the vector. The heterologous signal sequence selected preferably is one that is recognized and processed (i.e., cleaved by a signal peptidase) by the host cell. The signal sequence may be a prokaryotic signal sequence selected for example, from the group of the alkaline phosphatase, penicillinase, 1pp. or heat-stable enterotoxin 11 leaders. For yeast secretion the signal sequence may be, e.g., the yeast invertase leader, alpha factor leader (including Saccharomyces and Kluyveromyces -factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published Nov. 15, 1990. In mammalian cell expression the native Apaf-1 presequence that normally directs insertion of Apaf-1 in the cell membrane of human cells in vivo is satisfactory, although other mammalian signal sequences may be used to direct secretion of the protein, such as signal sequences from secreted polypeptides of the same or related species, as well as viral secretory leaders, for example, the herpes simplex glycoprotein D signal.

The DNA for such precursor region is preferably ligated in reading frame to DNA encoding Apaf-1.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the $2\mu$ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of Apaf-1 DNA. However, the recovery of genomic DNA encoding Apaf-1 is more complex than that of an exogenously replicated vector because restriction enzyme digestion is required to excise the Apaf-1 DNA.

(iii) Selection Gene Component

Expression and cloning vectors typically contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin (Southern, et al., *J. Molec. Appl. Genet.,* 1:327 (1982)), mycophenolic acid (Mulligan, et al., *Science,* 209:1422 (1980)) or hygromycin (Sugden, et al., *Mol. Cell. Biol.,* 5:410–413 (1985)). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the Apaf-1 nucleic acid such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes Apaf-1. Amplification is the process by which genes in greater demand for the production of a protein critical for growth are reiterated in tandem within the chromosomes of successive generations of recombinant cells. Increased quantities of Apaf-1 are synthesized from the amplified DNA. Other examples of amplifiable genes include metallothionein-I and -II, adenosine deaminase, and ornithine decarboxylase.

Cells transformed with the DHFR selection gene may first be identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub, et al., *Proc. Natl. Acad. Sci. USA,* 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding Apaf-1. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding Apaf-1, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb, et al., *Nature.* 282:39 (1979); Kingsman, et al., *Gene,* 7:141 (1979); Tschemper, et al., *Gene,* 10:157(1980)). The trp1 gene provides a selection marker for a mutant strain of yeast lacking the ability to grow in tryptophan, for example, ATCC No. 44076 or PEP4-1 (Jones, *Genetics,* 85:12 (1977)). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 $\mu$m circular plasmid pKD1 can be used for transformation of Kluyveromyces yeasts (Bianchi, et al., *Curr. Genet.,* 12:185 (1987)). More recently, an expression system for large-scale production of recombinant calf chymosin was reported for *K. lactis* (Van den Berg, *Bio/Technology,* 8:135 (1990)). Stable multi-copy expression vectors for secretion of mature recombinant human serum albumin by industrial strains of Kluyveromyces have also been disclosed (Fleer, et al., *Bio/Technology,* 9:968–975 (1991)).

(iv) Promoter Component

Expression and cloning vectors usually contain a promoter that is recognized by the host organism and is operably linked to the Apaf-1 nucleic acid sequence. Promoters are untranslated sequences located upstream (5') to the start codon of a structural gene (generally within about 100 to 1000 bp) that control the transcription and translation of particular nucleic acid sequence, such as the Apaf-1 nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to Apaf-1 encoding DNA by removing the promoter from the source DNA by restriction enzyme digestion and inserting the isolated promoter sequence into the vector. Both the native Apaf-1 promoter sequence and many heterologous promoters may be used to direct amplification and/or expression of the Apaf-1 DNA.

Promoters suitable for use with prokaryotic hosts include the β-lactamase 25 and lactose promoter systems (Chang. et al., *Nature*, 275:615 (1978): Goeddel, et al., *Nature*, 281:544 (1979)), alkaline phosphatase, a tryptophan (trp) promoter system (Goeddel. *Nucleic Acids Res.*, 8:4057 (1980); EP 36,776), and hybrid promoters such as the tac promoter (deBoer, et al., *Proc. Natl. Acad. Sci. USA*, 80:21–25 (1983)). However, other known bacterial promoters are suitable. Their nucleotide sequences have been published, thereby enabling a skilled worker operably to ligate them to DNA encoding Apaf-1 (Siebenlist, et al., *Cell*, 20:269 (1980)) using linkers or adapters to supply any required restriction sites. Promoters for use in bacterial systems also will contain a Shine-Dalgarno (S.D.) sequence operably linked to the DNA encoding Apaf-1.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman, et al., *J. Biol. Chem.*, 255:2073 (1980)) or other glycolytic enzymes (Hess, et al., *J. Adv. Enzyme Reg.*, 7:149 (1968); Holland, *Biochemistry*, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Apaf-1 transcription from vectors in mammalian host cells is controlled, for example, by promoters obtained from the genomes of viruses such as polyoma virus. fowlpox virus (UK 2,211,504 published Jul. 5, 1989), adenovirus (such as Adenovirus 2). bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the Apaf-1 sequence, provided such promoters are compatible with the host cell systems.

The early and late promoters of the SV40 virus are conveniently obtained as an SV40 restriction fragment that also contains the SV40 viral origin of replication (Fiers, et al., *Nature*, 273:113 (1978); Mulligan and Berg, *Science*, 209:1422–1427 (1980); Pavlakis, et al., *Proc. Natl. Acad. Sci. USA*, 78:7398–7402 (1981)). The immediate early promoter of the human cytomegalovirus is conveniently obtained as a HindIII E restriction fragment (Greenaway, et al., *Gene*, 18:355–360 (1982)). A system for expressing DNA in mammalian hosts using the bovine papilloma virus as a vector is disclosed in U.S. Pat. No. 4,419,446. A modification of this system is described in U.S. Pat. No. 4,601,978 (See also Gray, et al., *Nature*, 295:503–508 (1982) on expressing cDNA encoding immune interferon in monkey cells; Reyes, et al., *Nature*, 297:598–601 (1982) on expression of human γ-interferon cDNA in mouse cells under the control of a thymidine kinase promoter from herpes simplex virus; Canaani and Berg, *Proc. Natl. Acad. Sci. USA* 79:5166–5170 (1982) on expression of the human interferon 1 gene in cultured mouse and rabbit cells; and Gorman, et al., *Proc. Natl. Acad. Sci. USA*, 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter).

(v) Enhancer Element Component

Transcription of a DNA encoding the Apaf-1 of this invention by higher eukaryotes may be increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins, et al., *Proc. Natl. Acad Sci. USA*, 78:993 (1981) and 3' (Lusky, et al., *Mol. Cell Bio.*, 3:1108 (1983) to the transcription unit, within an intron (Banerj, et al., *Cell*, 33:729 (1983)), as well as within the coding sequence itself (Osborne, et al., *Mol. Cell Bio.*, 4:1293 (1984)). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297:17–18 (1982) on enhancing elements for activation of eukaryotic promoters. The enhancer may be spliced into the vector at a position 5' or 3' to the Apaf-1 coding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding Apaf-1.

(vii) Construction and Analysis of Vectors

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures can be used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing, et al., *Nucleic Acids Res.,* 9:309 (1981) or by the method of Maxam, et al., *Methods in Enzymology,* 65:499 (1980).

(viii) Transient Expression Vectors

Expression vectors that provide for the transient expression in mammalian cells of DNA encoding Apaf-1 may be employed. In general, transient expression involves the use of an expression vector that is able to replicate efficiently in a host cell such that the host cell accumulates many copies of the expression vector and, in turn, synthesizes high levels of a desired polypeptide encoded by the expression vector (Sambrook et al., supra). Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying Apaf-1 variants.

(ix) Suitable Exemplary Vertebrate Cell Vectors

Other methods, vectors, and host cells suitable for adaptation to the synthesis of Apaf-1 in recombinant vertebrate cell culture are described in Gething et al., *Nature,* 293:620–625 (1981); Mantei et al., *Nature,* 281:4046 (1979); EP 117,060; and EP 117,058.

3. Selection and Transformation of Host Cells

Suitable host cells for cloning or expressing the DNA in the vectors herein are the prokaryote, yeast, or higher eukaryote cells described above. Suitable prokaryotes for this purpose include but are not limited to eubacteria, such as Gram-negative or Gram-positive organisms, for example, Enterobacteriaceae such as Escherichia, e.g., *E. coli,* Enterobacter, Erwinia, Klebsiella, Proteus, Salmonella, e.g., *Salmonella typhimurium,* Serratia, e.g., *Serratia marcescans,* and Shigella, as well as Bacilli such as *B. subtilis* and *B. licheniformis* (e.g., *B. licheniformis* 41P disclosed in DD 266,710 published Apr. 12, 1989). Pseudomonas such as *P. aeruginosa,* and Streptomyces. Preferably, the host cell should secrete minimal amounts of proteolytic enzymes.

In addition to prokaryotes, eukaryotic microbes such as filamentous fungi or yeast are suitable cloning or expression hosts for Apaf-1-encoding vectors. *Saccharomyces cerevisiae,* or common baker's yeast, is the most commonly used among lower eukaryotic host microorganisms. However, a number of other genera, species, and strains are commonly available and useful herein.

Suitable host cells for the expression of glycosylated Apaf-1 are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified (See, e.g., Luckow, et al., *Bio/Technology,* 6:47–55 (1988); Miller, et al., in *Genetic Engineering,* Setlow, et al., eds., Vol. 8 (Plenum Publishing, 1986), pp. 277–279; and Maeda, et al., *Nature,* 315:592–594 (1985)). A variety of viral strains for transfection are publicly available, e.g., the L-1 variant of *Autographa californica* NPV and the Bm-5 strain of *Bombyx mori* NPV.

Plant cell cultures of cotton, corn, potato, soybean, petunia, tomato, and tobacco can be utilized as hosts. Typically, plant cells are transfected by incubation with certain strains of the bacterium *Agrobacterium tumefaciens.* During incubation of the plant cell culture with *A. tumefaciens,* the DNA encoding the Apaf-1 can be transferred to the plant cell host such that it is transfected, and will, under appropriate conditions, express the Apaf-1 -encoding DNA. In addition, regulatory and signal sequences compatible with plant cells are available, such as the nopaline synthase promoter and polyadenylation signal sequences (Depicker, et al., *J. Mol. Appl. Gen.,* 1:561 (1982)). In addition, DNA segments isolated from the upstream region of the T-DNA 780 gene are capable of activating or increasing transcription levels of plant-expressible genes in recombinant DNA-containing plant tissue (EP 321,196 published Jun. 21, 1989).

Propagation of vertebrate cells in culture (tissue culture) is also well known in the art (See, e.g., *Tissue Culture,* Academic Press. Kruse and Patterson, editors (1973)). Examples of useful mammalian host cell lines are monkey kidney CV1 line transformed by SV40 (COS-7, ATCC CRL 1651); human embryonic kidney line (293 or 293 cells subcloned for growth in suspension culture, Graham, et al., *J. Gen Virol.,* 36:59 (1977)); baby hamster kidney cells (BHK, ATCC CCL 10); Chinese hamster ovary cells/DHFR (CHO, Urlaub and Chasin, *Proc. Natl. Acad. Sci. USA,* 77:4216 (1980)); mouse sertoli cells (TM4, Mather, *Biol. Reprod.,* 23:243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather, et al., *Annals N.Y Acad. Sci.,* 383:44–68 (1982)); MRC 5 cells; and FS4 cells.

Host cells are transfected and preferably transformed with the above-described expression or cloning vectors for Apaf-1 production and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integration. Depending on the host cell used, transformation is done using standard techniques appropriate to such cells. The calcium treatment employing calcium chloride, as described in Sambrook. et al., Supra, or electroporation is generally used for prokaryotes or other cells that contain substantial cell-wall barriers. Infection with *Agrobacterium tumefaciens* is used for transformation of certain plant cells, as described by Shaw, et al., *Gene,* 23:315 (1983) and WO 89/05859 published Jun. 29, 1989. In addition, plants may be transfected using ultrasound treatment as described in WO 91/00358 published Jan. 10, 1991.

For mammalian cells without such cell walls, the calcium phosphate precipitation method of Graham and van der Eb, *Virology,* 52:456–457 (1978) is preferred. General aspects of mammalian cell host system transformations have been described in U.S. Pat. No. 4,399,216. Transformations into yeast are typically carried out according to the method of Van Solingen. et al., *J. Bact.,* 130:946 (1977) and Hsiao, et al., *Proc. Natl. Acad. Sci. (USA),* 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown, et al., *Methods in Enzymology,* 185:527–537 (1990) and Mansour, et al., *Nature,* 336:348–352 (1988).

4. Culturing the Host Cells

Prokaryotic cells used to produce Apaf-1 may be cultured in suitable media as described generally in Sambrook, et al., Supra.

The mammalian host cells used to produce Apaf-1 may be cultured in a variety of media. Examples of commercially available media include Ham's F10 (Sigma), Minimal Essential Medium ("MEM", Sigma), RPMI-1640 (Sigma), and Dulbecco's Modified Eagle's Medium ("DMEM", Sigma). Any such media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach,* M. Butler, ed. (IRL Press, 1991).

The host cells referred to in this disclosure encompass cells in culture as well as cells that are within a host animal.

5. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA.* 77:5201–5205 (1980)), dot blotting (DNA analysis), or in situ hybridization, using an appropriately labeled probe, based on the sequences provided herein. Various labels may be employed, most commonly radioisotopes, and particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionucleotides, fluorescers or enzymes. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, or luminescent labels.

Antibodies useful for immunohistochemical staining and/or assay of sample fluids may be either monoclonal or polyclonal, and may be prepared in any mammal. Conveniently, the antibodies may be prepared against a native sequence Apaf-1 polypeptide or against a synthetic peptide based on the DNA sequences provided herein or against exogenous sequence fused to Apaf-1 DNA and encoding a specific antibody epitope.

6. Purification of Apaf-1 Polypeptide

Forms of Apaf-1 may be recovered from culture medium or from host cell lysates. If the Apaf-1 is membrane-bound, it can be released from the membrane using a suitable detergent solution (e.g. Triton-X 100) or its extracellular domain may be released by enzymatic cleavage.

When Apaf-1 is produced in a recombinant cell other than one of human origin, the Apaf-1 is free of proteins or polypeptides of human origin. However, it may be desired to purify Apaf-1 from recombinant cell proteins or polypeptides to obtain preparations that are substantially homogeneous as to Apaf-1. As a first step, the culture medium or lysate may be centrifuged to remove particulate cell debris. Apaf-1 thereafter is purified from contaminant soluble proteins and polypeptides, with the following procedures being exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG.

Apaf-1 variants in which residues have been deleted, inserted, or substituted can be recovered in the same fashion as native sequence Apaf-1, taking account of changes in properties occasioned by the variation. For example, preparation of an Apaf-1 fusion with another protein or polypeptide, e.g., a bacterial or viral antigen, immunoglobulin sequence, or receptor sequence, may facilitate purification; an immunoaffinity column containing antibody to the sequence can be used to adsorb the fusion polypeptide. Other types of affinity matrices also can be used.

A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native sequence Apaf-1 may require modification to account for changes in the character of Apaf-1 or its variants upon expression in recombinant cell culture.

7. Covalent Modifications of Apaf-1 Polypeptides

Covalent modifications of Apaf-1 are included within the scope of this invention. One type of covalent modification of the Apaf-1 is introduced into the molecule by reacting targeted amino acid residues of the Apaf-1 with an organic derivatizing agent that is capable of reacting with selected side chains or the N- or C-terminal residues of the Apaf-1.

Derivatization with bifunctional agents is useful for cross-linking Apaf-1 to a water-insoluble support matrix or surface for use in the method for purifying anti-Apaf-1 antibodies, and vice-versa. Derivatization with one or more bifunctional agents will also be useful for cross-linking Apaf-1 molecules to generate Apaf-1 dimers. Such dimers may increase binding avidity and extend half-life of the molecule in vivo. Commonly used cross-linking agents include, e.g., 1,1 -bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-((p-azidophenyl)dithio)pro-pioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the -amino groups of lysine, arginine, and histidine side chains (T. E. Creighton, *Proteins: Structure and Molecular Properties*, W. H. Freeman & Co., San Francisco, pp. 79–86 (1983)), acetylation of the N-terminal amine, and amidation of any C-terminal carboxyl group. The modified forms of the residues fall within the scope of the present invention.

Another type of covalent modification of the Apaf-1 polypeptide included within the scope of this invention comprises altering the native glycosylation pattern of the polypeptide. "Altering the native glycosylation pattern" is intended for purposes herein to mean deleting one or more carbohydrate moieties found in native sequence Apaf-1, and/or adding one or more glycosylation sites that are not present in the native sequence Apaf-1.

Glycosylation of polypeptides is typically either N-linked or O-linked. N-linked refers to the attachment of the carbohydrate moiety to the side chain of an 30 asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxylamino acid, most commonly serine or threonine, although 5-hydroxyproline or 5-hydroxylysine may also be used.

Addition of glycosylation sites to the Apaf-1 polypeptide may be accomplished by altering the amino acid sequence such that it contains one or more of the above-described tripeptide sequences (for N-linked glycosylation sites). The alteration may also be made by the addition of, or substitution by, one or more serine or threonine residues to the native sequence Apaf-1 (for O-linked glycosylation sites). The Apaf-1 amino acid sequence may optionally be altered through changes at the DNA level, particularly by mutating the DNA encoding the Apaf-1 polypeptide at preselected bases such that codons are generated that will translate into the desired amino acids. The DNA mutation(s) may be made using methods described above and in U.S. Pat. No. 5,364,934, Supra.

Another means of increasing the number of carbohydrate moieties on the Apaf-1 polypeptide is by chemical or enzymatic coupling of glycosides to the polypeptide. Depending on the coupling mode used, the sugar(s) may be attached to (a) arginine and histidine, (b) free carboxyl groups (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, *CRC Crit. Rev. Biochem.*, pp. 259–306 (1981).

Removal of carbohydrate moieties present on the Apaf-1 polypeptide may be accomplished chemically or enzymatically or by mutational substitution of codons encoding for amino acid residues that serve as targets for glycosylation. For instance, chemical deglycosylation by exposing the polypeptide to the compound trifluoromethanesulfonic acid, or an equivalent compound can result in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.*, 259:52 (1987) and by Edge, et al., *Anal. Biochem.*, 118:131 (1981). Enzymatic cleavage of carbohydrate moieties on polypeptides can be achieved by the use of a variety of endo- and exo-glycosidases as described by Thotakura, et al., *Meth. Enzymol.*, 138:350 (1987).

Glycosylation at potential glycosylation sites may be prevented by the use of the compound tunicamycin as described by Duskin, et al.,*J. Biol. Chem.*, 257:3105 (1982). Tunicamycin blocks the formation of protein-N-glycoside linkages.

Another type of covalent modification of Apaf-1 comprises linking the Apaf-1 polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

8. Apaf-1 Chimeras

The present invention also provides chimeric molecules comprising Apaf-1 fused to another, heterologous polypeptide or amino acid sequence.

In one embodiment, the chimeric molecule comprises a fusion of the Apaf-1 with a tag polypeptide which provides an epitope to which an anti-tag antibody can selectively bind. The epitope tag is generally placed at the amino- or carboxyl- terminus of the Apaf-1. The presence of such epitope-tagged forms of the Apaf-1 can be detected using an antibody against the tag polypeptide. Also, provision of the epitope tag enables the Apaf-1 to be readily purified by affinity purification using an anti-tag antibody or another type of affinity matrix that binds to the epitope tag.

Various tag polypeptides and their respective antibodies are well known in the art. Examples include the flu HA tag polypeptide and its antibody 12CA5 (Field, et al., *Mol. Cell.*

Biol., 8:2159–2165 (1988)); the c-myc tag and the 8F9, 3C7, 6E10, G4, B7 and 9E10 antibodies thereto (Evan, et al., *Molecular and Cellular Biology*, 5:3610–3616 (1985)); and the Herpes Simplex virus glycoprotein D (gD) tag and its antibody (Paborsky, et al., *Protein Engineering*, 3(6):547–553 (1990)). Other tag polypeptides include the Flag-peptide (Hopp, et al., *BioTechnology*, 6:1204–1210 (1988)); the KT3 epitope peptide (Martin, et al., *Science*, 255:192–194 (1992)); an α-tubulin epitope peptide (Skinner, et al., *J. Biol. Chem.*, 266:15163–15166 (1991)); and the T7 gene 10 protein peptide tag (Lutz-Freyermuth, et al., *Proc. Natl. Acad. Sci. USA*, 87:6393–6397 (1990)). Once the tag polypeptide has been selected, an antibody thereto can be generated using the techniques disclosed herein.

Generally, epitope-tagged Apaf-1 may be constructed and produced according to the methods described above. Apaf-1-tag polypeptide fusions are preferably constructed by fusing the cDNA sequence encoding the Apaf-1 portion in-frame to the tag polypeptide DNA sequence and expressing the resultant DNA fusion construct in appropriate host cells. Ordinarily, when preparing the Apaf-1-tag polypeptide chimeras of the present invention, nucleic acid encoding the Apaf-1 will be fused at its 3' end to nucleic acid encoding the N-terminus of the tag polypeptide, however 5' fusions are also possible. For example, a polyhistidine sequence of about 5 to about 10 histidine residues may be fused at the N-terminus or the C- terminus and used as a purification handle in affinity chromatography.

Epitope-tagged Apaf-1 can be purified by affinity chromatography using the anti-tag antibody. The matrix to which the affinity antibody is attached may include, for instance, agarose, controlled pore glass or poly(styrenedivinyl) benzene. The epitope-tagged Apaf-1 can then be eluted from the affinity column using techniques known in the art.

In another embodiment, the chimeric molecule comprises an Apaf-1 polypeptide fused to an immunoglobulin sequence. The chimeric molecule may also comprise a particular domain sequence of Apaf-1, such as the Ced-4-like domain sequence of native Apaf-1 fused to an immunoglobulin sequence. This includes chimeras in monomeric, homo- or heteromultimeric, and particularly homo- or heterodimeric, or -tetrameric forms; optionally, the chimeras may be in dimeric forms or homodimeric heavy chain forms. Generally, these assembled immunoglobulins will have known unit structures as represented by the following diagrams.

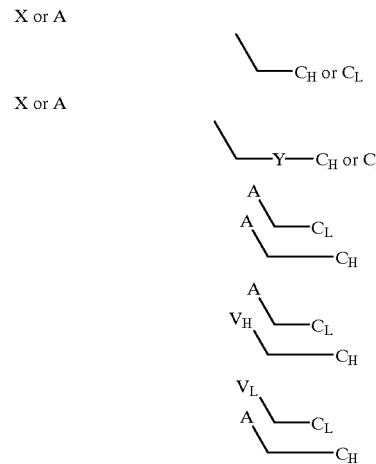

A basic four chain structural unit is the form in which IgG, IgD, and IgE exist. A four chain unit is repeated in the higher molecular weight immunoglobulins; IgM generally exists as a pentamer of basic four-chain units held together by disulfide bonds. IgA globulin, and occasionally IgG globulin, may also exist in a multimeric form in serum. In the case of multimers, each four chain unit may be the same or different.

The following diagrams depict some exemplary monomer, homo- and heterodimer and homo- and heteromultimer structures. These diagrams are merely illustrative, and the chains of the multimers are believed to be disulfide bonded in the same fashion as native immunoglobulins.

monomer:

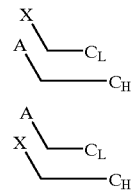

homodimer:

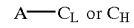

heterodimer:

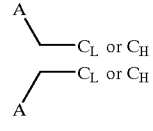

homotetramer:

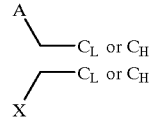

hetertetramer:

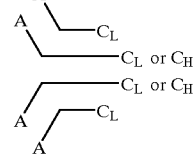

and

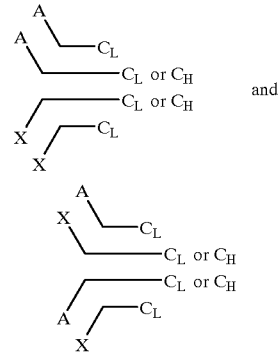

In the foregoing diagrams, "A" means an Apaf-1 sequence or an Apaf-1 sequence fused to a heterologous sequence; X is an additional agent, which may be the same as A or different, a portion of an immunoglobulin superfamily member such as a variable region or a variable region-like domain, including a native or chimeric immunoglobulin variable region, a toxin such a pseudomonas exotoxin or ricin, or a sequence functionally binding to another protein, such as other cytokines (i.e., IL-1, interferon-α or cell surface molecules (i.e., NGFR, CD40, OX40, Fas antigen, T2 proteins of Shope and myxoma poxviruses), or a polypeptide therapeutic agent not otherwise normally, associated with a constant domain; Y is a linker or another receptor sequence; and $V_L$, $V_H$, $C_L$ and $C_H$ represent light or heavy chain variable or constant domains of an immunoglobulin. Structures comprising at least one CRD of an Apaf-1 sequence as "A" and another cell-surface protein having a repetitive pattern of CRDs (such as TNFR) as "X" are specifically included.

It will be understood that the above diagrams are merely exemplary of the possible structures of the chimeras of the present invention, and do not encompass all possibilities. For example, there might desirably be several different "A"s, "X"s, or "Y"s in any of these constructs. Also, the heavy or light chain constant domains may be originated from the same or different immunoglobulins. All possible permutations of the illustrated and similar structures are all within the scope of the invention herein.

In general, the chimeric molecules can be constructed in a fashion similar to chimeric antibodies in which a variable domain from an antibody of one species is substituted for the variable domain of another species. See, for example, EP 0 125 023; EP 173,494; Munro. Nature, 312:597 (Dec. 13, 1984); Neuberger, et al., Nature, 312:604–608 (1984): Sharon. et al., Nature, 309:364–367 (1984); Morrison et al., Proc. Natl. Acad. Sci. USA, 81:6851–6855 (1984); Morrison, et al., Science, 229:1202–1207 (1985); Boulianne, et al., Nature, 312:643–646 (1984); Capon, et al., Nature, 337:525–531 (1989); Traunecker, et al., Nature, 339:68–70 (1989).

Alternatively, the chimeric molecules may be constructed as follows. The DNA including a region encoding the desired sequence, such as an Apaf-1 and/or TNFR sequences is cleaved by a restriction enzyme at or proximal to the 3' end of the DNA encoding the immunoglobulin-like domain (s) and at a point at or near the DNA encoding the N-terminal end of the Apaf-1 or TNFR polypeptide (where use of a different leader is contemplated) or at or proximal to the N-terminal coding region for TNFR (where the native signal is employed). This DNA fragment then is readily inserted proximal to DNA encoding an immunoglobulin light or heavy chain constant region and, if necessary, the resulting construct tailored by deletional mutagenesis. Preferably, the Ig is a human immunoglobulin when the chimeric molecule is intended for in vivo therapy for humans. DNA encoding immunoglobulin light or heavy chain constant regions is known or readily available from cDNA libraries or is synthesized. See for example, Adams, et al., Biochemistry, 19:2711–2719 (1980); Gough, et al., Biochemistry, 19:2702–2710 (1980); Dolby, et al., Proc. Natl. Acad. Sci., USA, 77:6027–6031 (1980); Rice, et al., Proc. Natl. Acad. Sci., 79:7862–7865 (1982); Falkner, et al., Nature, 298:286–288 (1982); and Morrison, et al., Ann. Rev. Immunol., 2:239–256 (1984).

Further details of how to prepare such fusions are found in publications concerning the preparation of immunoadhesins. Immunoadhesins in general, and CD4-Ig fusion molecules specifically are disclosed in WO 89/02922, published Apr. 6, 1989. Molecules comprising the extracellular portion of CD4, the receptor for human immunodeficiency virus (HIV), linked to IgG heavy chain constant region are known in the art and have been found to have a markedly longer half-life and lower clearance than the soluble extracellular portion of CD4 (Capon, et al., Supra; Byrn, et al., Nature, 344:667 (1990)). The construction of specific chimeric TNFR-IgG molecules is also described in Ashkenazi, et al. Proc. Natl. Acad. Sci., 88:10535–10539 (1991); Lesslauer, et al. (J. Cell. Biochem. Supplement 15F, 1991, p. 115 (P 432); and Peppel and Beutler, J. Cell. Biochem. Supplement 15F, 1991, p. 118 (P 439)).

B. Therapeutic and Non-therapeutic Uses for Apaf-1

Apaf-1, as disclosed in the present specification, can be employed to induce apoptosis. This induction of apoptosis may be in a cell free system or in mammalian cells, as described in the examples below.

Apaf-1 of the invention also has utility in non-therapeutic applications. Nucleic acid sequences encoding the Apaf-1 may be used as a diagnostic for tissue-specific typing. For example, procedures like in situ hybridization, Northern and Southern blotting, and PCR analysis may be used to determine whether DNA and/or RNA encoding Apaf-1 is present in the cell type(s) being evaluated, and what amount of the protein or RNA is produced in the cell. This embodiment provides a method for identifying cells that are destined to die. The presence or amount of Apaf-1 protein or RNA is assessed in cells. A high amount in the cell (as compared with a non-apoptotic control) correlates with cells destined to die. A lessened amount correlates with a reduced likelihood cells will die. Expression of Apaf-1 in apoptotic cells is expected to be at least 2–10× greater than expression in normal, non-apoptotic cells.

Nucleic acid sequences encoding Apaf-1 are also useful for the preparation of Apaf-1 by the recombinant techniques described herein.

Isolated Apaf-1 may be used in quantitative diagnostic assays as a control against which samples containing unknown quantities of Apaf-1 may be prepared. Apaf-1 preparations are also useful in generating antibodies, as standards in assays for Apaf-1 (e.g., by labeling Apaf-1 for use as a standard in a radioimmunoassay, radioreceptor assay, or enzyme-linked immunoassay), in affinity purification techniques, and in competitive-type receptor binding assays when labeled with, for instance, radioiodine, enzymes, or fluorophores. Modified forms of the Apaf-1, such as the Apaf-1-IgG chimeric molecules (immunoadhesins) described above, can be used as immunogens in producing anti-Apaf-1 antibodies.

Nucleic acids which encode Apaf-1 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal. e.g., an embryonic stage. A transgene is a DNA which is integrated into the genome of a cell from which a transgenic animal develops. In one embodiment, cDNA encoding Apaf-1 or an appropriate sequence thereof (such as Apaf-1-IgG) can be used to clone genomic DNA encoding Apaf-1 in accordance with established techniques and the genomic sequences used to generate transgenic animals that contain cells which express DNA encoding Apaf-1. Methods for generating transgenic animals, particularly animals such as mice or rats, have become conventional in the art and are described, for example, in U.S. Pat. Nos. 4,736,866 and 4,870,009. Typically, particular cells would be targeted for Apaf-1 transgene incorporation with tissue-specific enhancers. Transgenic animals that include a copy of a transgene encoding Apaf-1 introduced into the germ line of the animal at an embryonic stage can be used to examine the effect of increased expression of DNA encoding Apaf-1. Such animals can be used as tester animals for reagents thought to confer protection from, for example, pathological conditions associated with excessive apoptosis. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of Apaf-1 can be used to construct an Apaf-1 "knock out" animal which has a defective or altered gene encoding Apaf-1 as a result of homologous recombination between the endogenous gene encoding Apaf-1 and altered genomic DNA encoding Apaf-1 introduced into an embryonic cell of the animal. For example, cDNA encoding Apaf-1 can be used to clone genomic DNA encoding Apaf-1 in accordance with established techniques. A portion of the genomic DNA encoding Apaf-1 can be deleted or replaced with another gene, such as a gene encoding a selectable marker which can be used to monitor integration. Typically, several kilobases of unaltered flanking DNA (both at the 5' and 3' ends) are included in the vector (see e.g., Thomas and Capecchi, *Cell*. 51:503 (1987) for a description of homologous recombination vectors). The vector is introduced into an embryonic stem cell line (e.g., by electroporation) and cells in which the introduced DNA has homologously recombined with the endogenous DNA are selected (see e.g., Li et al., *Cell*, 69:915 (1992)). The selected cells are then injected into a blastocyst of an animal (e.g., a mouse or rat) to form aggregation chimeras (see e.g., Bradley, in *Teratocarcinomas and Embryonic Stem Cells: A Practical Approach*, E. J. Robertson. ed., IRL, Oxford. 1987, pp. 13–152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the Apaf-1 polypeptide, including for example, non-regulated growth of cells and/or development of tumors.

The Apaf-1 protein is useful in assays for identifying therapeutically active molecules that modulate apoptosis. Specifically, compounds that either inhibit the initiation of apoptosis or enhance such initiation can be conveniently identified by these screening methods. Molecules inhibiting apoptosis are useful to prevent cell death, for example in degenerative disease or to extend the life of cultured cells. Molecules enhancing or promoting the initiation of apoptosis are useful for example in therapy of cancer or in promoting death of particular cells in vitro.

Assay of candidate compounds able to competitively compete with cytochrome c for specific binding to Apaf-1 provides for high-throughput screening of chemical libraries, and is particularly useful for screening small molecule drug candidates. Small molecules, usually less than 10K molecules weight, are desirable as therapeutics since they are more likely to be permeable to cells, are less susceptible to degradation by cells, and are not as apt to elicit an immune response as proteins. Small molecules include, but are not limited to, synthetic organic or inorganic compounds. Many pharmaceutical companies have extensive libraries of such molecules, which can be conveniently screened by assessing binding to Apaf-1.

Assay of candidate compounds able to replace cytochrome c in the cell free apoptotic assay described above further provides a useful screening method. Combining Apaf-1. Apaf-3. dATP, and the candidate drug, for example, in the presence of caspase 3 precursor, induction of apoptosis is measured by proteolytic cleavage of the enzyme or by DNA fragmentation.

C. Anti-Apaf-1 Antibody Preparation

The present invention further provides anti-Apaf-1 antibodies. Antibodies against Apaf-1 may be prepared as follows. Exemplary antibodies include polyclonal, monoclonal, humanized, bispecific, and heteroconjugate antibodies.

1. Polyclonal Antibodies

The Apaf-1 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the Apaf-1 polypeptide or a fusion protein thereof. An example of a suitable immunizing agent is a Apaf-1 -IgG fusion protein or chimeric molecule (including an Apaf-1 ECD-IgG fusion protein). Cells expressing Apaf-1 at their surface may also be employed. It may be useful to conjugate the immunizing agent to a protein known to be immunogenic in the mammal being immunized. Examples of such immunogenic proteins which may be employed include but are not limited to keyhole limpet hemocyanin, serum albumin, bovine thyroglobulin, and soybean trypsin inhibitor. An aggregating agent such as alum may also be employed to enhance the mammal's immune response. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for antibody titer. If desired, the mammal can be boosted until the antibody titer increases or plateaus.

2. Monoclonal Antibodies

The anti-Apaf-1 antibodies may, alternatively, be monoclonal antibodies. Monoclonal antibodies may be prepared using hybridoma methods, such as those described by Kohler and Milstein, Supra. In a hybridoma method, a mouse, hamster, or other appropriate host animal, is typically immunized (such as described above) with an immunizing agent to elicit lymphocytes that produce or are capable of producing antibodies that will specifically bind to the immunizing agent. Alternatively, the lymphocytes may be immunized in vitro.

The immunizing agent will typically include the Apaf-1 polypeptide or a fusion protein thereof. An example of a suitable immunizing agent is a Apaf-1 -IgG fusion protein or chimeric molecule. Cells expressing Apaf-1 at their surface may also be employed. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59–103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, *J. Immunol.*, 133:3001 (1984): Brodeur. et al., *Monoclonal Antibody Production Techniques and Applications,* Marcel Dekker, Inc., New York. (1987) pp. 51–63).

The culture medium in which the hybridoma cells are cultured can then be assayed for the presence of monoclonal antibodies directed against Apaf-1 . Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods (Goding, Supra). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567, Morrison, et al., Supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent cross-linking.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 12, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields an $F(ab')_2$ fragment that has two antigen combining sites and is still capable of cross-linking antigen.

The Fab fragments produced in the antibody digestion also contain the constant domains of the light chain and the first constant domain ($CH_1$) of the heavy chain. Fab' fragments differ from Fab fragments by the addition of a few residues at the carboxy terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

3. Humanized Antibodies

The Apaf-1 antibodies of the invention may further comprise humanized antibodies or human antibodies. Humanized forms of non-human (e.g., murine) antibodies are chimeric immunoglobulins immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones, et al., *Nature,* 321:522–525 (1986); Reichmann, et al., *Nature,* 332:323–329 (1988); and Presta, *Curr. Op. Struct. Biol.,* 2:593–596 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones. et al., *Nature,* 321:522–525 (1986); Riechmann et al., *Nature,* 332:323–327 (1988); Verhoeyen, et al., *Science,* 239:1534–1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically full human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims, et al., *J. Immunol.,* 151:2296(1993); Chothia and Lesk, *J. Mol. Biol.,* 196:901 (1987)). Another method uses a particular framework derived from the consensus sequence of all human antibodies of a particular subgroup of light or heavy chains. The same framework may be used for several different humanized antibodies (Carter, et al., *Proc. Natl. Acad. Sci. USA,* 89:4285 (1992); Presta, et al., *J. Immunol.,* 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence. i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see. WO 94/04679 published Mar. 3, 1994).

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits, et al., *Proc. Natl. Acad. Sci. USA,* 90:2551–255 (1993); Jakobovits. et al., *Nature,* 362:255–258 (1993); Bruggermann, et al., *Year in Immuno.,* 7:33 (1993)). Human antibodies can also be produced in phage display libraries (Hoogenboom and Winter, *J. Mol. Biol.,* 227:381 (1991); Marks, et al., *J. Mol. Biol.,* 222:581 (1991)). The techniques of Cole, et al. and Boerner et al. are also available for the preparation of human monoclonal antibodies (Cole, et al., *Monoclonal Antibodies and Cancer Therapy, Alan R. Liss, p.* 77 (1985) and Boerner, et al., *J. Immunol.,* 147(1):86–95 (1991)).

4. Bispecific Antibodies

Bispecific antibodies are monoclonal, preferably human or humanized, antibodies that have binding specificities for at least two different antigens. In the present case, one of the binding specificities is for the Apaf-1. the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Millstein and Cuello, *Nature,* 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993. and in Traunecker, et al., *EMBO J.,* 10:3655–3659(1991).

According to a different and more preferred approach, antibody variable domains with the desired binding specificities (antibody-antigen combining sites) are fused to immunoglobulin constant domain sequences. The fusion preferably is with an immunoglobulin heavy-chain constant domain, comprising at least part of the hinge. CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy-chain/light-chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies see, for example, Suresh. et al., *Methods in Enzymology,* 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies may be prepared in vitro using known methods in synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

D. Therapeutic and Non-therapeutic Uses for Apaf-1 Antibodies

The anti-Apaf-1 antibodies of the invention have therapeutic utility. Agonistic anti-Apaf-1 antibodies, for instance, may be employed to activate or stimulate apoptosis in cancer cells. Alternatively, antagonistic antibodies may be used to block excessive apoptosis (for instance in neurodegenerative disease) or to block potential autoimmune/inflammatory effects of Apaf-1 resulting from caspase-3 activation.

Anti-Apaf-1 antibodies may further be used in diagnostic assays for anti-Apaf-1, e.g., detecting its expression in specific cells, tissues, or serum, Various diagnostic assay techniques known in the art may be used, such as competitive binding assays, direct or indirect sandwich assays and immunoprecipitation assays conducted in either heterogeneous or homogeneous phases (Zola, *Monoclonal Antibodies: A Manual of Techniques,* CRC Press, Inc. (1987) pp. 147–158). The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter, et al., *Nature,* 144:945 (1962); David, et al., *Biochemistry,* 13:1014 (1974): Pain, et al., *J. Immunol. Meth.,* 40:219 (1981); and Nygren, *J. Histochem. and Cytochem.,* 30:407 (1982).

Anti-Apaf-1 antibodies also are useful for the affinity purification of Apaf-1 from recombinant cell culture or natural sources. In this process, the antibodies against Apaf-1 are immobilized on a suitable support, such a Sephadex resin or filter paper, using methods well known in the art. The immobilized antibody then is contacted with a sample containing the Apaf-1 to be purified, and thereafter the support is washed with a suitable solvent that will remove substantially all the material in the sample except the Apaf-1, which is bound to the immobilized antibody. Finally, the support is washed with another suitable solvent that will release the Apaf-1 from the antibody.

Anti-Apaf-1 antibodies are also useful for identifying Apaf-1 expression in cells, providing a useful marker for cells that are destined to die, as discussed above.

E. Kits Containing Apaf-1 or Anti-Apaf-1 Antibodies

In a further embodiment of the invention, there are provided articles of manufacture and kits containing Apaf-1 or anti-Apaf-1 antibodies which can be used, for instance, for the therapeutic or non-therapeutic applications described above. The article of manufacture comprises a container with a label. Suitable containers include, for example, bottles, vials, and test tubes. The containers may be formed from a variety of materials such as glass or plastic. The container holds a composition which includes an active agent that is effective for therapeutic or non-therapeutic applications, such as described above. The active agent in the composition is Apaf-1 or an anti-Apaf-1 antibody. The label on the container indicates that the composition is used for a specific therapy or non-therapeutic application, and may also indicate directions for either in vivo or in vitro use, such as those described above.

The kit of the invention will typically comprise the container described above and one or more other containers comprising materials desirable from a commercial and user standpoint, including buffers, diluents, filters, needles, syringes, and package inserts with instructions for use.

F. Model System for Apoptosis

A model system for apoptosis is provided by combining Apaf-1, Apaf-3, dATP and cytochrome c. This combination of agents, both in a cell-free system and in mammalian cells, is sufficient to trigger apoptosis. The apoptotic activity is confirmed by the proteolytic cleavage of caspase 3 and by the fragmentation of DNA. Using this model system, novel agents are screened for their ability to modulate apoptosis.

EXAMPLES

The following examples are offered for illustrative purposes only, and are not intended to limit the scope of the present invention in any way.

Experimental Procedures

Genereal Methods and Materials dATP and other nucleotides were obtained from Pharmacia; Radio-active materials from Amersham; molecular weight standards for SDS-PAGE and gel filtration chromatography from Bio-Rad. Protein concentrations were determined by the Bradford assay method. General molecular biology methods were performed as described in Sambrook, et al., Supra.

Example 1

Fractionation of Cytosol and Reconstitution of Caspase-3 Activation

The cell-free in vitro system as described in Liu, et al. (*Cell* 86:147–157, (1996)) in which the apoptotic program is initiated by the addition of deoxyATP (dATP) was used in these studies. This system permits fractionation and purification of the biochemical components that trigger activation of the apoptotic proteases and DNA fragmentation. Initiation of the apoptotic program leads to activation of caspase-3 and ultimately to fragmentation of DNA in nuclei. The cell free system combined fractions of a 100,000×g cytosolic supernatant prepared from suspension cultures of Hela cells (S100) with cytochrome c and activating dATP, as described in Liu, et al., Supra. Caspase-3 activation was monitored by cleavage of in vitro translated, $^{35}S$-labeled affinity purified caspase-3 precursor. The proteolytic fragments were visualized by SDS-polyacrylamide gel electrophoresis (PAGE) followed by phosphorimaging.

FIG. 1 shows the fractionation scheme that was used for the separation of cytochrome c (Apaf-2) from two other required factors. Apaf-1 and Apaf-3. The initial step was SP-Sepharose chromatography of an S100 fraction of Hela cell Cytosol, which separated cytochrome c (bound fraction)

from Apaf-1 and Apaf-3 (flow-through). To separate Apaf-1 and Apaf-3, the flow-through fraction was loaded onto a hydroxylapatite column. The flow-through and bound fractions were collected.

To reconstitute the apoptotic initiation program, aliquots of flow-through (Apaf-3) and bound (Apaf-1) fractions (4 µl each) and an aliquot of cytochrome c (0.2 µg in 1 µ) were incubated alone or in combination and in the presence or absence of 1 mM dATP. To each sample was added an aliquot (3 µl) of in vitro translated, $^{35}$S-labeled caspase 3, and the samples were incubated at 30° C. for one hour in a final volume of 25 µl buffer A (20 mM Hepes-KOH, pH 7.5, 10 mM KC1, 1.5 mM $MgCl_2$, 1 mM sodium EDTA, 1 mM sodium EGTA, 1 mM dithiothreitol, and 0.1 mM PMSF). At the end of the incubation, 7 µl of 4×SDS sample buffer was added to each reaction. After boiling for three minutes, each sample was then subjected to 15% SDS PAGE and the gel transferred to a nitrocellulose filter. The filter was exposed to a Phosphorimaging plate for 16 hours at room temperature and visualized in a FuJi BAS- 1000 Phosphorimager.

Figure 2:
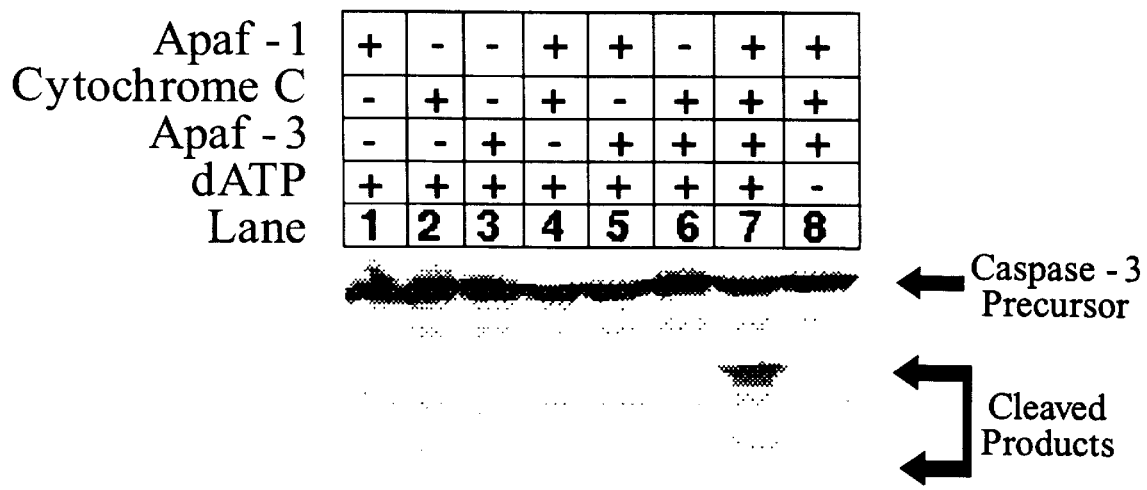
FIG. 2 shows a combination of agents which triggers apoptosis, as assayed by proteolytic cleavage of caspase-3 precursor into its activated form.

As shown in FIG. 2, neither fraction alone was competent to activate caspase-3 when incubated with cytochrome c and dATP (lanes 1–6). However, when the two fractions (Apaf-1 and Apaf-3) were mixed in the presence of cytochrome c and dATP, caspase-3 activation was restored (lane 7). No activity was detected when dATP and cytochrome c were omitted from the reaction (lanes 5 and 8).

Example 2

Purification of Apaf-1

For purposes of further purification, Apaf-1 activity was assayed by incubating various cytosolic fractions with cytochrome c, dATP, the crude Apaf-3 fraction, and the substrate caspase-3, as described above for Example 1. As shown above for Example 1, Apaf-1 activity results in the cleavage of caspase-3. Purification of Apaf-1 was achieved through a six step procedure.

Purification of Apaf-1 from HeLa S-100

All purification steps were carried out at 4° C. All chromatography steps except the SP-Sepharose column (Pharmacia) and first Hydroxylapatite column (Bio-Rad) were carried out using an automatic fast protein liquid chromatography (FPLC) station (Pharmacia).

700 ml (4.9 g of protein) of HeLa S-100 from 100 liter of suspension cultured HeLa cells were prepared as described in Liu, et al., 1996, Supra. and applied to a SP-Sepharose column (200 ml bed volume) equilibrated with buffer A. Buffer A was prepared as described above for Example 1. An 800 ml flow-through fraction (3,648 mg of protein) was collected and loaded directly to a Hydroxylapaptite column (50 ml bed volume) equilibrated with buffer A. The column was washed with three column volumes of buffer A containing 1 M NaCl followed by two column volumes of buffer A. The bound material was eluted with 200 ml 0.3 M $KPO_4$, pH 7.5. The protein peak was eluted from the column (115 ml, 287 mg of protein), was dialyzed against buffer A, and then loaded onto a second hydroxylapaptite column (10 ml bed volume) equilibrated with buffer A. The column was eluted with 200 ml buffer A to 250 mM $KPO_4$, pH 7.5 linear gradient.

Fractions of 10 ml each were collected and assayed for Apaf-1 activity (caspase-3 cleavage), as described above for Example 1. Active fractions (50 ml, 11 mg of protein) were pooled, dialyzed against buffer A, and then loaded onto a 5 ml Heparin-Sepharose column (Pharmacia) equilibrated with buffer A. The column was washed with 20 ml of buffer A containing 100 mM NaCl and eluted with 50 ml buffer A containing 100 mM NaCl to buffer A containing 400 mM NaCl linear gradient. Fractions of 4 ml were collected and assayed for Apaf-1 activity. The active fractions (8 ml, 0.86 mg of protein) were pooled and loaded directly onto a Superdex 200 16/60 gel-filtration column equilibrated with buffer A containing 100 mM NaCl. The column was eluted with the same buffer (4 runs) and fractions of 4 ml were collected starting from 30 ml of elution. The fractions were assayed for Apaf-1 activity and the active fractions were pooled (16 ml, 32 µg of protein) and loaded directly onto a Mono Q 5/5 column (Pharmacia) equilibrated with buffer A containing 100 mM NaCl. The column was eluted with 20 ml buffer A containing 100 mM NaCl to buffer A containing 300 mM NaCl linear gradient. Fractions of 1 ml were collected and assayed for Apaf-1 activity.

Figure 3:
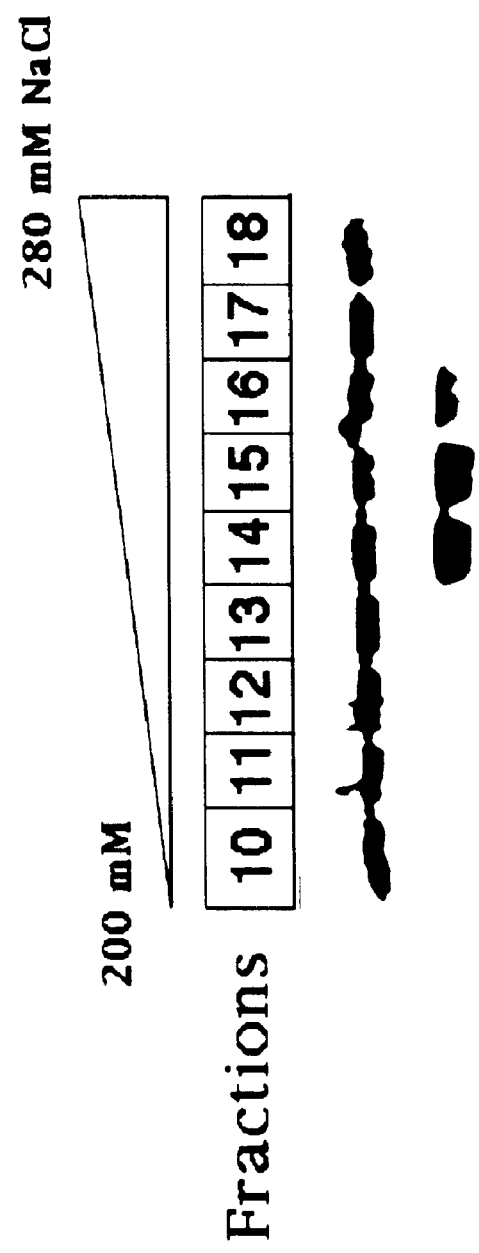
FIG. 3 shows Apaf-1 activity of cytosolic fractions of Hela cells supernatant (S100) purified through a Mono Q column.

The results of the last step of purification, a Mono Q column chromatography, are shown in FIG. 3. Apaf-1 activity was eluted from the Mono Q column at 250 mM NaCl (fractions 14–16). The same fractions were subjected to SDS-PAGE followed by silver staining and a single polypeptide band of approximately 130 kDa was observed to co-elute with the Apaf-1 activity (FIG. 4). No other proteins were detected by silver staining in the peak fractions (FIG. 4, fractions 14–16), Apaf-1 activity eluted from gel-filtration columns at about 130 kDa, indicating that Apaf-1 exists as a monomer in solution (data not shown). About 10 microgram of pure Apaf-1 was obtained from the cytosol from 100 liters of HeLa cells.

Example 3

Sequencing and cDNA Cloning of Apaf-1

The 130 kDa Apaf-1 protein was excised from an SDS gel and subjected to trypsin and Lys-C digestion. The resulting peptides were separated by capillary reverse-phase high pressure liquid chromatography (HPLC).

Protein Sequencing of Apaf-1

The 130 kDa Apaf-1 protein band produced as described for Example 2 and shown in FIG. 4 (4–8 pmol) was electroeluted from the SDS polyacrylamide gel onto PVDF membrane (ProBlott, Applied Biosystem) and excised. The band was reduced and alkylated with isopropylacetamide followed by digestion in 20 µl of 0.05 M ammonium bicarbonate, 20% acetonitrile with 0.2 µg of trypsin (Promega) or Lysine-C (Wako) at 37° C. for 17 hours, as described previously (Henzel. et al., *Proc. Natl. Acad. Sci. USA* 90:5011–5015 (1993)). The digested solution was then directly injected onto a 0.32×150 mm C18 capillary column (LC Packing, Inc.). Solvent A was 0.1% aqueous TFA and solvent B was acetonitrile containing 0.07% TFA. The peptides were eluted with a linear gradient of 0–80% solvent B in 120 minutes. Peptide peaks were detected at 195 nm and hand collected into 0.5 ml Eppendorf tubes.

An aliquot (0.2 µl) of each of the isolated HPLC fractions was applied to a pre-made spot of matrix (0.5 µl of 20 mg/ml α-cyano-4-hydroxycinammic acid plus 5 mg/ml nitrocellulose in 50% acetone/50% 2-propanol) on the target place (Shevchenko, et al., *Anal. Chem.,* 68:850–858, (1996)). Ions were formed by matrix-assisted laser desorption/ionization with a 337 nm nitrogen laser. Spectra were acquired with a Perseptive Biosystems Voyager Elite time-of-flight mass spectrometer, operated in linear delayed extraction mode. Subsequently, fragment ions for selected precursor masses were obtained from post-source decay (PSD) experiments (Kaufmann, et al., *International J. Mass Spectro and Ion Processes,* 131:355–385, (1994)). In order to enhance the ion abundances at low mass, collision gas (air) was introduced to the collision cell during the acquisition of the lower portion (<200μ) of the fragment ion spectrum. Each peptide mass and its associated fragment ion masses were used to search an in-house sequence database with an enhanced version of the FRAGFIT program (Henzel, et al., Supra).

Automated protein sequencing was performed on models Procise 494A and 494CL, Applied Biosystems sequencers equipped with an on-line PTH analyzer. Peaks were integrated with Justice Innovation software using Nelson Analytical 760 interfaces. Sequence intepretation was performed on a DEC Alpha (Henzel, et al., 1987, *J. Chromatogr.* 404:41–52).

The sequences of 14 peptides were determined by Mass Spectrometry and Edman degradation (Table 1). Protein data base searches revealed that no proteins in the data bases were identical to Apaf-1.

TABLE 1

Peptide Analyzed by MALDI MS Analysis and Edman Sequencing

| Peptide # | Fraction # | MH+ Measured | MH+ Calculated | Residues in cDNA |
|---|---|---|---|---|
| 1 | Lys-C33a | 1780.8 | 1780.0 | 5–18 |
| 2 | Lys-C6 | 1255.7 | 1255.6 | 43–52 |
| 3 | Lys-C43 | N.D. | 4103.82 | 82–100 |
| 4 | T9 | 913.5 | 913.5 | 121–128 |
| 5 | Lys-C46 | 3153.6[ab] | 3153.6 | 150–178 |
| 6 | Lys-C42 | 3160.8[a] | 3161.8 | 187–212 |
| 7 | Lys-C31 | 1177.8 | 1177.7 | 266–276 |
| 8 | Lys-C29 | 1450.0 | 1449.8 | 291–303 |
| 9 | Lys-C53 | 2747.1[b] | 2745.4 | 502–524 |
| 10 | T24 | 817.6 | 817.5 | 590–596 |
| 11 | Lys-C33b | 735.5 | 735.9 | 627–632 |
| 12 | Lys-C31 | 615.3 | 615.4 | 638–642 |
| 13 | Lys-C32 | 1278 | 1277.7 | 746–757 |
| 14 | T17 | 650.5 | 650.4 | 941–945 |
| 15 | Lys-C28 | 942.7 | 942.5 | 1169–1176 |

[a]Masses that represent average isotopic mass.
[b]The peptide contained a oxidized trytophan resulting in an additional 32 daltons.

Degenerate oligonucleotides encoding peptides 2 and 4 (see Table 1) were used to prime polymerase chain reactions (PCRs) with a HeLa cDNA library as template.

cDNA Cloning of Apaf-1

An aliquot of 1 μl (10⁸ pfu) of a λElox Hela cDNA library (Yokoyama, et al., *Cell*, 75:187–197, (1993)) was heated at 99° C. for 15 minutes to release the DNA contents. The DNA was directly amplified with 300 pmol of the primer-1 degenerate oligonucleotide (SEQ ID NO:3) and 20 pmol SP6 primer (SEQ ID NO:4) using PCR reaction with 5 cycles of 94° C for 30 seconds, 60° C. for 30 seconds; and 72° C. for 1 minute followed by 25 cycles of 94° C. for 30 seconds; 55° C. for 30 seconds; and 72° C. for 1 minute. The PCR product was purified by passing through a PCR Purification column (Qiagen). A portion (1/50) of the purified product was further amplified using 300 pmol of primer-2 (SEQ ID NO:5) and pmol of primer-3 (SEQ ID NO:6) in a PCR reaction as described above.

| Primer | Sequence | SEQ ID NO. |
|---|---|---|
| 1 | 5'-AAAGTAAGAAATGAACCAAC-3'<br>       G  TC T  C  G    T<br>          C C         C<br>          G G         G | 3 |

-continued

| Primer | Sequence | SEQ ID NO. |
|---|---|---|
| | 5'-AAAGTAAGAAATGAACCAAC-3' | 3 |
| SP6 | 5'-ATTTAGGTGACACTATAGAA-3' | 4 |
| 2 | 5'-AATGAACCAACACAACAACA-3'<br>      C  G  T  T<br>          C  C<br>          G  G | 5 |
| 3 | 5'-TTTTGTTGTATAGCATTCAC-3'<br>      C  C  A  T    G<br>          G  C<br>          G | 6 |

A 285 bp PCR product was obtained and subsequently sequenced after subcloning into a PCR II vector using the TA cloning kit (Invitrogen).

The sequencing yielded a 285 base pair DNA fragment that also encoded peptide 3. Probing of the HeLa cDNA library with this PCR fragment identified two overlapping cDNAs with an open reading frame encoding 1194 amino acids with a calculated molecular mass of 136,088 daltons (FIGS. 5A–5G). Multiple in-frame stop codons were identified in the 5' untranslated region of the cDNA, indicating that these cDNA clones encode full length Apaf-1 (data not shown).

The 285 bp PCR product was labeled with α-$^{32}$P-dCTP using redi prime RANDOM Primer Labelling Kit (Amersham) and used to screen the Hela λ-Exlox cDNA library by hybridizing duplicate filters at 42° C. overnight in Rapid-hyb buffer (Amersham). The filters were washed twice with 1× saline citrate (SSC)/0.1% SDS for 15 minutes at room temperature and once with 0.5×SSC/0.1% SDS for 10 minutes at 65° C. Out of 6×10⁵ plaques that were screened, 4 positive clones were identified and a 1.6 kb partial clone was characterized. The 1.6 kb insert was excised and labeled with α-$^{32}$P-dCTP, as described above. The Hela cell cDNA library was re-screened with this 1.6 kb cDNA fragment using the procedures described above. Positive clones (45) were identified and characterized. The longest clone (3kb) containing the 5' portion of Apaf-1 was sequenced. An aliquot of 40 ng of this plasmid was amplified by two PCR primers designated APPN (5'ACATCACGAATCTTTCCCGC) (SEQ ID NO:7) and APPC (5'AACACTTCACTATCACTTCC3') (SEQ ID NO:8) according the 3' end of the 3 kb insert. A 600 bp PCR fragment was generated and labeled with α$^{32}$P-dCTP, as above, The same filters were rescreened with this PCR fragment and 35 positive clones were identified and characterized. The longest one, having an insert of 4.5 kb was sequenced. This clone contained the 3' portion of Apaf-1 which overlaps with the 3 kb 5' clone by 500 bp. The full length cDNA was obtained by ligating the two clones at an EcoR I site located within the 500 bp overlapping region, and is shown in FIGS. 5A–O (SEQ ID NO:1).

FIGS. 5A–G also shows the predicted amino acid sequence (SEQ ID NO:2) encoded by human Apaf-1 (SEQ ID NO:1). All 14 previously sequenced peptides were encoded by the open reading frame of the cDNA (indicated by underlines) and distributed throughout the protein. The measured molecular masses of these peptides by Mass Spectrometry were consistent with the calculated molecular masses, indicating that there is no post-translational modification of these peptides.

Example 4

Domain Structure of Apaf-1

A search of protein data bases (GenBank and Prosite) revealed that the COOH-terminal segment of Apaf-1 contains 13 WD-40 repeats. This loosely conserved set of sequences is found in many regulatory proteins, including β-subunits of heterotrimeric G proteins (Neer, et al., *Nature,* 371:297–300, (1994); Wall, et al., *Cell,* 83: 1047–1058, (1995); Sondek, et al., *Nature,* 379:369–374, (1996)) the LIS-1 gene for Miller-Dieker Lissencephaly (Hattori, et al., 1994, *Nature* 370:216–218), and the SREBP cleavage-activating protein (SCAP) (Hua, et al., *Cell,* 87:415–426, (1996)).

Figure 7:
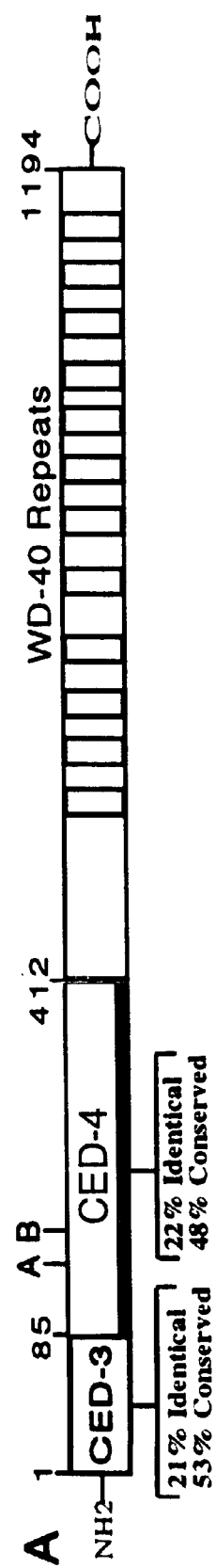
FIG. 7 is a schematic representation of the Apaf-1 structure shown by a horizontal bar. Numbers corresponding to the amino acid residues of FIGS. 5A–5O and 6 are shown. The Ced-3 homologous region, the Ced4 homologous region, and 13 WD repeats are indicated.

The searches of the protein data base (GenBank) also revealed significant similarities between Apaf-1, and Ced-3 and Ced-4, two proteins that are required for the apoptotic program in *C. elegans* (Yuan and Horvitz, Supra) (see FIGS. 8 and 9). The $NH_2$-terminal 85 amino acids of Apaf-1 shows 21% identity and 53% similarity with the $NH_2$-terminal pro-domain of Ced-3 (FIG. 9). The amino acid sequence of Apaf-1 and the N-terminal prodomain of Ced 3 were aligned to the Lipman-Pearson method of DNASTAR program. This domain is followed by a stretch of 310 amino acids that shows 22% identity and 48% similarity with Ced-4 aligned, as described above (FIG. 9). The two longest stretches of amino acids conserved with Cede lie at positions 142–157 and 227–234 of Apaf-1 (FIG. 7, underlined). These two regions correspond to Walker's A- and B-box consensus sequences for nucleotide binding proteins, respectively (Walker, et al., 1982. *EMBO J.* 1:945–95 1). Several amino acids that are known to be required for Ced-4 activity, including two aspartic acids residues at positions 250–251 and the isoleucine at position 258 (Yuan and Horvitz, Supra: Chinnaiyan, et al., Supra), are conserved in Apaf-1 (FIG. 9, asterisks).

Example 5

Tissue Distribution of Apaf-1

Northern Blotting Analysis

Poly(A)+ RNA blots containing 2 μg of poly(A)+ RNA per lane from multiple human adult and fetal tissues were purchased from Clontech. Blots were hybridized with 2×10⁶ cpm/ml of a random primed 607 bp Apaf-1 PCR fragment corresponding to amino acid 590–792 (amplified with 5'ACATCACGAATCTTTCCCGC 3' (SEQ ID NO:9) and 5' CAACACTTCACTATCACTTCC 3') (SEQ ID NO:10) in Rapid-hyb buffer (Amersham) at 65° C. overnight. The filters were washed twice with 1×SSC/0.5% SDS for 15 minutes at 65° C. followed by 0.5% SSC/0.5% SDS for 20 minutes at 65° C.

The same filters were also hybridized at 65° C. for 2 hours with a 2.0 kb β-actin cDNA probe and the filters were then washed, as above. The left filter was exposed to an X-ray film with an intensifying screen at −80° C. for 8 days and the right two filters were exposed to an X-ray film with an intensifying screen at −80° C. for 4 days. The same filters were subsequently hybridized with human M-actin and exposed to film for 2 hours (left filter) or 30 minutes (right two filters) at −80° C. with an intensifying screen. The samples from human adult or fetal tissue are indicated.

Figure 10:
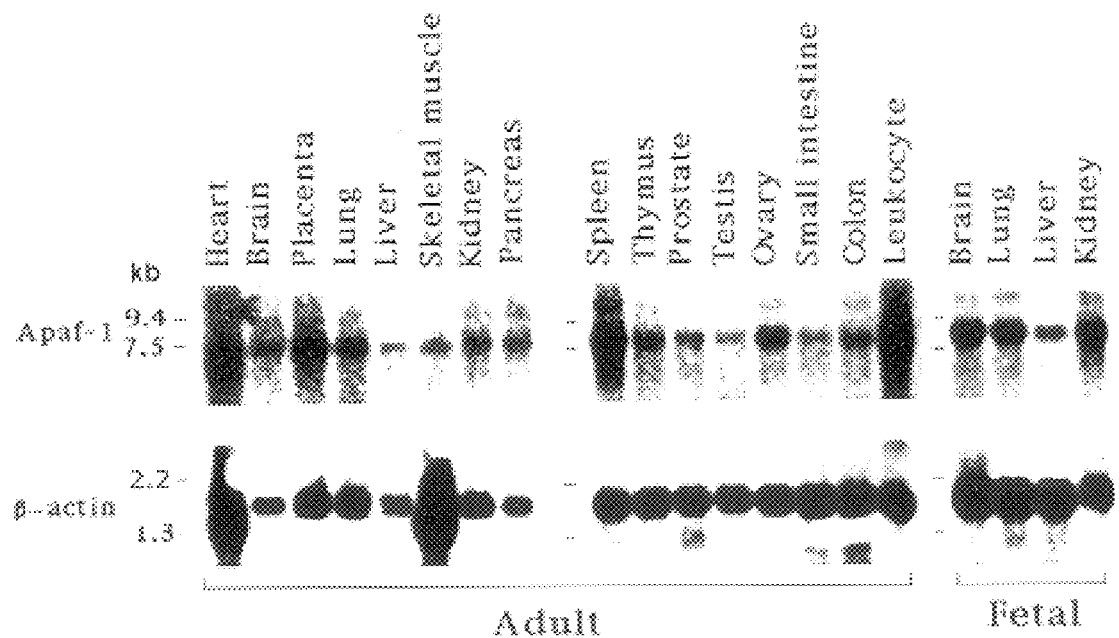
FIG. 10 is a representation of a Northern blot indicating the tissue distribution and relative expression of Apaf-1 mRNA.

FIG. 10 shows the tissue distribution of Apaf-1 mRNA analyzed by Northern blotting of human adult and fetal tissues by the methods described above. In all tissues examined, including adult brain, heart, liver, spleen, skeletal muscle, lung, pancreas, thymus, small intestine, colon, peripheral blood leukocytes, kidney, testis, ovary, and fetal brain, liver, kidney and lung, a predominant mRNA of about 8,000 nucleotides was detected, indicating ubiquitous expression of Apaf-1. Expression was highest in adult spleen and peripheral blood leukocytes and fetal brain, kidney and lung, all of which have a high level of apoptosis.

Example 6

Production of Recombinant Apaf-1

Apaf-1 was translated in vitro from a 6.0 kb cDNA fragment containing the entire coding region of Apaf-1 plus the 577 bp of the 5' untranslated region and about 1.5 kb of the 3' untranslated region cloned into Not I and EcoRI sites of a PCDNA 3.1(−) vector (Invitrogene). The 3' region was truncated at the Eco RI site located at nucleotide 5727 of SEQ ID NO:1. The TNT T7 coupled reciculocyte lysate system (Promega) was used according to the manufacturing instructions.

The translation products were analyzed by Western blotting. Lane 1 contained 30 μl of the Apaf-1 in vitro translation product. Lane 2 contained 30 μl of a translation mixture control, where the vector alone was used as a template in the same translation reaction. Lane 3 contained 5 μl of Apaf-1 purified as described for Example 1.

After electrophoresis, the samples were transferred to a nitrocellulose filter and the filter was probed with an anti-serum (1:5000 dilution) against Apaf-1 raised against a recombinant fusion protein containing amino acids 10–254 of Apaf-1 [SEQ ID NO:2]. The fusion protein (0.5 mg) was used to immunize rabbits via subcutaneous injection of the protein in Freund's Complete adjuvant (1:1). Two boosters of protein in Freund's Incomplete adjuvant (1:1) were given in intervals of two weeks. Antigen-antibody complexes formed in the blot were visualized by an ECL method as described above. The filter was exposed to a Kodak X-OMAT X-ray film for 5 seconds.

Figure 11:
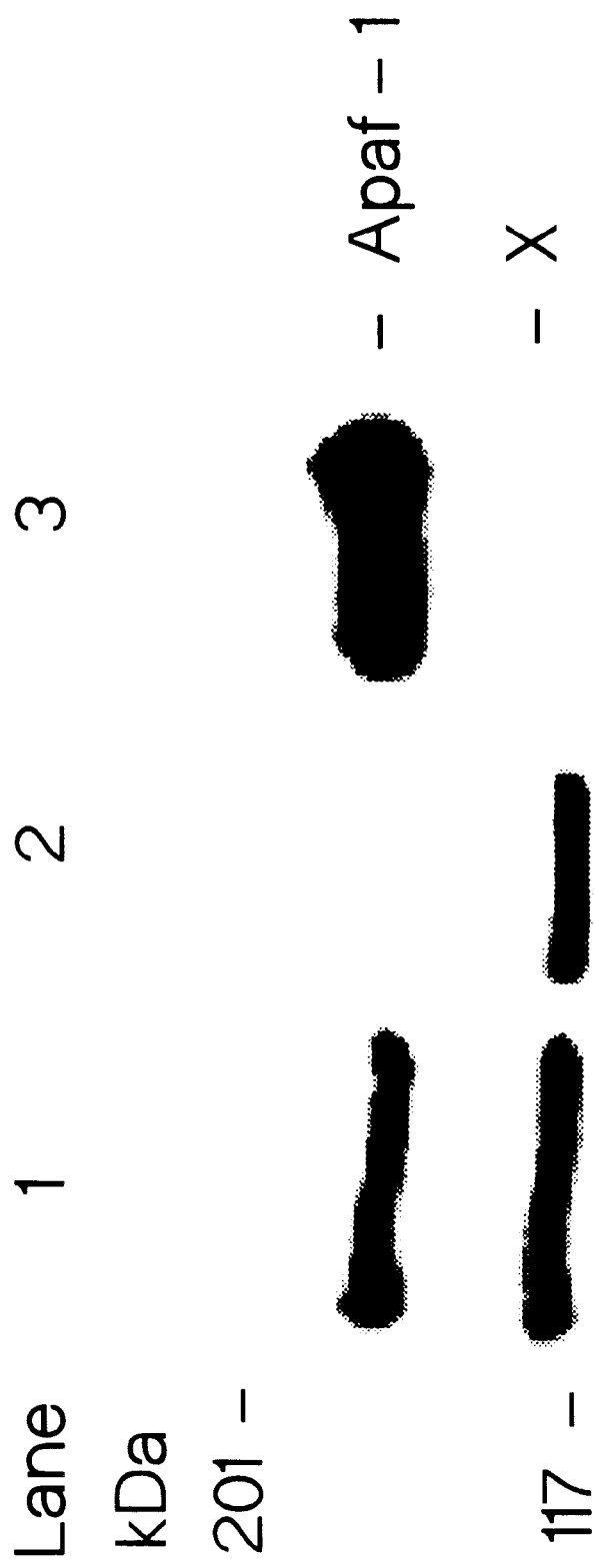
FIG. 11 is a representation of an immunoblot probed with anti-Apaf-1 antibody showing in vitro translation of Apaf-1.

As shown in FIG. 11, the anti-Apaf-1 polyclonal antibody reacted with the purified protein (lane 3). The same antibody also reacted with Apaf-1 synthesized by in vitro translation of the Apaf-1 cDNA in a rabbit reticulocyte lysate system (lane 1). X denotes a cross reactive band in the reticulocyte lysate. The in vitro translated Apaf-1 migrated in an identical position as purified Apaf-1 confirming that the cDNA encoded full length Apaf-1.

Example 7

Cytochrome c Binds to Apaf-1

As noted above, the activation of caspase-3 by Apaf-1 and Apaf-3 requires cytochrome c as well as dATP. To determine whether Apaf-1 interacts directly with cytochrome c. binding studies were performed.

Aliquots of 100 μl of partially purified Apaf-1 were incubated alone or with 2 μg of cytochrome c in the absence or presence of 1 mM dATP, at 30° C. for twenty minutes. The Apaf-1 was partially purified from HeLa cell cytosol through a SP Sepharose column as well as a hydroxylapatite column, as described for Example 2.

After the incubation period, the samples were immuno-precipitated with an anti-Apaf-1 antiserum. The anti-Apaf-1 anti-serum was generated by immunizing rabbits with a recombinant Apaf-1 fusion protein produced as described below.

Primers 5'-GCAAAAGCTCGAAATCATATGCTT CAACATAGAG-3' (SEQ ID NO:1 1) and

5'-TCGCGGCCGCCTCGAGGGCTCTGGTTGTAAG-3' (SEQ ID NO:12) were designed to PCR-amplify the 1.6 kb plasmid Apaf-1 cDNA open reading frame. The amplified 800 bp fragment encoding amino acid 10–254 of Apaf-1 was subcloned inframe into the NdeI/XhoI sites of the bacterial expression vector pET-15b (Novagen). The expression plasmid was transformed into bacteria BL21 (DE3). In a typical Apaf-1 preparation, a 10 ml overnight cultured bacteria containing Apaf-1 expression vector was added into a 500 ml LB broth, cultured for 3 hours by shaking at 220 rpm at 37° C. Isopropyl-1-thio-B-D-galactopyranoside (IPTG) was then added to a final concentration of 1 mM and the mixture cultured for another 2 hours. The bacterial pellet was resuspended in 10 ml of buffer B (6 M GuHCl, 0.1 M Na-phosphate, 0.01 M Tris-HCl, pH 8.0). After centrifugation at 10,000 g for 15 minutes, the supernatant was loaded onto a nickel affinity column (6 ml). The column was washed with 30 ml buffer B followed by 30 ml buffer C (8 M urea, 0.1 M Na-phosphate, 0.01 M Tris-HCl, pH 8.0). The column was eluted with Buffer C containing 250 mM imidazole. About 10 mg Apaf-1 protein was purified from a 500 ml culture.

Western blot analysis of cytochrome c was performed as described in Liu, et al., 1996. Supra, Anti-Apaf-1 anti-serum was generated by immunizing rabbits with a recombinant Apaf-1 fusion protein produced as described above. Immunoblot analysis was performed with horseradish peroxidase conjugated goat anti-mouse (cytochrome c) or goat anti-rabbit (Apaf-1) immunoglobulin G using Enhanced Chemiluminescence western blotting detection reagents (Amersham).

Figure 12:
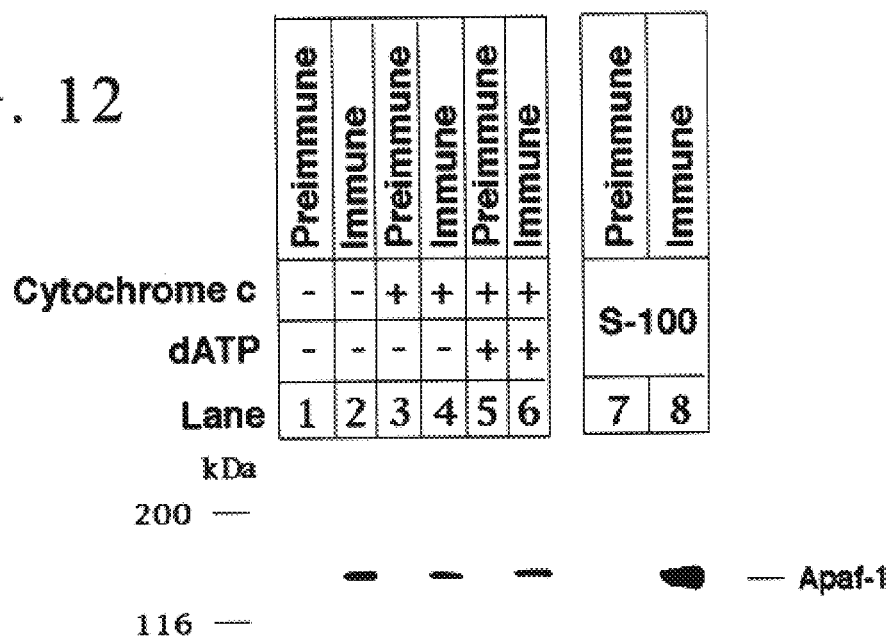
FIG. 12 is a Western blot probed with anti-Apaf-1 antiserum showing immunoprecipitation of Apaf-1.
Figure 13:
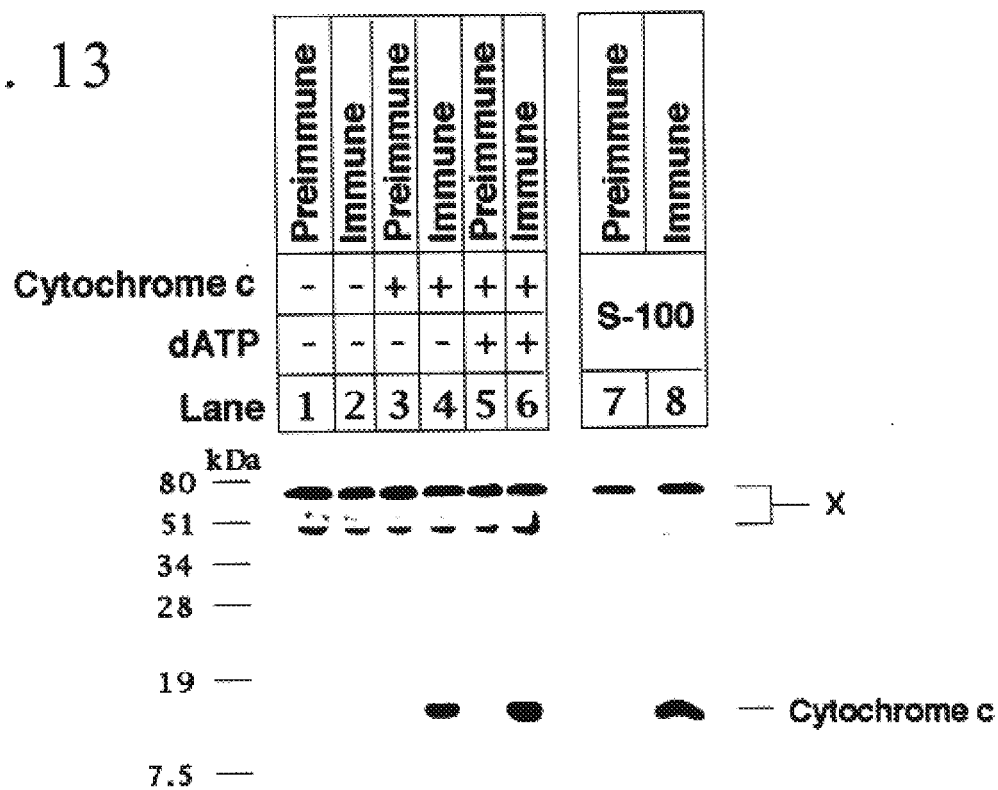
FIG. 13 is a Western blot probed with anti-cytochrome c antibody showing immunoprecipitation of cytochrome c from the Apaf-1/cytochrome c incubation mixture with anti-Apaf-1 antibody.

As shown in FIG. 12, antiserum against Apaf-1 precipitated Apaf-1, while the preimmune serum from the same animal did not. The antiserum against Apaf-1 also precipitated cytochrome c (FIG. 13), indicating that cytochrome c forms a complex with Apaf-1. Preimmune serum caused no such precipitation. The binding of cytochrome c to Apaf-1 was not influenced by the presence or absence of dATP (FIG. 13, lanes 3–6).

To confirm that cytochrome c interacts with Apaf-1 in the crude cytosolic extracts, the immunoprecipitation experiment was performed using un-fractionated HeLa cell S-100. As shown in FIG. 12, lanes 7–8, Apaf-1 in the S-100 fraction was precipitated by the anti-Apaf-1 antiserum. Cytochrome c, which is released to the cytosol during homogenization (see Liu et. al., 1996, Supra) coprecipitated with Apaf-1 (FIG. 12, lane 8). The preimmune serum caused neither protein to precipitate (lane 7).

Example 8

Expression of Apaf-1 in 293 Cells

A 5.7 kb cDNA containing the entire coding region of Apaf-1plus 577 bp of the 5'untranslated region and about 1.5 kb of the 3' untranslated region (truncated at the Eco RI site at nucleotide 5727, as described above for Example 6) was subcloned into NotI and EcoRI sites of a pcDNA 3.1 (−) vector (Invitrogen) and the plasmid (pApaf-1) was prepared using a Qiagen Mega plasmid kit. Human embryonic kidney 293 cells were plated at $1 \times 10^6$ cells per 100 mm dish in medium A (Dulbecco's modified Eagle's Medium containing 100 U/ml of penicillin and 100 μg/ml streptomycin sulfate) supplemented with 10% fetal calf serum, and grown in a monolayer at 37° C. in an atmosphere of 6–7% $CO_2$. After incubation for 24 hours, cells were transfected with 15 μg vector alone; 10 μg pApaf-1 plus 5 μg vector; 10 μg of vector plus 5 μg of pCPP32 (hamster caspase-3) (Wang, et. al., 1996, EMBO J. 15:1012–1020); or 10 μg of pApaf-1 plus 5 μg of pCPP32, using the MBS Transfection Kit (Stratagene) as described in (Hua, et al., Cell 87:415–426 (1996)). After 36 hours of further incubation, the cells were harvested and the cytosolic S-100 fractions were prepared as described above for Example 2

Aliquots (30 μg) of cytosol from control (lane 1), pApaf-1 transfected (lanes 2,4), and pCPP32 transfected (lanes 3,4) cells were analyzed in an 8% SDS-PAGE (upper panel of FIG. 14) or in a 15% SDS PAGE (lower panel), and blotted onto nitrocellulose filters. The filters were probed with either a rabbit anti-Apaf-1 antiserum (1:2000, upper panel) or a rabbit anti-hamster caspase-3 (1:2000, lower panel) antibody, respectively. The antigen-antibody complexes were visulaized with horseradish peroxidase conjugated antibodies and Enhanced Chemiluminescence Western blotting reagents (Amersham) as described above.

Figure 14:
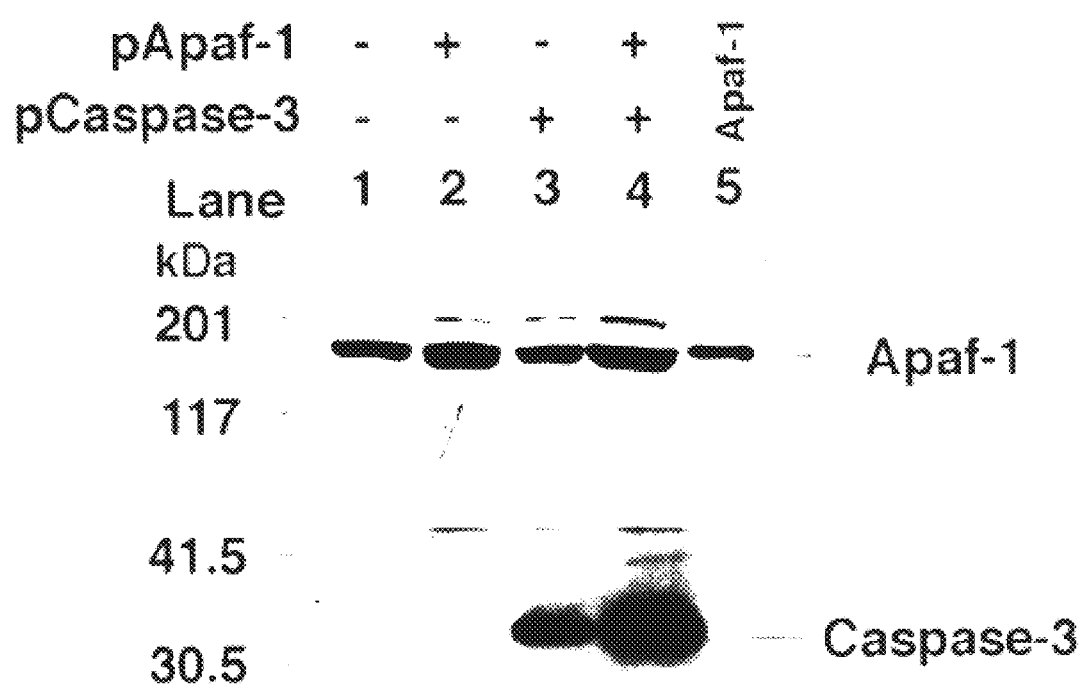
FIG. 14 is a Western blot probed with anti-Apaf-1 antibody and with anti-caspase-3 antibody and demonstrating expression of recombinant Apaf-1 and caspase-3 in mammalian cells.

The films were exposed for 30 seconds (upper panel) or 40 seconds (lower panel). Lane 5 contained 3 μl of Apaf-1 protein purified to the MonoQ column step described for Example 2. The results are shown in FIG. 14, and show expression of pApaf-1 and pCaspase-3 in mammalian cells.

The cytosol of the transfected cells was further analyzed for its ability to induce apoptosis, using the cell-free assay described above for Example 1. Aliquots of 40 μg of cytosol prepared from 293 cells transfected with the indicated plasmids were incubated with buffer A; in the presence of 1 mM dATP; 0.2 μg of cytochrome c; or 1 mM dATP plus 0.2 μg cytochrome c at 30° C. for thirty minutes, in a final volume of 20 μl adjusted with buffer A. The samples were subjected to 15% SDS PAGE followed by Western blotting analysis using a rabbit anti-caspase 3 antibody (1:2000). The antigen-antibody complexes were visualized by an ECL method as described above.

Figure 15:
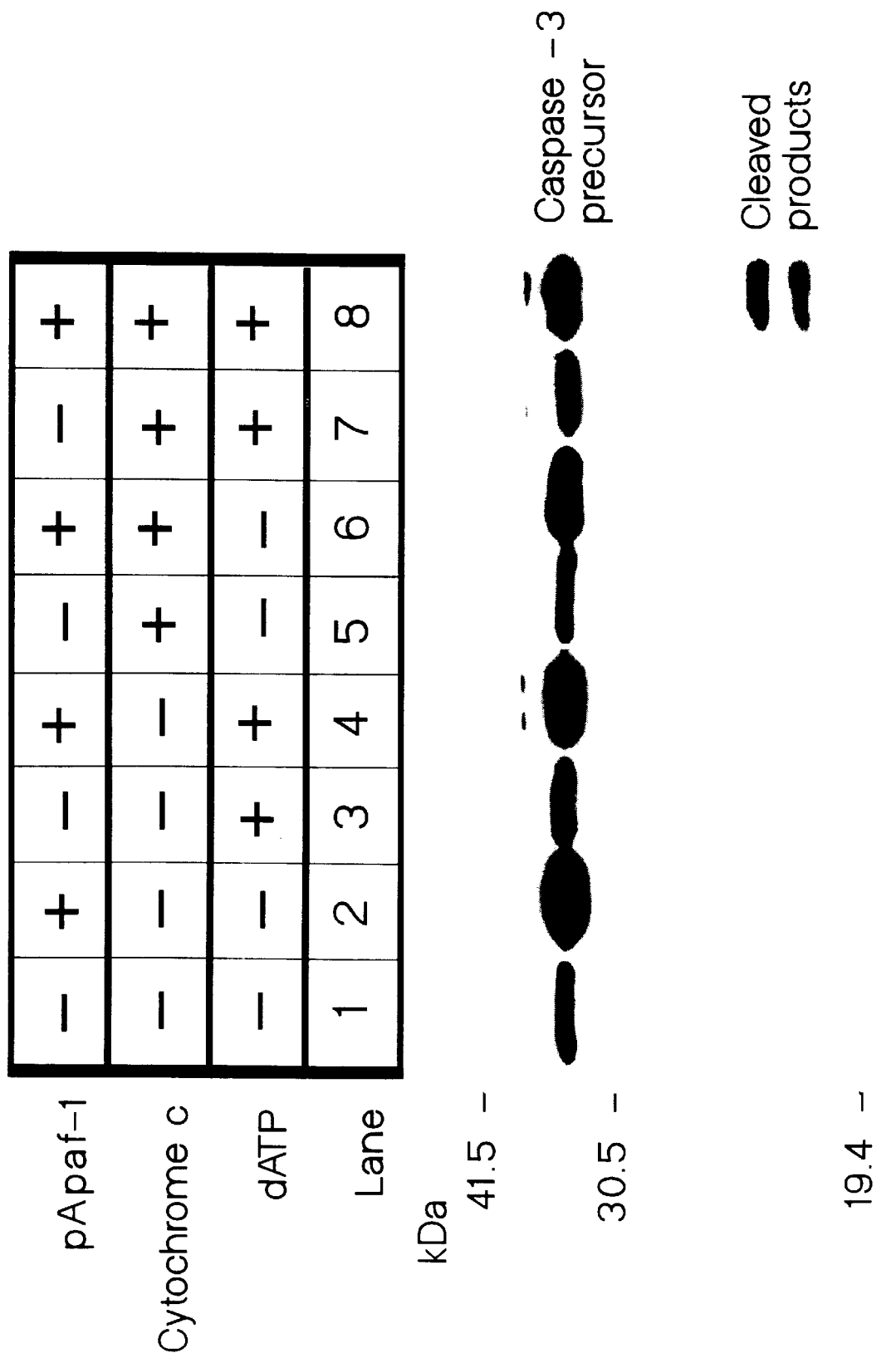
FIG. 15 is a Western blot probed with anti-caspase-3 antibody and demonstrating use of recombinantly expressed Apaf-1 to induce cleavage of caspase 3.

As shown in FIG. 15, recombinant Apaf-1 expressed in mammalian cells was effective in combination with dATP and cytochrome c. This mixture induced cleavage of the caspase 3 precursor to its active cleavage products.

Example 9

Alternatively Spliced Transcript: Apaf-1L
A non-matched Peptide Fragment

To confirm the sequence and identity of the Apaf-1 gene described above, protein expressed from the gene was purified digested, separated by capillary reverse-phase HPLC, and the peptide fragments analyzed by matrix-assisted laser desorption/ionization and mass spectroscopy as described for Example 3. The spectra obtained for the fragments of the expressed protein was compared with the spectra obtained from the purified protein of Example 3. Each of the peptide masses from the expressed protein appeared to match the peptide masses from the purified protein but for one fragment.

A comparison of the nucleotide sequence of a 1.4 kb partial clone encoding the 5' region of Apaf-1 (Ap2) with the 5' region of the Apaf-1 cDNA of Example 3 and FIGS. 5 A–G revealed that Ap2 included 33 nucleotides encoding 11 amino acids at the beginning of the ced-4 homologous regions that was not seen in the cloned Apaf-1.
Alternatively Spliced Transcript To confirm the existence of an alternatively spliced transcript, RT-PCR was performed using specific primers designed to amplify the alternative spliced region of Apaf-1.

HeLa poly (A)+ mRNA was purified using Rapid mRNA purification kit (Pharmacia). The first strand cDNA was carried using a First-Strand cDNA synthesis kit (Pharmacia) with the specific primer AppC 5'-AACACTTCACTATCACTTCC-3' [SEQ ID NO:8], designed from the 3' end of the 3 kb clone described above for Example 3. An aliquot of 400 ng of this first strand cDNA mixture was amplified by two PCR primers: Apn 5' TAATGATTCCTACGTATCATTCTACAATGC-3' [SEQ ID NO:13] and Aps10 5'-GAATGATCTCTAACAGCTTC-3' [SEQ ID NO:14], designed from the 5' side and the 3' side of the additional 33 nucleotides, respectively.

Both 316 bp and 283 bp PCR products (shown in FIG. 17) were subcloned into the PCR II vector using TA cloning kit (Invitrogen) and sequenced. The resulting nucleotide sequence of Apaf-1 L is shown below [SEQ ID NO:15]. Its imputed amino acid sequence is also shown [SEQ ID NO:16].

Differences Between Apaf-1 and Apaf-1L

The amino acid sequence of Apaf-1L [SEQ ID NO:16] differs from the Apaf-1 amino acid sequence [SEQ ID NO:2] by having the additional 11 amino acids (GKDSVSGITSY) amino acid residues 99–109 of SEQ ID NO:16) inserted after amino acid residue 99 shown underlined in the amino acid sequence of Apaf-1L (see FIG. 17). The nucleic acid sequence of Apaf-1L [SEQ ID NO:15], with the additional 33 nucleic acids (TGGTAAAGATTCAGTT AGTGGAATAACTTCGTA), (nucleotides 871–903 of SEQ ID NO:15) underlined, is shown in FIGS. 16A–16H.

Figure 18:
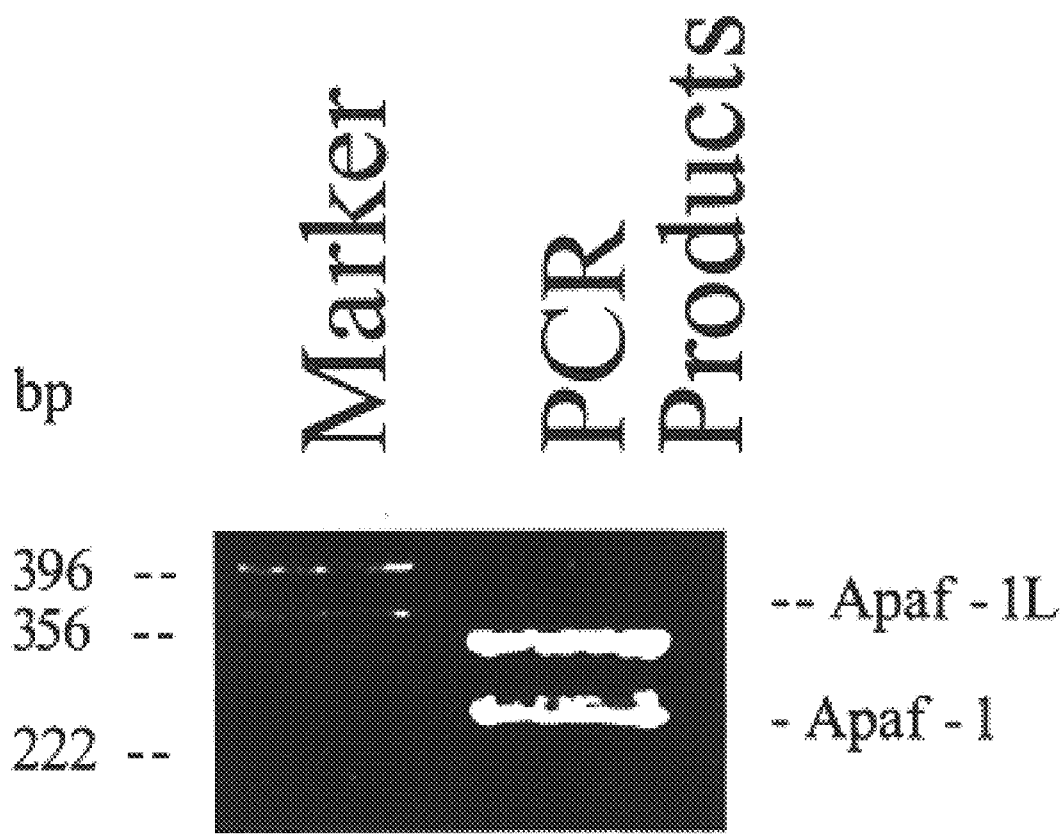
FIG. 18 is a 2% agarose gel stained with ethidium bromide showing two RT-PCR products generated (Apaf-1 and Apaf-1L) from amplifying the first strand cDNA from HeLa mRNA using two primers designed from both the 5' and 3' sides of the additional 33 nucleotides of Apaf-1L, as described in Example 9.

Two PCR products were observed from the RT-PCR reaction, as shown in FIG. 18, indicating the presence of alternatively spliced transcripts from across this region. Direct sequence analysis of the two PCR products confirmed that the longer sequence (Apaf-1L) encodes the sequence of Ap2, having the inserted 11 amino acids. The shorter product had the identical sequence of Apaf-1.

Because the additional eleven amino acids are located at the junction of the Ced-3 homologous region and the Ced-4 homologous region, the overall homology of Apaf-1L with Ced-3 and Ced-4 remains the same as that of Apaf-1. The calculated mass of amino acid 82–100 of Apaf-1L also correlated with the mass measured for peptide K43 of the purified Apaf-1 described above in Example 3, indicating that Apaf-1L exists in the Apaf-1 purified from HeLa cells.

Functional Expression of Apaf-1L

To test the function of recombinant Apaf-1L, a plasmid containing a cDNA insert encoding hamster caspase-3 was co-transfected into human embryonic kidney 293 cells together with a plasmid containing a cDNA insert encoding Apaf-1L (entire coding region of Apaf-1L plus 577 base pairs of 5' untranslated region and 1.5 kb 3' untranslated region) or with the same region of Apaf-1 was inserted into pcDNA3.1. The transfection methods were those described above for Example 8.

Figure 19A:
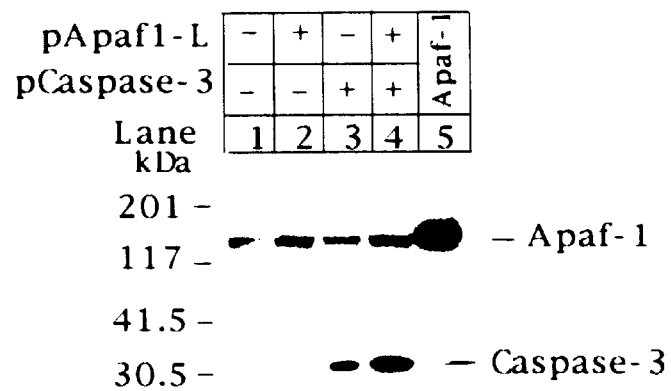
FIG. 19A is a Western Blot probed with anti-Apaf-1 antibody and with anti-caspase-3 antibody, demonstrating expression of recombinant Apaf-1L and caspase-3 in 293 cells.
Figure 19B:
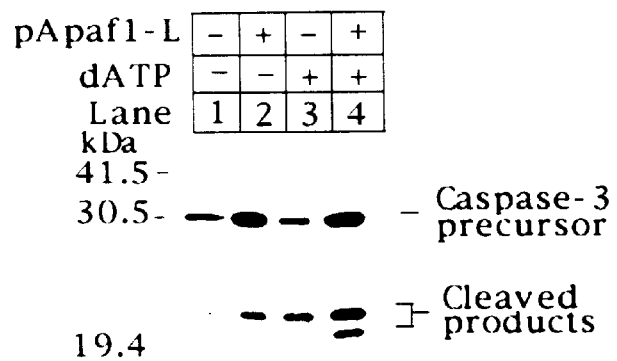
FIG. 19B is a Western Blot probed with anti-caspase-3 antibody and demonstrating use of recombinantly expressed Apaf-1L to induce cleavage of caspase-3.

The transformed cells were assayed for caspase-3 activating activity as described above for Example 3. As shown in FIGS. 19A and 19B, Apaf-1L functioned similarly to Apaf-1, as a higher expression of caspase-3 was observed when cotransfected with Apaf-1L. In addition, cell extracts from Apaf-1L overexpressing cells showed higher caspase activating activity.

All patent and literature references cited in the present specification are hereby incorporated by reference in their entirety.

I claim:

1. An isolated protein having at least about 80% amino acid sequence identity with the sequence of SEQ ID NO:2 or the sequence of SEQ ID NO:16, wherein said protein induces apoptosis or binds cytochrome c.

2. The protein of claim 1 having at least about 90% amino acid sequence identity with the sequence of SEQ ID NO:2 or the sequence of SEQ ID NO:16.

3. The protein of claim 2 having at least about 95% amino acid sequence identity with the sequence of SEQ ID NO:2 or the sequence of SEQ ID NO:16.

4. A protein according to claim 1 comprising the amino acid sequence of SEQ ID NO:2 or SEQ ID NO:16.

5. A chimeric molecule comprising the protein of claim 1 fused to a heterologous amino acid sequence.

6. The chimeric molecule of claim 5, wherein said heterologous amino acid sequence is an epitope tag sequence.

7. The chimeric molecule of claim 5, wherein said heterologous amino acid sequence is an immunoglobulin sequence.

8. The chimeric molecule of claim 7, wherein said immunoglobulin sequence is an IgG.

9. An article of manufacture, comprising a container and a composition contained within said container, wherein the composition includes a protein according to claim 1, 2, 3, 4, 5 or 7.

10. The article of manufacture of claim 9, further comprising instructions for using the protein in vivo or ex vivo.

11. A method for screening compounds for agents which induce apoptosis, the method comprising:

analyzing the ability of a candidate compound to competitively displace cytochrome c binding to a protein according to claim 1, 2, 3, 4, 5 or 7; and correlating competitive displacement of cytochrome c binding to said protein by the candidate compound with the ability of the candidate compound to induce apoptosis.

12. A method for identifying compounds which induce apoptosis, the method comprising, incubating a candidate compound in a mixture containing a protein according to claim 1, 2, 3, 4, 5 or 7, dATP, and cytochrome c;

adding a caspase precursor to the incubating mixture; and correlating a change in cleavage of the caspase precursor in the presence of the candidate compound as compared with cleavage in the absence of the compound with the candidate compound's ability to induce apoptosis.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 7042 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: Coding Sequence
      (B) LOCATION: 578...4159
      (D) OTHER INFORMATION:

(xi) SEQUENCE DESCRIPTION: SEQ ID NO:1:

```
AAGAAGAGGT AGCGAGTGGA CGTGACTGCT CTATCCCGGG CAAAAGGGAT AGAACCAGAG      60

GTGGGGAGTC TGGGCAGTCG GCGACCCGCG AAGACTTGAG GTGCCGCAGC GGCATCCGGA     120

GTAGCGCCGG GCTCCCTCCG GGGTGCAGCC GCCGTCGGGG GAAGGGCGCC ACAGGCCGGG     180

AAGACCTCCT CCCTTTGTGT CCAGTAGTGG GGTCCACCGG AGGGCGGCCC GTGGGCCGGG     240

CCTCACCGCG GCGCTCCGGG ACTGTGGGGT CAGGCTGCGT TGGGTGGACG CCCACCTCGC     300
```

```
CAACCTTCGG AGGTCCCTGG GGGTCTTCGT GCGCCCCGGG GCTGCAGAGA TCCAGGGGAG     360

GCGCCTGTGA GGCCCGGACC TGCCCCGGGG CGAAGGGTAT GTGGCGAGAC AGAGCCCTGC     420

ACCCCTAATT CCCGGTGGAA AACTCCTGTT GCCGTTTCCC TCCACCGGCC TGGAGTCTCC     480

CAGTCTTGTC CCGGCAGTGC CGCCCTCCCC ACTAAGACCT AGGCGCAAAG CTTGGCTCA      540

TGGTTGACAG CTCAGAGAGA GAAAGATCTG AGGGAAG ATG GAT GCA AAA GCT CGA     595
                                        Met Asp Ala Lys Ala Arg
                                         1               5

AAT TGT TTG CTT CAA CAT AGA GAA GCT CTG GAA AAG GAC ATC AAG ACA      643
Asn Cys Leu Leu Gln His Arg Glu Ala Leu Glu Lys Asp Ile Lys Thr
             10                  15                  20

TCC TAC ATC ATG GAT CAC ATG ATT AGT GAT GGA TTT TTA ACA ATA TCA      691
Ser Tyr Ile Met Asp His Met Ile Ser Asp Gly Phe Leu Thr Ile Ser
             25                  30                  35

GAA GAG GAA AAA GTA AGA AAT GAG CCC ACT CAA CAG CAA AGA GCA GCT      739
Glu Glu Glu Lys Val Arg Asn Glu Pro Thr Gln Gln Gln Arg Ala Ala
         40                  45                  50

ATG CTG ATT AAA ATG ATA CTT AAA AAA GAT AAT GAT TCC TAC GTA TCA      787
Met Leu Ile Lys Met Ile Leu Lys Lys Asp Asn Asp Ser Tyr Val Ser
55                  60                  65                  70

TTC TAC AAT GCT CTA CTA CAT GAA GGA TAT AAA GAT CTT GCT GCC CTT      835
Phe Tyr Asn Ala Leu Leu His Glu Gly Tyr Lys Asp Leu Ala Ala Leu
             75                  80                  85

CTC CAT GAT GGC ATT CCT GTT GTC TCT TCT TCC AGT GTA AGG ACA GTC      883
Leu His Asp Gly Ile Pro Val Val Ser Ser Ser Ser Val Arg Thr Val
             90                  95                 100

CTG TGT GAA GGT GGA GTA CCA CAG AGG CCA GTT GTT TTT GTC ACA AGG      931
Leu Cys Glu Gly Gly Val Pro Gln Arg Pro Val Val Phe Val Thr Arg
            105                 110                 115

AAG AAG CTG GTG AAT GCA ATT CAG CAG AAG CTC TCC AAA TTG AAA GGT      979
Lys Lys Leu Val Asn Ala Ile Gln Gln Lys Leu Ser Lys Leu Lys Gly
        120                 125                 130

GAA CCA GGA TGG GTC ACC ATA CAT GGA ATG GCA GGC TGT GGG AAG TCT     1027
Glu Pro Gly Trp Val Thr Ile His Gly Met Ala Gly Cys Gly Lys Ser
135                 140                 145                 150

GTA TTA GCT GCA GAA GCT GTT AGA GAT CAT TCC CTT TTA GAA GGT TGT     1075
Val Leu Ala Ala Glu Ala Val Arg Asp His Ser Leu Leu Glu Gly Cys
                155                 160                 165

TTC CCA GGG GGA GTG CAT TGG GTT TCA GTT GGG AAA CAA GAC AAA TCT     1123
Phe Pro Gly Gly Val His Trp Val Ser Val Gly Lys Gln Asp Lys Ser
            170                 175                 180

GGG CTT CTG ATG AAA CTG CAG AAT CTT TGC ACA CGG TTG GAT CAG GAT     1171
Gly Leu Leu Met Lys Leu Gln Asn Leu Cys Thr Arg Leu Asp Gln Asp
        185                 190                 195

GAG AGT TTT TCC CAG AGG CTT CCA CTT AAT ATT GAA GAG GCT AAA GAC     1219
Glu Ser Phe Ser Gln Arg Leu Pro Leu Asn Ile Glu Glu Ala Lys Asp
        200                 205                 210

CGT CTC CGC ATT CTG ATG CTT CGC AAA CAC CCA AGG TCT CTC TTG ATC     1267
Arg Leu Arg Ile Leu Met Leu Arg Lys His Pro Arg Ser Leu Leu Ile
215                 220                 225                 230

TTG GAT GAT GTT TGG GAC TCT TGG GTG TTG AAA GCT TTT GAC AGT CAG     1315
Leu Asp Asp Val Trp Asp Ser Trp Val Leu Lys Ala Phe Asp Ser Gln
                235                 240                 245

TGT CAG ATT CTT CTT ACA ACC AGA GAC AAG AGT GTT ACA GAT TCA GTA     1363
Cys Gln Ile Leu Leu Thr Thr Arg Asp Lys Ser Val Thr Asp Ser Val
            250                 255                 260

ATG GGT CCT AAA TAT GTA GTC CCT GTG GAG AGT TCC TTA GGA AAG GAA     1411
Met Gly Pro Lys Tyr Val Val Pro Val Glu Ser Ser Leu Gly Lys Glu
        265                 270                 275
```

```
AAA GGA CTT GAA ATT TTA TCC CTT TTT GTT AAT ATG AAG AAG GCA GAT      1459
Lys Gly Leu Glu Ile Leu Ser Leu Phe Val Asn Met Lys Lys Ala Asp
    280                 285                 290

TTG CCA GAA CAA GCT CAT AGT ATT ATA AAA GAA TGT AAA GGC TCT CCC      1507
Leu Pro Glu Gln Ala His Ser Ile Ile Lys Glu Cys Lys Gly Ser Pro
295                 300                 305                 310

CTT GTA GTA TCT TTA ATT GGT GCA CTT TTA CGT GAT TTT CCC AAT CGC      1555
Leu Val Val Ser Leu Ile Gly Ala Leu Leu Arg Asp Phe Pro Asn Arg
                315                 320                 325

TGG GAG TAC TAC CTC AAA CAG CTT CAG AAT AAG CAG TTT AAG AGA ATA      1603
Trp Glu Tyr Tyr Leu Lys Gln Leu Gln Asn Lys Gln Phe Lys Arg Ile
            330                 335                 340

AGG AAA TCT TCG TCT TAT GAT TAT GAG GCT CTA GAT GAA GCC ATG TCT      1651
Arg Lys Ser Ser Ser Tyr Asp Tyr Glu Ala Leu Asp Glu Ala Met Ser
        345                 350                 355

ATA AGT GTT GAA ATG CTC AGA GAA GAC ATC AAA GAT TAT TAC ACA GAT      1699
Ile Ser Val Glu Met Leu Arg Glu Asp Ile Lys Asp Tyr Tyr Thr Asp
    360                 365                 370

CTT TCC ATC CTT CAG AAG GAC GTT AAG GTG CCT ACA AAG GTG TTA TGT      1747
Leu Ser Ile Leu Gln Lys Asp Val Lys Val Pro Thr Lys Val Leu Cys
375                 380                 385                 390

ATT CTC TGG GAC ATG GAA ACT GAA GAA GTT GAA GAC ATA CTG CAG GAG      1795
Ile Leu Trp Asp Met Glu Thr Glu Glu Val Glu Asp Ile Leu Gln Glu
                395                 400                 405

TTT GTA AAT AAG TCT CTT TTA TTC TGT GAT CGG AAT GGA AAG TCG TTT      1843
Phe Val Asn Lys Ser Leu Leu Phe Cys Asp Arg Asn Gly Lys Ser Phe
            410                 415                 420

CGT TAT TAT TTA CAT GAT CTT CAA GTA GAT TTT CTT ACA GAG AAG AAT      1891
Arg Tyr Tyr Leu His Asp Leu Gln Val Asp Phe Leu Thr Glu Lys Asn
        425                 430                 435

TGC AGC CAG CTT CAG GAT CTA CAT AAG AAG ATA ATC ACT CAG TTT CAG      1939
Cys Ser Gln Leu Gln Asp Leu His Lys Lys Ile Ile Thr Gln Phe Gln
    440                 445                 450

AGA TAT CAC CAG CCG CAT ACT CTT TCA CCA GAT CAG GAA GAC TGT ATG      1987
Arg Tyr His Gln Pro His Thr Leu Ser Pro Asp Gln Glu Asp Cys Met
455                 460                 465                 470

TAT TGG TAC AAC TTT CTG GCC TAT CAC ATG GCC AGT GCC AAG ATG CAC      2035
Tyr Trp Tyr Asn Phe Leu Ala Tyr His Met Ala Ser Ala Lys Met His
                475                 480                 485

AAG GAA CTT TGT GCT TTA ATG TTT TCC CTG GAT TGG ATT AAA GCA AAA      2083
Lys Glu Leu Cys Ala Leu Met Phe Ser Leu Asp Trp Ile Lys Ala Lys
            490                 495                 500

ACA GAA CTT GTA GGC CCT GCT CAT CTG ATT CAT GAA TTT GTG GAA TAC      2131
Thr Glu Leu Val Gly Pro Ala His Leu Ile His Glu Phe Val Glu Tyr
        505                 510                 515

AGA CAT ATA CTA GAT GAA AAG GAT TGT GCA GTC AGT GAG AAT TTT CAG      2179
Arg His Ile Leu Asp Glu Lys Asp Cys Ala Val Ser Glu Asn Phe Gln
    520                 525                 530

GAG TTT TTA TCT TTA AAT GGA CAC CTT CTT GGA CGA CAG CCA TTT CCT      2227
Glu Phe Leu Ser Leu Asn Gly His Leu Leu Gly Arg Gln Pro Phe Pro
535                 540                 545                 550

AAT ATT GTA CAA CTG GGT CTC TGT GAG CCG GAA ACT TCA GAA GTT TAT      2275
Asn Ile Val Gln Leu Gly Leu Cys Glu Pro Glu Thr Ser Glu Val Tyr
                555                 560                 565

CAG CAA GCT AAG CTG CAG GCC AAG CAG GAG GTC GAT AAT GGA ATG CTT      2323
Gln Gln Ala Lys Leu Gln Ala Lys Gln Glu Val Asp Asn Gly Met Leu
            570                 575                 580

TAC CTG GAA TGG ATA AAC AAA AAA AAC ATC ACG AAT CTT TCC CGC TTA      2371
Tyr Leu Glu Trp Ile Asn Lys Lys Asn Ile Thr Asn Leu Ser Arg Leu
```

|     |     |     |     |     |     |     |     |     |     |     |     |     |     |     |     |      |
|---|---|---|---|---|---|---|---|---|---|---|---|---|---|---|---|---|
|     |     |     | 585 |     |     |     | 590 |     |     |     | 595 |     |     |     |     |      |
| GTT | GTC | CGC | CCC | CAC | ACA | GAT | GCT | GTT | TAC | CAT | GCC | TGC | TTT | TCT | GAG | 2419 |
| Val | Val | Arg | Pro | His | Thr | Asp | Ala | Val | Tyr | His | Ala | Cys | Phe | Ser | Glu |      |
|     |     |     | 600 |     |     |     | 605 |     |     |     | 610 |     |     |     |     |      |
| GAT | GGT | CAG | AGA | ATA | GCT | TCT | TGT | GGA | GCT | GAT | AAA | ACC | TTA | CAG | GTG | 2467 |
| Asp | Gly | Gln | Arg | Ile | Ala | Ser | Cys | Gly | Ala | Asp | Lys | Thr | Leu | Gln | Val |      |
| 615 |     |     |     |     | 620 |     |     |     |     | 625 |     |     |     |     | 630 |      |
| TTC | AAA | GCT | GAA | ACA | GGA | GAG | AAA | CTT | CTA | GAA | ATC | AAG | GCT | CAT | GAG | 2515 |
| Phe | Lys | Ala | Glu | Thr | Gly | Glu | Lys | Leu | Leu | Glu | Ile | Lys | Ala | His | Glu |      |
|     |     |     |     |     | 635 |     |     |     |     | 640 |     |     |     |     | 645 |      |
| GAT | GAA | GTG | CTT | TGT | TGT | GCA | TTC | TCT | ACA | GAT | GAC | AGA | TTT | ATA | GCA | 2563 |
| Asp | Glu | Val | Leu | Cys | Cys | Ala | Phe | Ser | Thr | Asp | Asp | Arg | Phe | Ile | Ala |      |
|     |     |     |     | 650 |     |     |     |     | 655 |     |     |     |     | 660 |     |      |
| ACC | TGC | TCA | GTG | GAT | AAA | AAA | GTG | AAG | ATT | TGG | AAT | TCT | ATG | ACT | GGG | 2611 |
| Thr | Cys | Ser | Val | Asp | Lys | Lys | Val | Lys | Ile | Trp | Asn | Ser | Met | Thr | Gly |      |
|     |     |     | 665 |     |     |     | 670 |     |     |     | 675 |     |     |     |     |      |
| GAA | CTA | GTA | CAC | ACC | TAT | GAT | GAG | CAC | TCA | GAG | CAA | GTC | AAT | TGC | TGC | 2659 |
| Glu | Leu | Val | His | Thr | Tyr | Asp | Glu | His | Ser | Glu | Gln | Val | Asn | Cys | Cys |      |
|     |     | 680 |     |     |     |     | 685 |     |     |     |     | 690 |     |     |     |      |
| CAT | TTC | ACC | AAC | AGT | AGT | CAT | CAT | CTT | CTC | TTA | GCC | ACT | GGG | TCA | AGT | 2707 |
| His | Phe | Thr | Asn | Ser | Ser | His | His | Leu | Leu | Leu | Ala | Thr | Gly | Ser | Ser |      |
| 695 |     |     |     |     | 700 |     |     |     |     | 705 |     |     |     |     | 710 |      |
| GAC | TGC | TTC | CTC | AAA | CTT | TGG | GAT | TTG | AAT | CAA | AAA | GAA | TGT | CGA | AAT | 2755 |
| Asp | Cys | Phe | Leu | Lys | Leu | Trp | Asp | Leu | Asn | Gln | Lys | Glu | Cys | Arg | Asn |      |
|     |     |     |     | 715 |     |     |     |     | 720 |     |     |     |     | 725 |     |      |
| ACC | ATG | TTT | GGT | CAT | ACA | AAT | TCA | GTC | AAT | CAC | TGC | AGA | TTT | TCA | CCA | 2803 |
| Thr | Met | Phe | Gly | His | Thr | Asn | Ser | Val | Asn | His | Cys | Arg | Phe | Ser | Pro |      |
|     |     |     | 730 |     |     |     | 735 |     |     |     | 740 |     |     |     |     |      |
| GAT | GAT | AAG | CTT | TTG | GCT | AGT | TGT | TCA | GCT | GAT | GGA | ACC | TTA | AAG | CTT | 2851 |
| Asp | Asp | Lys | Leu | Leu | Ala | Ser | Cys | Ser | Ala | Asp | Gly | Thr | Leu | Lys | Leu |      |
|     |     | 745 |     |     |     |     | 750 |     |     |     |     | 755 |     |     |     |      |
| TGG | GAT | GCG | ACA | TCA | GCA | AAT | GAG | AGG | AAA | AGC | ATT | AAT | GTG | AAA | CAG | 2899 |
| Trp | Asp | Ala | Thr | Ser | Ala | Asn | Glu | Arg | Lys | Ser | Ile | Asn | Val | Lys | Gln |      |
| 760 |     |     |     |     | 765 |     |     |     |     | 770 |     |     |     |     |     |      |
| TTC | TTC | CTA | AAT | TTG | GAG | GAC | CCT | CAA | GAG | GAT | ATG | GAA | GTG | ATA | GTG | 2947 |
| Phe | Phe | Leu | Asn | Leu | Glu | Asp | Pro | Gln | Glu | Asp | Met | Glu | Val | Ile | Val |      |
| 775 |     |     |     |     | 780 |     |     |     |     | 785 |     |     |     |     | 790 |      |
| AAG | TGT | TGT | TCG | TGG | TCT | GCT | GAT | GGT | GCA | AGG | ATA | ATG | GTG | GCA | GCA | 2995 |
| Lys | Cys | Cys | Ser | Trp | Ser | Ala | Asp | Gly | Ala | Arg | Ile | Met | Val | Ala | Ala |      |
|     |     |     | 795 |     |     |     | 800 |     |     |     | 805 |     |     |     |     |      |
| AAA | AAT | AAA | ATC | TTT | TTG | TGG | AAT | ACA | GAC | TCA | CGT | TCA | AAG | GTG | GCT | 3043 |
| Lys | Asn | Lys | Ile | Phe | Leu | Trp | Asn | Thr | Asp | Ser | Arg | Ser | Lys | Val | Ala |      |
|     |     |     | 810 |     |     |     | 815 |     |     |     | 820 |     |     |     |     |      |
| GAT | TGC | AGA | GGA | CAT | TTA | AGT | TGG | GTT | CAT | GGT | GTG | ATG | TTT | TCT | CCT | 3091 |
| Asp | Cys | Arg | Gly | His | Leu | Ser | Trp | Val | His | Gly | Val | Met | Phe | Ser | Pro |      |
|     | 825 |     |     |     |     | 830 |     |     |     |     | 835 |     |     |     |     |      |
| GAT | GGA | TCA | TCA | TTT | TTG | ACA | TCT | TCT | GAT | GAC | CAG | ACA | ATC | AGG | CTC | 3139 |
| Asp | Gly | Ser | Ser | Phe | Leu | Thr | Ser | Ser | Asp | Asp | Gln | Thr | Ile | Arg | Leu |      |
| 840 |     |     |     |     | 845 |     |     |     |     | 850 |     |     |     |     |     |      |
| TGG | GAG | ACA | AAG | AAA | GTA | TGT | AAG | AAC | TCT | GCT | GTA | ATG | TTA | AAG | CAA | 3187 |
| Trp | Glu | Thr | Lys | Lys | Val | Cys | Lys | Asn | Ser | Ala | Val | Met | Leu | Lys | Gln |      |
| 855 |     |     |     |     | 860 |     |     |     |     | 865 |     |     |     |     | 870 |      |
| GAA | GTA | GAT | GTT | GTG | TTT | CAA | GAA | AAT | GAA | GTG | ATG | GTC | CTT | GCA | GTT | 3235 |
| Glu | Val | Asp | Val | Val | Phe | Gln | Glu | Asn | Glu | Val | Met | Val | Leu | Ala | Val |      |
|     |     |     |     | 875 |     |     |     |     | 880 |     |     |     |     | 885 |     |      |
| GAC | CAT | ATA | AGA | CGT | CTG | CAA | CTC | ATT | AAT | GGA | AGA | ACA | GGT | CAG | ATT | 3283 |
| Asp | His | Ile | Arg | Arg | Leu | Gln | Leu | Ile | Asn | Gly | Arg | Thr | Gly | Gln | Ile |      |
|     |     |     | 890 |     |     |     | 895 |     |     |     | 900 |     |     |     |     |      |
| GAT | TAT | CTG | ACT | GAA | GCT | CAA | GTT | AGC | TGC | TGT | TGC | TTA | AGT | CCA | CAT | 3331 |

```
               Asp Tyr Leu Thr Glu Ala Gln Val Ser Cys Cys Leu Ser Pro His
                       905                 910                 915

CTT CAG TAC ATT GCA TTT GGA GAT GAA AAT GGA GCC ATT GAG ATT TTA            3379
Leu Gln Tyr Ile Ala Phe Gly Asp Glu Asn Gly Ala Ile Glu Ile Leu
        920                 925                 930

GAA CTT GTA AAC AAT AGA ATC TTC CAG TCC AGG TTT CAG CAC AAG AAA            3427
Glu Leu Val Asn Asn Arg Ile Phe Gln Ser Arg Phe Gln His Lys Lys
935                 940                 945                 950

ACT GTA TGG CAC ATC CAG TTC ACA GCC GAT GAG AAG ACT CTT ATT TCA            3475
Thr Val Trp His Ile Gln Phe Thr Ala Asp Glu Lys Thr Leu Ile Ser
                955                 960                 965

AGT TCT GAT GAT GCT GAA ATT CAG GTA TGG AAT TGG CAA TTG GAC AAA            3523
Ser Ser Asp Asp Ala Glu Ile Gln Val Trp Asn Trp Gln Leu Asp Lys
        970                 975                 980

TGT ATC TTT CTA CGA GGC CAT CAG GAA ACA GTG AAA GAC TTT AGA CTC            3571
Cys Ile Phe Leu Arg Gly His Gln Glu Thr Val Lys Asp Phe Arg Leu
985                 990                 995

TTG AAA AAT TCA AGA CTG CTT TCT TGG TCA TTT GAT GGA ACA GTG AAG            3619
Leu Lys Asn Ser Arg Leu Leu Ser Trp Ser Phe Asp Gly Thr Val Lys
        1000                1005                1010

GTA TGG AAT ATT ATT ACT GGA AAT AAA GAA AAA GAC TTT GTC TGT CAC            3667
Val Trp Asn Ile Ile Thr Gly Asn Lys Glu Lys Asp Phe Val Cys His
1015                1020                1025                1030

CAG GGT ACA GTA CTT TCT TGT GAC ATT TCT CAC GAT GCT ACC AAG TTT            3715
Gln Gly Thr Val Leu Ser Cys Asp Ile Ser His Asp Ala Thr Lys Phe
        1035                1040                1045

TCA TCT ACC TCT GCT GAC AAG ACT GCA AAG ATC TGG AGT TTT GAT CTC            3763
Ser Ser Thr Ser Ala Asp Lys Thr Ala Lys Ile Trp Ser Phe Asp Leu
        1050                1055                1060

CTT TTG CCA CTT CAT GAA TTG AGG GGC CAC AAC GGC TGT GTG CGC TGC            3811
Leu Leu Pro Leu His Glu Leu Arg Gly His Asn Gly Cys Val Arg Cys
        1065                1070                1075

TCT GCC TTC TCT GTG GAC AGT ACC CTG CTG GCA ACG GGA GAT GAC AAT            3859
Ser Ala Phe Ser Val Asp Ser Thr Leu Leu Ala Thr Gly Asp Asp Asn
        1080                1085                1090

GGA GAA ATC AGG ATA TGG AAT GTC TCA AAC GGT GAG CTT CTT CAT TTG            3907
Gly Glu Ile Arg Ile Trp Asn Val Ser Asn Gly Glu Leu Leu His Leu
1095                1100                1105                1110

TGT GCT CCG CTT TCA GAA GAA GGA GCT GCT ACC CAT GGA GGC TGG GTG            3955
Cys Ala Pro Leu Ser Glu Glu Gly Ala Ala Thr His Gly Gly Trp Val
        1115                1120                1125

ACT GAC CTT TGC TTT TCT CCA GAT GGC AAA ATG CTT ATC TCT GCT GGA            4003
Thr Asp Leu Cys Phe Ser Pro Asp Gly Lys Met Leu Ile Ser Ala Gly
        1130                1135                1140

GGA TAT ATT AAG TGG TGG AAC GTT GTC ACT GGG GAA TCC TCA CAG ACC            4051
Gly Tyr Ile Lys Trp Trp Asn Val Val Thr Gly Glu Ser Ser Gln Thr
        1145                1150                1155

TTC TAC ACA AAT GGA ACC AAT CTT AAG AAA ATA CAC GTG TCC CCT GAC            4099
Phe Tyr Thr Asn Gly Thr Asn Leu Lys Lys Ile His Val Ser Pro Asp
        1160                1165                1170

TTC AAA ACA TAT GTG ACT GTG GAT AAT CTT GGT ATT TTA TAT ATT TTA            4147
Phe Lys Thr Tyr Val Thr Val Asp Asn Leu Gly Ile Leu Tyr Ile Leu
1175                1180                1185                1190

CAG ACT TTA GAA TAAAATAGTT AAGCATTAAT GTAGTTGAAC TTTTAAATT TTTGA           4204
Gln Thr Leu Glu
        1

ATTGGAAAAA AATTCTAATG AAACCCTGAT ATCAACTTTT TATAAAGCTC TTAATTGTTG          4264

TGCAGTATTG CATTCATTAC AAAAGTGTTT GTGGTTGGAT GAATAATATT AATGTAGCTT          4324
```

```
TTTCCCAAAT GAACATACCT TTAATCTTGT TTTTCATGAT CATCATTAAC AGTTTGTCCT  4384

TAGGATGCAA ATGAAAATGT GAATACATAC CTTGTTGTAC TGTTGGTAAA ATTCTGTCTT  4444

GATGCATTCA AAATGGTTGA CATAATTAAT GAGAAGAATT TGGAAGAAAT TGGTATTTTA  4504

ATACTGTCTG TATTTATTAC TGTTATGCAG GCTGTGCCTC AGGGTAGCAG TGGCCTGCTT  4564

TTTGAACCAC ACTTACCCCA AGGGGGTTTT GTTCTCCTAA ATACAATCTT AGAGGTTTTT  4624

TGCACTCTTT AAATTTGCTT TAAAAATATT GTGTCTGTGT GCATAGTCTG CAGCATTTCC  4684

TTTAATTGAC TCAATAAGTG AGTCTTGGAT TTAGCAGGCC CCCCACCTT TTTTTTTGT   4744

TTTTGGAGAC AGAGTCTTGC TTTGTTGCCA GGCTGGAGTG CAGTGGCGCG ATCTCGGCTC  4804

ACCACAATCG CTGCCTCCTG GGTTCAAGCA ATTCTCCTGC CTCAGCCTCC CGAGTAGCTG  4864

GGACTACAGG TGTGCGCACA TGCCAGGCTA ATTTTTGTAT TTTTAGTAGA GACGGGGTTT  4924

CACCATGTTG GCCGGGATGG TCTCGATCTC TTGACCTCAT GATCTACCCG CCTTGGCCTC  4984

CCAAAGTGCT GAGATTACAG GCGTGAGCCA CCGTGCCTGG CCAGGCCCCT TCTCTTTTAA  5044

TGGAGACAGG GTCTTGCACT ATCACCCAGG CTGGAGTGCA GTGGCATAAT CATACCTCAT  5104

TGCAGCCTCA GACTCCTGGG TTCAAGCAAT CCTCCTGCCT CAGCCTCCCA AGTAGCTGAG  5164

ACTGCAGGCA CGAGCCACCA CACCCAGCTA ATTTTTAAGT TTTCTTGTAG ACAGGGTC    5224

TCACTATGTT GTCTAGGCTG GTCTTGAACT CTTGGCCTCA AGTAATCCTC CTGCCTCAGC  5284

CTCCCAAAGT GTTGGGATTG CAGATATGAG CCACTGGCCT GGCCTTCAGC AGTTCTTTTT  5344

GTGAAGTAAA ACTTGTATGT TGGAAAGAGT AGATTTTATT GGTCTACCCT TTTCTCACTG  5404

TAGCTGCTGG CAGCCCTGTG CCATATCTGG ACTCTAGTTG TCAGTATCTG AGTTGGACAC  5464

TATTCCTGCT CCCTCTTGTT TCTTACATAT CAGACTTCTT ACTTGAATGA AACCTGATCT  5524

TTCCTAATCC TCACTTTTTT CTTTTTTAAA AAGCAGTTTC TCCACTGCTA AATGTTAGTC  5584

ATTGAGGTGG GGCCAATTTT AATCATAAGC CTTAATAAGA TTTTTCTAAG AAATGTGAAA  5644

TAGAACAATT TTCATCTAAT TCCATTTACT TTTAGATGAA TGGCATTGTG AATGCCATTC  5704

TTTTAATGAA TTTCAAGAGA ATTCTCTGGT TTTCTGTGTA ATTCCAGATG AGTCACTGTA  5764

ACTCTAGAAG ATTAACCTTC CAGCCAACCT ATTTTCCTTT CCCTTGTCTC TCTCATCCTC  5824

TTTTCCTTCC TTCTTTCCTT TCTCTTCTTT TATCTCCAAG GTTAATCAGG AAAAATAGCT  5884

TTTGACAGGG GAAAAAACTC AATAACTAGC TATTTTGAC CTCCTGATCA GGAACTTTAG   5944

TTGAAGCGTA AATCTAAAGA AACATTTTCT CTGAAATATA TTATTAAGGG CAATGGAGAT  6004

AAATTAATAG TAGATGTGGT TCCCAGAAAA TATAATCAAA ATTCAAAGAT TTTTTTTGTT  6064

TCTGTAACTG GAACTAAATC AAATGATTAC TAGTGTTAAT AGTAGATAAC TTGTTTTTAT  6124

TGTTGGTGCA TATTAGTATA ACTGTGGGGT AGGTCGGGGA GAGGGTAAGG GAATAGATCA  6184

CTCAGATGTA TTTTAGATAA GCTATTTAGC CTTTGATGGA ATCATAAATA CAGTGAATAC  6244

AATCCTTTGC ATTGTTAAGG AGGTTTTTTG TTTTTAAATG GTGGGTCAAG GAGCTAGTTT  6304

ACAGGCTTAC TGTGATTTAA GCAAATGTGA AAAGTGAAAC CTTAATTTTA TCAAAAGAAA  6364

TTTCTGTAAA TGGTATGTCT CCTTAGAATA CCCAAATCAT AATTTTATTT GTACACACTG  6424

TTAGGGGCTC ATCTCATGTA GGCAGAGTAT AAAGTATTAC CTTTTGGAAT TAAAAGCCAC  6484

TGACTGTTAT AAAGTATAAC AACACACATC AGGTTTTAAA AAGCCTTGAA TGGCCCTTGT  6544

CTTAAAAAGA AATTAGGAGC CAGGTGCGGT GGCACGTGCC TGTAGTCCCA GCTCCTTGGG  6604

AGGCTGAGAC AGGAGGATTC CTTGAGCCCT GGAGTTTGAG TCCAGCCTGG GTGACATAGC  6664

AAGACCCTGT CTTAAAAGAA AAATGGGAAG AAAGACAAGG TAACATGAAG AAAGAAGAGA  6724
```

-continued

```
TACCTAGTAT GATGGAGCTG CAAATTTCAT GGCAGTTCAT GCAGTCGGTC AAGAGGAGGA    6784

TTTTGTTTTG TAGTTTGCAG ATGAGCATTT CTAAAGCATT TTCCCTTGCT GTATTTTTTT    6844

GTATTATAAA TTACATTGGA CTTCATATAT ATAATTTTTT TTTACATTAT ATGTCTCTTG    6904

TATGTTTTGA AACTCTTGTA TTTATGATAT AGCTTATATG ATTTTTTTGC CTTGGTATAC    6964

ATTTTAAAAT ATGAATTTAA AAAATTTTTG TAAAAATAAA ATTCACAAAA TTGTTTTGAA    7024

AAACAAAAAA AAAAAAAA                                                  7042
```

(2) INFORMATION FOR SEQ ID NO:2:

(i) SEQUENCE CHARACTERISTICS:
        (A) LENGTH: 1194 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

```
Met Asp Ala Lys Ala Arg Asn Cys Leu Leu Gln His Arg Glu Ala Leu
 1               5                  10                  15

Glu Lys Asp Ile Lys Thr Ser Tyr Ile Met Asp His Met Ile Ser Asp
            20                  25                  30

Gly Phe Leu Thr Ile Ser Glu Glu Lys Val Arg Asn Glu Pro Thr
        35                  40                  45

Gln Gln Gln Arg Ala Ala Met Leu Ile Lys Met Ile Leu Lys Lys Asp
    50                  55                  60

Asn Asp Ser Tyr Val Ser Phe Tyr Asn Ala Leu Leu His Glu Gly Tyr
65                  70                  75                  80

Lys Asp Leu Ala Ala Leu Leu His Asp Gly Ile Pro Val Val Ser Ser
                85                  90                  95

Ser Ser Val Arg Thr Val Leu Cys Glu Gly Val Pro Gln Arg Pro
            100                 105                 110

Val Val Phe Val Thr Arg Lys Lys Leu Val Asn Ala Ile Gln Gln Lys
        115                 120                 125

Leu Ser Lys Leu Lys Gly Glu Pro Gly Trp Val Thr Ile His Gly Met
    130                 135                 140

Ala Gly Cys Gly Lys Ser Val Leu Ala Ala Glu Ala Val Arg Asp His
145                 150                 155                 160

Ser Leu Leu Glu Gly Cys Phe Pro Gly Gly Val His Trp Val Ser Val
                165                 170                 175

Gly Lys Gln Asp Lys Ser Gly Leu Leu Met Lys Leu Gln Asn Leu Cys
            180                 185                 190

Thr Arg Leu Asp Gln Asp Glu Ser Phe Ser Gln Arg Leu Pro Leu Asn
        195                 200                 205

Ile Glu Glu Ala Lys Asp Arg Leu Arg Ile Leu Met Leu Arg Lys His
    210                 215                 220

Pro Arg Ser Leu Leu Ile Leu Asp Asp Val Trp Asp Ser Trp Val Leu
225                 230                 235                 240

Lys Ala Phe Asp Ser Gln Cys Gln Ile Leu Leu Thr Thr Arg Asp Lys
                245                 250                 255

Ser Val Thr Asp Ser Val Met Gly Pro Lys Tyr Val Val Pro Val Glu
            260                 265                 270
```

```
Ser Ser Leu Gly Lys Glu Lys Gly Leu Glu Ile Leu Ser Leu Phe Val
        275                 280                 285
Asn Met Lys Lys Ala Asp Leu Pro Glu Gln Ala His Ser Ile Ile Lys
        290                 295                 300
Glu Cys Lys Gly Ser Pro Leu Val Val Ser Leu Ile Gly Ala Leu Leu
305                 310                 315                 320
Arg Asp Phe Pro Asn Arg Trp Glu Tyr Tyr Leu Lys Gln Leu Gln Asn
                325                 330                 335
Lys Gln Phe Lys Arg Ile Arg Lys Ser Ser Tyr Asp Tyr Glu Ala
        340                 345                 350
Leu Asp Glu Ala Met Ser Ile Ser Val Glu Met Leu Arg Glu Asp Ile
        355                 360                 365
Lys Asp Tyr Tyr Thr Asp Leu Ser Ile Leu Gln Lys Asp Val Lys Val
        370                 375                 380
Pro Thr Lys Val Leu Cys Ile Leu Trp Asp Met Glu Thr Glu Glu Val
385                 390                 395                 400
Glu Asp Ile Leu Gln Glu Phe Val Asn Lys Ser Leu Leu Phe Cys Asp
                405                 410                 415
Arg Asn Gly Lys Ser Phe Arg Tyr Tyr Leu His Asp Leu Gln Val Asp
            420                 425                 430
Phe Leu Thr Glu Lys Asn Cys Ser Gln Leu Gln Asp Leu His Lys Lys
        435                 440                 445
Ile Ile Thr Gln Phe Gln Arg Tyr His Gln Pro His Thr Leu Ser Pro
        450                 455                 460
Asp Gln Glu Asp Cys Met Tyr Trp Tyr Asn Phe Leu Ala Tyr His Met
465                 470                 475                 480
Ala Ser Ala Lys Met His Lys Glu Leu Cys Ala Leu Met Phe Ser Leu
                485                 490                 495
Asp Trp Ile Lys Ala Lys Thr Glu Leu Val Gly Pro Ala His Leu Ile
            500                 505                 510
His Glu Phe Val Glu Tyr Arg His Ile Leu Asp Glu Lys Asp Cys Ala
        515                 520                 525
Val Ser Glu Asn Phe Gln Glu Phe Leu Ser Leu Asn Gly His Leu Leu
        530                 535                 540
Gly Arg Gln Pro Phe Pro Asn Ile Val Gln Leu Gly Leu Cys Glu Pro
545                 550                 555                 560
Glu Thr Ser Glu Val Tyr Gln Gln Ala Lys Leu Gln Ala Lys Gln Glu
                565                 570                 575
Val Asp Asn Gly Met Leu Tyr Leu Glu Trp Ile Asn Lys Lys Asn Ile
            580                 585                 590
Thr Asn Leu Ser Arg Leu Val Val Arg Pro His Thr Asp Ala Val Tyr
        595                 600                 605
His Ala Cys Phe Ser Glu Asp Gly Gln Arg Ile Ala Ser Cys Gly Ala
        610                 615                 620
Asp Lys Thr Leu Gln Val Phe Lys Ala Glu Thr Gly Glu Lys Leu Leu
625                 630                 635                 640
Glu Ile Lys Ala His Glu Asp Glu Val Leu Cys Cys Ala Phe Ser Thr
                645                 650                 655
Asp Asp Arg Phe Ile Ala Thr Cys Ser Val Asp Lys Lys Val Lys Ile
            660                 665                 670
Trp Asn Ser Met Thr Gly Glu Leu Val His Thr Tyr Asp Glu His Ser
        675                 680                 685
Glu Gln Val Asn Cys Cys His Phe Thr Asn Ser Ser His His Leu Leu
```

-continued

```
            690                 695                 700
Leu Ala Thr Gly Ser Ser Asp Cys Phe Leu Lys Leu Trp Asp Leu Asn
705                 710                 715                 720
Gln Lys Glu Cys Arg Asn Thr Met Phe Gly His Thr Asn Ser Val Asn
                725                 730                 735
His Cys Arg Phe Ser Pro Asp Asp Lys Leu Leu Ala Ser Cys Ser Ala
                740                 745                 750
Asp Gly Thr Leu Lys Leu Trp Asp Ala Thr Ser Ala Asn Glu Arg Lys
                755                 760                 765
Ser Ile Asn Val Lys Gln Phe Phe Leu Asn Leu Glu Asp Pro Gln Glu
                770                 775                 780
Asp Met Glu Val Ile Val Lys Cys Cys Ser Trp Ser Ala Asp Gly Ala
785                 790                 795                 800
Arg Ile Met Val Ala Ala Lys Asn Lys Ile Phe Leu Trp Asn Thr Asp
                805                 810                 815
Ser Arg Ser Lys Val Ala Asp Cys Arg Gly His Leu Ser Trp Val His
                820                 825                 830
Gly Val Met Phe Ser Pro Asp Gly Ser Ser Phe Leu Thr Ser Ser Asp
                835                 840                 845
Asp Gln Thr Ile Arg Leu Trp Glu Thr Lys Lys Val Cys Lys Asn Ser
                850                 855                 860
Ala Val Met Leu Lys Gln Glu Val Asp Val Val Phe Gln Glu Asn Glu
865                 870                 875                 880
Val Met Val Leu Ala Val Asp His Ile Arg Arg Leu Gln Leu Ile Asn
                885                 890                 895
Gly Arg Thr Gly Gln Ile Asp Tyr Leu Thr Glu Ala Gln Val Ser Cys
                900                 905                 910
Cys Cys Leu Ser Pro His Leu Gln Tyr Ile Ala Phe Gly Asp Glu Asn
                915                 920                 925
Gly Ala Ile Glu Ile Leu Glu Leu Val Asn Asn Arg Ile Phe Gln Ser
                930                 935                 940
Arg Phe Gln His Lys Lys Thr Val Trp His Ile Gln Phe Thr Ala Asp
945                 950                 955                 960
Glu Lys Thr Leu Ile Ser Ser Ser Asp Asp Ala Glu Ile Gln Val Trp
                965                 970                 975
Asn Trp Gln Leu Asp Lys Cys Ile Phe Leu Arg Gly His Gln Glu Thr
                980                 985                 990
Val Lys Asp Phe Arg Leu Leu Lys Asn Ser Arg Leu Leu Ser Trp Ser
                995                 1000                1005
Phe Asp Gly Thr Val Lys Val Trp Asn Ile Ile Thr Gly Asn Lys Glu
        1010                1015                1020
Lys Asp Phe Val Cys His Gln Gly Thr Val Leu Ser Cys Asp Ile Ser
1025                1030                1035                1040
His Asp Ala Thr Lys Phe Ser Ser Thr Ser Ala Asp Lys Thr Ala Lys
                1045                1050                1055
Ile Trp Ser Phe Asp Leu Leu Leu Pro Leu His Glu Leu Arg Gly His
        1060                1065                1070
Asn Gly Cys Val Arg Cys Ser Ala Phe Ser Val Asp Ser Thr Leu Leu
        1075                1080                1085
Ala Thr Gly Asp Asp Asn Gly Glu Ile Arg Ile Trp Asn Val Ser Asn
        1090                1095                1100
Gly Glu Leu Leu His Leu Cys Ala Pro Leu Ser Glu Glu Gly Ala Ala
1105                1110                1115                1120
```

```
Thr His Gly Gly Trp Val Thr Asp Leu Cys Phe Ser Pro Asp Gly Lys
         1125                1130                1135

Met Leu Ile Ser Ala Gly Gly Tyr Ile Lys Trp Trp Asn Val Val Thr
         1140                1145                1150

Gly Glu Ser Ser Gln Thr Phe Tyr Thr Asn Gly Thr Asn Leu Lys Lys
         1155                1160                1165

Ile His Val Ser Pro Asp Phe Lys Thr Tyr Val Thr Val Asp Asn Leu
    1170                1175                1180

Gly Ile Leu Tyr Ile Leu Gln Thr Leu Glu
1185                1190                1194

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:3:

AARGTNMGNA AYGARCCNAC                                                    20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:4:

ATTTAGGTGA CACTATAGAA                                                    20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:5:

AAYGARCCNA CNCAACAACA                                                    20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:6:

TTYTGYTGDA TNGCRTTCAC                                                    20

(2) INFORMATION FOR SEQ ID NO:7:
```

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:7:

ACATCACGAA TCTTTCCCGC                                          20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:8:

AACACTTCAC TATCACTTCC                                          20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:9:

ACATCACGAA TCTTTCCCGC                                          20

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:10:

CAACACTTCA CTATCACTTC C                                        21

(2) INFORMATION FOR SEQ ID NO:11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:11:

GCAAAAGCTC GAAATCATAT GCTTCAACAT AGAG                          34

(2) INFORMATION FOR SEQ ID NO:12:

(i) SEQUENCE CHARACTERISTICS:
        (A) LENGTH: 31 base pairs
        (B) TYPE: nucleic acid
        (C) STRANDEDNESS: single (D) TOPOLOGY: linear (ii) MOLECULE TYPE: Other (xi) SEQUENCE DESCRIPTION: SEQ ID NO:12:

TCGCGGCCGC CTCGAGGGCT CTGGTTGTAA G                                31

(2) INFORMATION FOR SEQ ID NO:13:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:13:

TAATGATTCC TACGTATCAT TCTACAATGC                                  30

(2) INFORMATION FOR SEQ ID NO:14:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:14:

GAATGATCTC TAACAGCTTC                                             20

(2) INFORMATION FOR SEQ ID NO:15:

(i) SEQUENCE CHARACTERISTICS:
            (A) LENGTH: 7075 base pairs
            (B) TYPE: nucleic acid
            (C) STRANDEDNESS: double
            (D) TOPOLOGY: linear (ii) MOLECULE TYPE: cDNA (ix) FEATURE:
            (A) NAME/KEY: Coding Sequence
            (B) LOCATION: 578...4192
            (D) OTHER INFORMATION:

(xi) SEQUENCE DESCRIPTION: SEQ ID NO:15:

AAGAAGAGGT AGCGAGTGGA CGTGACTGCT CTATCCCGGG CAAAAGGGAT AGAACCAGAG     60

GTGGGGAGTC TGGGCAGTCG GCGACCCGCG AAGACTTGAG GTGCCGCAGC GGCATCCGGA    120

GTAGCGCCGG GCTCCCTCCG GGGTGCAGCC GCCGTCGGGG GAAGGGCGCC ACAGGCCGGG    180

AAGACCTCCT CCCTTTGTGT CCAGTAGTGG GGTCCACCGG AGGGCGGCCC GTGGGCCGGG    240

CCTCACCGCG GCGCTCCGGG ACTGTGGGGT CAGGCTGCGT TGGGTGGACG CCCACCTCGC    300

CAACCTTCGG AGGTCCCTGG GGGTCTTCGT GCGCCCCGGG GCTGCAGAGA TCCAGGGGAG    360

GCGCCTGTGA GGCCCGGACC TGCCCCGGGG CGAAGGGTAT GTGGCGAGAC AGAGCCCTGC    420

ACCCCTAATT CCCGGTGGAA AACTCCTGTT GCCGTTTCCC TCCACCGGCC TGGAGTCTCC    480

CAGTCTTGTC CCGGCAGTGC CGCCCTCCCC ACTAAGACCT AGGCGCAAAG GCTTGGCTCA    540

TGGTTGACAG CTCAGAGAGA GAAAGATCTG AGGGAAG ATG GAT GCA AAA GCT CGA    595
                                            Met Asp Ala Lys Ala Arg
                                              1               5

AAT TGT TTG CTT CAA CAT AGA GAA GCT CTG GAA AAG GAC ATC AAG ACA    643

```
Asn Cys Leu Leu Gln His Arg Glu Ala Leu Glu Lys Asp Ile Lys Thr
         10                  15                  20

TCC TAC ATC ATG GAT CAC ATG ATT AGT GAT GGA TTT TTA ACA ATA TCA      691
Ser Tyr Ile Met Asp His Met Ile Ser Asp Gly Phe Leu Thr Ile Ser
            25                  30                  35

GAA GAG GAA AAA GTA AGA AAT GAG CCC ACT CAA CAG CAA AGA GCA GCT      739
Glu Glu Glu Lys Val Arg Asn Glu Pro Thr Gln Gln Gln Arg Ala Ala
 40                  45                  50

ATG CTG ATT AAA ATG ATA CTT AAA AAA GAT AAT GAT TCC TAC GTA TCA      787
Met Leu Ile Lys Met Ile Leu Lys Lys Asp Asn Asp Ser Tyr Val Ser
 55                  60                  65                  70

TTC TAC AAT GCT CTA CTA CAT GAA GGA TAT AAA GAT CTT GCT GCC CTT      835
Phe Tyr Asn Ala Leu Leu His Glu Gly Tyr Lys Asp Leu Ala Ala Leu
                 75                  80                  85

CTC CAT GAT GGC ATT CCT GTT GTC TCT TCT TCC AGT GGT AAA GAT TCA      883
Leu His Asp Gly Ile Pro Val Val Ser Ser Ser Ser Gly Lys Asp Ser
                     90                  95                 100

GTT AGT GGA ATA ACT TCG TAT GTA AGG ACA GTC CTG TGT GAA GGT GGA      931
Val Ser Gly Ile Thr Ser Tyr Val Arg Thr Val Leu Cys Glu Gly Gly
            105                 110                 115

GTA CCA CAG AGG CCA GTT GTT TTT GTC ACA AGG AAG AAG CTG GTG AAT      979
Val Pro Gln Arg Pro Val Val Phe Val Thr Arg Lys Lys Leu Val Asn
120                 125                 130

GCA ATT CAG CAG AAG CTC TCC AAA TTG AAA GGT GAA CCA GGA TGG GTC     1027
Ala Ile Gln Gln Lys Leu Ser Lys Leu Lys Gly Glu Pro Gly Trp Val
135                 140                 145                 150

ACC ATA CAT GGA ATG GCA GGC TGT GGG AAG TCT GTA TTA GCT GCA GAA     1075
Thr Ile His Gly Met Ala Gly Cys Gly Lys Ser Val Leu Ala Ala Glu
                155                 160                 165

GCT GTT AGA GAT CAT TCC CTT TTA GAA GGT TGT TTC CCA GGG GGA GTG     1123
Ala Val Arg Asp His Ser Leu Leu Glu Gly Cys Phe Pro Gly Gly Val
            170                 175                 180

CAT TGG GTT TCA GTT GGG AAA CAA GAC AAA TCT GGG CTT CTG ATG AAA     1171
His Trp Val Ser Val Gly Lys Gln Asp Lys Ser Gly Leu Leu Met Lys
        185                 190                 195

CTG CAG AAT CTT TGC ACA CGG TTG GAT CAG GAT GAG AGT TTT TCC CAG     1219
Leu Gln Asn Leu Cys Thr Arg Leu Asp Gln Asp Glu Ser Phe Ser Gln
200                 205                 210

AGG CTT CCA CTT AAT ATT GAA GAG GCT AAA GAC CGT CTC CGC ATT CTG     1267
Arg Leu Pro Leu Asn Ile Glu Glu Ala Lys Asp Arg Leu Arg Ile Leu
215                 220                 225                 230

ATG CTT CGC AAA CAC CCA AGG TCT CTC TTG ATC TTG GAT GAT GTT TGG     1315
Met Leu Arg Lys His Pro Arg Ser Leu Leu Ile Leu Asp Asp Val Trp
                235                 240                 245

GAC TCT TGG GTG TTG AAA GCT TTT GAC AGT CAG TGT CAG ATT CTT CTT     1363
Asp Ser Trp Val Leu Lys Ala Phe Asp Ser Gln Cys Gln Ile Leu Leu
            250                 255                 260

ACA ACC AGA GAC AAG AGT GTT ACA GAT TCA GTA ATG GGT CCT AAA TAT     1411
Thr Thr Arg Asp Lys Ser Val Thr Asp Ser Val Met Gly Pro Lys Tyr
        265                 270                 275

GTA GTC CCT GTG GAG AGT TCC TTA GGA AAG GAA AAA GGA CTT GAA ATT     1459
Val Val Pro Val Glu Ser Ser Leu Gly Lys Glu Lys Gly Leu Glu Ile
    280                 285                 290

TTA TCC CTT TTT GTT AAT ATG AAG AAG GCA GAT TTG CCA GAA CAA GCT     1507
Leu Ser Leu Phe Val Asn Met Lys Lys Ala Asp Leu Pro Glu Gln Ala
295                 300                 305                 310

CAT AGT ATT ATA AAA GAA TGT AAA GGC TCT CCC CTT GTA GTA TCT TTA     1555
His Ser Ile Ile Lys Glu Cys Lys Gly Ser Pro Leu Val Val Ser Leu
                315                 320                 325
```

```
ATT GGT GCA CTT TTA CGT GAT TTT CCC AAT CGC TGG GAG TAC TAC CTC    1603
Ile Gly Ala Leu Leu Arg Asp Phe Pro Asn Arg Trp Glu Tyr Tyr Leu
            330             335             340

AAA CAG CTT CAG AAT AAG CAG TTT AAG AGA ATA AGG AAA TCT TCG TCT    1651
Lys Gln Leu Gln Asn Lys Gln Phe Lys Arg Ile Arg Lys Ser Ser Ser
            345             350             355

TAT GAT TAT GAG GCT CTA GAT GAA GCC ATG TCT ATA AGT GTT GAA ATG    1699
Tyr Asp Tyr Glu Ala Leu Asp Glu Ala Met Ser Ile Ser Val Glu Met
        360             365             370

CTC AGA GAA GAC ATC AAA GAT TAT TAC ACA GAT CTT TCC ATC CTT CAG    1747
Leu Arg Glu Asp Ile Lys Asp Tyr Tyr Thr Asp Leu Ser Ile Leu Gln
375             380             385             390

AAG GAC GTT AAG GTG CCT ACA AAG GTG TTA TGT ATT CTC TGG GAC ATG    1795
Lys Asp Val Lys Val Pro Thr Lys Val Leu Cys Ile Leu Trp Asp Met
            395             400             405

GAA ACT GAA GAA GTT GAA GAC ATA CTG CAG GAG TTT GTA AAT AAG TCT    1843
Glu Thr Glu Glu Val Glu Asp Ile Leu Gln Glu Phe Val Asn Lys Ser
            410             415             420

CTT TTA TTC TGT GAT CGG AAT GGA AAG TCG TTT CGT TAT TAT TTA CAT    1891
Leu Leu Phe Cys Asp Arg Asn Gly Lys Ser Phe Arg Tyr Tyr Leu His
            425             430             435

GAT CTT CAA GTA GAT TTT CTT ACA GAG AAG AAT TGC AGC CAG CTT CAG    1939
Asp Leu Gln Val Asp Phe Leu Thr Glu Lys Asn Cys Ser Gln Leu Gln
        440             445             450

GAT CTA CAT AAG AAG ATA ATC ACT CAG TTT CAG AGA TAT CAC CAG CCG    1987
Asp Leu His Lys Lys Ile Ile Thr Gln Phe Gln Arg Tyr His Gln Pro
455             460             465             470

CAT ACT CTT TCA CCA GAT CAG GAA GAC TGT ATG TAT TGG TAC AAC TTT    2035
His Thr Leu Ser Pro Asp Gln Glu Asp Cys Met Tyr Trp Tyr Asn Phe
            475             480             485

CTG GCC TAT CAC ATG GCC AGT GCC AAG ATG CAC AAG GAA CTT TGT GCT    2083
Leu Ala Tyr His Met Ala Ser Ala Lys Met His Lys Glu Leu Cys Ala
            490             495             500

TTA ATG TTT TCC CTG GAT TGG ATT AAA GCA AAA ACA GAA CTT GTA GGC    2131
Leu Met Phe Ser Leu Asp Trp Ile Lys Ala Lys Thr Glu Leu Val Gly
            505             510             515

CCT GCT CAT CTG ATT CAT GAA TTT GTG GAA TAC AGA CAT ATA CTA GAT    2179
Pro Ala His Leu Ile His Glu Phe Val Glu Tyr Arg His Ile Leu Asp
            520             525             530

GAA AAG GAT TGT GCA GTC AGT GAG AAT TTT CAG GAG TTT TTA TCT TTA    2227
Glu Lys Asp Cys Ala Val Ser Glu Asn Phe Gln Glu Phe Leu Ser Leu
535             540             545             550

AAT GGA CAC CTT CTT GGA CGA CAG CCA TTT CCT AAT ATT GTA CAA CTG    2275
Asn Gly His Leu Leu Gly Arg Gln Pro Phe Pro Asn Ile Val Gln Leu
            555             560             565

GGT CTC TGT GAG CCG GAA ACT TCA GAA GTT TAT CAG CAA GCT AAG CTG    2323
Gly Leu Cys Glu Pro Glu Thr Ser Glu Val Tyr Gln Gln Ala Lys Leu
            570             575             580

CAG GCC AAG CAG GAG GTC GAT AAT GGA ATG CTT TAC CTG GAA TGG ATA    2371
Gln Ala Lys Gln Glu Val Asp Asn Gly Met Leu Tyr Leu Glu Trp Ile
            585             590             595

AAC AAA AAA AAC ATC ACG AAT CTT TCC CGC TTA GTT GTC CGC CCC CAC    2419
Asn Lys Lys Asn Ile Thr Asn Leu Ser Arg Leu Val Val Arg Pro His
            600             605             610

ACA GAT GCT GTT TAC CAT GCC TGC TTT TCT GAG GAT GGT CAG AGA ATA    2467
Thr Asp Ala Val Tyr His Ala Cys Phe Ser Glu Asp Gly Gln Arg Ile
615             620             625             630

GCT TCT TGT GGA GCT GAT AAA ACC TTA CAG GTG TTC AAA GCT GAA ACA    2515
Ala Ser Cys Gly Ala Asp Lys Thr Leu Gln Val Phe Lys Ala Glu Thr
            635             640             645
```

```
GGA GAG AAA CTT CTA GAA ATC AAG GCT CAT GAG GAT GAA GTG CTT TGT    2563
Gly Glu Lys Leu Leu Glu Ile Lys Ala His Glu Asp Glu Val Leu Cys
            650                 655                 660

TGT GCA TTC TCT ACA GAT GAC AGA TTT ATA GCA ACC TGC TCA GTG GAT    2611
Cys Ala Phe Ser Thr Asp Asp Arg Phe Ile Ala Thr Cys Ser Val Asp
            665                 670                 675

AAA AAA GTG AAG ATT TGG AAT TCT ATG ACT GGG GAA CTA GTA CAC ACC    2659
Lys Lys Val Lys Ile Trp Asn Ser Met Thr Gly Glu Leu Val His Thr
680                 685                 690

TAT GAT GAG CAC TCA GAG CAA GTC AAT TGC TGC CAT TTC ACC AAC AGT    2707
Tyr Asp Glu His Ser Glu Gln Val Asn Cys Cys His Phe Thr Asn Ser
695                 700                 705                 710

AGT CAT CAT CTT CTC TTA GCC ACT GGG TCA AGT GAC TGC TTC CTC AAA    2755
Ser His His Leu Leu Leu Ala Thr Gly Ser Ser Asp Cys Phe Leu Lys
            715                 720                 725

CTT TGG GAT TTG AAT CAA AAA GAA TGT CGA AAT ACC ATG TTT GGT CAT    2803
Leu Trp Asp Leu Asn Gln Lys Glu Cys Arg Asn Thr Met Phe Gly His
            730                 735                 740

ACA AAT TCA GTC AAT CAC TGC AGA TTT TCA CCA GAT GAT AAG CTT TTG    2851
Thr Asn Ser Val Asn His Cys Arg Phe Ser Pro Asp Asp Lys Leu Leu
            745                 750                 755

GCT AGT TGT TCA GCT GAT GGA ACC TTA AAG CTT TGG GAT GCG ACA TCA    2899
Ala Ser Cys Ser Ala Asp Gly Thr Leu Lys Leu Trp Asp Ala Thr Ser
760                 765                 770

GCA AAT GAG AGG AAA AGC ATT AAT GTG AAA CAG TTC TTC CTA AAT TTG    2947
Ala Asn Glu Arg Lys Ser Ile Asn Val Lys Gln Phe Phe Leu Asn Leu
775                 780                 785                 790

GAG GAC CCT CAA GAG GAT ATG GAA GTG ATA GTG AAG TGT TGT TCG TGG    2995
Glu Asp Pro Gln Glu Asp Met Glu Val Ile Val Lys Cys Cys Ser Trp
            795                 800                 805

TCT GCT GAT GGT GCA AGG ATA ATG GTG GCA GCA AAA AAT AAA ATC TTT    3043
Ser Ala Asp Gly Ala Arg Ile Met Val Ala Ala Lys Asn Lys Ile Phe
            810                 815                 820

TTG TGG AAT ACA GAC TCA CGT TCA AAG GTG GCT GAT TGC AGA GGA CAT    3091
Leu Trp Asn Thr Asp Ser Arg Ser Lys Val Ala Asp Cys Arg Gly His
            825                 830                 835

TTA AGT TGG GTT CAT GGT GTG ATG TTT TCT CCT GAT GGA TCA TCA TTT    3139
Leu Ser Trp Val His Gly Val Met Phe Ser Pro Asp Gly Ser Ser Phe
840                 845                 850

TTG ACA TCT TCT GAT GAC CAG ACA ATC AGG CTC TGG GAG ACA AAG AAA    3187
Leu Thr Ser Ser Asp Asp Gln Thr Ile Arg Leu Trp Glu Thr Lys Lys
855                 860                 865                 870

GTA TGT AAG AAC TCT GCT GTA ATG TTA AAG CAA GAA GTA GAT GTT GTG    3235
Val Cys Lys Asn Ser Ala Val Met Leu Lys Gln Glu Val Asp Val Val
            875                 880                 885

TTT CAA GAA AAT GAA GTG ATG GTC CTT GCA GTT GAC CAT ATA AGA CGT    3283
Phe Gln Glu Asn Glu Val Met Val Leu Ala Val Asp His Ile Arg Arg
            890                 895                 900

CTG CAA CTC ATT AAT GGA AGA ACA GGT CAG ATT GAT TAT CTG ACT GAA    3331
Leu Gln Leu Ile Asn Gly Arg Thr Gly Gln Ile Asp Tyr Leu Thr Glu
            905                 910                 915

GCT CAA GTT AGC TGC TGT TGC TTA AGT CCA CAT CTT CAG TAC ATT GCA    3379
Ala Gln Val Ser Cys Cys Cys Leu Ser Pro His Leu Gln Tyr Ile Ala
            920                 925                 930

TTT GGA GAT GAA AAT GGA GCC ATT GAG ATT TTA GAA CTT GTA AAC AAT    3427
Phe Gly Asp Glu Asn Gly Ala Ile Glu Ile Leu Glu Leu Val Asn Asn
935                 940                 945                 950

AGA ATC TTC CAG TCC AGG TTT CAG CAC AAG AAA ACT GTA TGG CAC ATC    3475
Arg Ile Phe Gln Ser Arg Phe Gln His Lys Lys Thr Val Trp His Ile
```

-continued

```
            955                 960                 965
CAG TTC ACA GCC GAT GAG AAG ACT CTT ATT TCA AGT TCT GAT GAT GCT       3523
Gln Phe Thr Ala Asp Glu Lys Thr Leu Ile Ser Ser Ser Asp Asp Ala
                970                 975                 980

GAA ATT CAG GTA TGG AAT TGG CAA TTG GAC AAA TGT ATC TTT CTA CGA       3571
Glu Ile Gln Val Trp Asn Trp Gln Leu Asp Lys Cys Ile Phe Leu Arg
            985                 990                 995

GGC CAT CAG GAA ACA GTG AAA GAC TTT AGA CTC TTG AAA AAT TCA AGA       3619
Gly His Gln Glu Thr Val Lys Asp Phe Arg Leu Leu Lys Asn Ser Arg
       1000                1005                1010

CTG CTT TCT TGG TCA TTT GAT GGA ACA GTG AAG GTA TGG AAT ATT ATT       3667
Leu Leu Ser Trp Ser Phe Asp Gly Thr Val Lys Val Trp Asn Ile Ile
1015                1020                1025                1030

ACT GGA AAT AAA GAA AAA GAC TTT GTC TGT CAC CAG GGT ACA GTA CTT       3715
Thr Gly Asn Lys Glu Lys Asp Phe Val Cys His Gln Gly Thr Val Leu
                1035                1040                1045

TCT TGT GAC ATT TCT CAC GAT GCT ACC AAG TTT TCA TCT ACC TCT GCT       3763
Ser Cys Asp Ile Ser His Asp Ala Thr Lys Phe Ser Ser Thr Ser Ala
            1050                1055                1060

GAC AAG ACT GCA AAG ATC TGG AGT TTT GAT CTC CTT TTG CCA CTT CAT       3811
Asp Lys Thr Ala Lys Ile Trp Ser Phe Asp Leu Leu Leu Pro Leu His
       1065                1070                1075

GAA TTG AGG GGC CAC AAC GGC TGT GTG CGC TGC TCT GCC TTC TCT GTG       3859
Glu Leu Arg Gly His Asn Gly Cys Val Arg Cys Ser Ala Phe Ser Val
   1080                1085                1090

GAC AGT ACC CTG CTG GCA ACG GGA GAT GAC AAT GGA GAA ATC AGG ATA       3907
Asp Ser Thr Leu Leu Ala Thr Gly Asp Asp Asn Gly Glu Ile Arg Ile
1095                1100                1105                1110

TGG AAT GTC TCA AAC GGT GAG CTT CTT CAT TTG TGT GCT CCG CTT TCA       3955
Trp Asn Val Ser Asn Gly Glu Leu Leu His Leu Cys Ala Pro Leu Ser
                1115                1120                1125

GAA GAA GGA GCT GCT ACC CAT GGA GGC TGG GTG ACT GAC CTT TGC TTT       4003
Glu Glu Gly Ala Ala Thr His Gly Gly Trp Val Thr Asp Leu Cys Phe
            1130                1135                1140

TCT CCA GAT GGC AAA ATG CTT ATC TCT GCT GGA GGA TAT ATT AAG TGG       4051
Ser Pro Asp Gly Lys Met Leu Ile Ser Ala Gly Gly Tyr Ile Lys Trp
       1145                1150                1155

TGG AAC GTT GTC ACT GGG GAA TCC TCA CAG ACC TTC TAC ACA AAT GGA       4099
Trp Asn Val Val Thr Gly Glu Ser Ser Gln Thr Phe Tyr Thr Asn Gly
   1160                1165                1170

ACC AAT CTT AAG AAA ATA CAC GTG TCC CCT GAC TTC AAA ACA TAT GTG       4147
Thr Asn Leu Lys Lys Ile His Val Ser Pro Asp Phe Lys Thr Tyr Val
1175                1180                1185                1190

ACT GTG GAT AAT CTT GGT ATT TTA TAT ATT TTA CAG ACT TTA GAA TAAAA    4197
Thr Val Asp Asn Leu Gly Ile Leu Tyr Ile Leu Gln Thr Leu Glu
                1195                1200                1205

TAGTTAAGCA TTAATGTAGT TGAACTTTTT AAATTTTTGA ATTGGAAAAA AATTCTAATG    4257

AAACCCTGAT ATCAACTTTT TATAAAGCTC TTAATTGTTG TGCAGTATTG CATTCATTAC    4317

AAAAGTGTTT GTGGTTGGAT GAATAATATT AATGTAGCTT TTTCCCAAAT GAACATACCT    4377

TTAATCTTGT TTTTCATGAT CATCATTAAC AGTTTGTCCT TAGGATGCAA ATGAAAATGT    4437

GAATACATAC CTTGTTGTAC TGTTGGTAAA ATTCTGTCTT GATGCATTCA AAATGGTTGA    4497

CATAATTAAT GAGAAGAATT TGGAAGAAAT TGGTATTTTA ATACTGTCTG TATTTATTAC    4557

TGTTATGCAG GCTGTGCCTC AGGGTAGCAG TGGCCTGCTT TTTGAACCAC ACTTACCCCA    4617

AGGGGGTTTT GTTCTCCTAA ATACAATCTT AGAGGTTTTT TGCACTCTTT AAATTTGCTT    4677

TAAAAATATT GTGTCTGTGT GCATAGTCTG CAGCATTTCC TTTAATTGAC TCAATAAGTG    4737
```

```
AGTCTTGGAT TTAGCAGGCC CCCCCACCTT TTTTTTTTGT TTTTGGAGAC AGAGTCTTGC  4797
TTTGTTGCCA GGCTGGAGTG CAGTGGCGCG ATCTCGGCTC ACCACAATCG CTGCCTCCTG  4857
GGTTCAAGCA ATTCTCCTGC CTCAGCCTCC CGAGTAGCTG GGACTACAGG TGTGCGCACA  4917
TGCCAGGCTA ATTTTTGTAT TTTTAGTAGA GACGGGGTTT CACCATGTTG GCCGGGATGG  4977
TCTCGATCTC TTGACCTCAT GATCTACCCG CCTTGGCCTC CCAAAGTGCT GAGATTACAG  5037
GCGTGAGCCA CCGTGCCTGG CCAGGCCCCT TCTCTTTTAA TGGAGACAGG GTCTTGCACT  5097
ATCACCCAGG CTGGAGTGCA GTGGCATAAT CATACCTCAT TGCAGCCTCA GACTCCTGGG  5157
TTCAAGCAAT CCTCCTGCCT CAGCCTCCCA AGTAGCTGAG ACTGCAGGCA CGAGCCACCA  5217
CACCCAGCTA ATTTTTAAGT TTTCTTGTAG AGACAGGGTC TCACTATGTT GTCTAGGCTG  5277
GTCTTGAACT CTTGGCCTCA AGTAATCCTC CTGCCTCAGC CTCCCAAAGT GTTGGGATTG  5337
CAGATATGAG CCACTGGCCT GGCCTTCAGC AGTTCTTTTT GTGAAGTAAA ACTTGTATGT  5397
TGGAAAGAGT AGATTTTATT GGTCTACCCT TTTCTCACTG TAGCTGCTGG CAGCCCTGTG  5457
CCATATCTGG ACTCAGTTG TCAGTATCTG AGTTGGACAC TATTCCTGCT CCCTCTTGTT  5517
TCTTACATAT CAGACTTCTT ACTTGAATGA AACCTGATCT TTCCTAATCC TCACTTTTTT  5577
CTTTTTTAAA AAGCAGTTTC TCCACTGCTA AATGTTAGTC ATTGAGGTGG GGCCAATTTT  5637
AATCATAAGC CTTAATAAGA TTTTTCTAAG AAATGTGAAA TAGAACAATT TTCATCTAAT  5697
TCCATTTACT TTTAGATGAA TGGCATTGTG AATGCCATTC TTTTAATGAA TTTCAAGAGA  5757
ATTCTCTGGT TTTCTGTGTA ATTCCAGATG AGTCACTGTA ACTCTAGAAG ATTAACCTTC  5817
CAGCCAACCT ATTTTCCTTT CCCTTGTCTC TCTCATCCTC TTTTCCTTCC TTCTTTCCTT  5877
TCTCTTCTTT TATCTCCAAG GTTAATCAGG AAAAATAGCT TTTGACAGGG GAAAAAACTC  5937
AATAACTAGC TATTTTTGAC CTCCTGATCA GGAACTTTAG TTGAAGCGTA AATCTAAAGA  5997
AACATTTCT CTGAAATATA TTATTAAGGG CAATGGAGAT AAATTAATAG TAGATGTGGT  6057
TCCCAGAAAA TATAATCAAA ATTCAAAGAT TTTTTTTGTT TCTGTAACTG GAACTAAATC  6117
AAATGATTAC TAGTGTTAAT AGTAGATAAC TTGTTTTTAT TGTTGGTGCA TATTAGTATA  6177
ACTGTGGGGT AGGTCGGGGA GAGGGTAAGG GAATAGATCA CTCAGATGTA TTTTAGATAA  6237
GCTATTTAGC CTTTGATGGA ATCATAAATA CAGTGAATAC AATCCTTTGC ATTGTTAAGG  6297
AGGTTTTTTG TTTTTAAATG GTGGGTCAAG GAGCTAGTTT ACAGGCTTAC TGTGATTTAA  6357
GCAAATGTGA AAAGTGAAAC CTTAATTTTA TCAAAAGAAA TTTCTGTAAA TGGTATGTCT  6417
CCTTAGAATA CCCAAATCAT AATTTTATTT GTACACACTG TTAGGGGCTC ATCTCATGTA  6477
GGCAGAGTAT AAAGTATTAC CTTTTGGAAT TAAAAGCCAC TGACTGTTAT AAAGTATAAC  6537
AACACACATC AGGTTTTAAA AAGCCTTGAA TGGCCCTTGT CTTAAAAAGA AATTAGGAGC  6597
CAGGTGCGGT GGCACGTGCC TGTAGTCCCA GCTCCTTGGG AGGCTGAGAC AGGAGGATTC  6657
CTTGAGCCCT GGAGTTTGAG TCCAGCCTGG GTGACATAGC AAGACCCTGT CTTAAAAGAA  6717
AAATGGGAAG AAAGACAAGG TAACATGAAG AAAGAAGAGA TACCTAGTAT GATGGAGCTG  6777
CAAATTTCAT GGCAGTTCAT GCAGTCGGTC AAGAGGAGGA TTTTGTTTTG TAGTTTGCAG  6837
ATGAGCATTT CTAAAGCATT TTCCCTTGCT GTATTTTTT GTATTATAAA TTACATTGGA  6897
CTTCATATAT ATAATTTTTT TTTACATTAT ATGTCTCTTG TATGTTTTGA AACTCTTGTA  6957
TTTATGATAT AGCTTATATG ATTTTTTTGC CTTGGTATAC ATTTTAAAAT ATGAATTTAA  7017
AAAATTTTTG TAAAAATAAA ATTCACAAAA TTGTTTTGAA AAACAAAAAA AAAAAAA    7075
```

(2) INFORMATION FOR SEQ ID NO:16:

(i) SEQUENCE CHARACTERISTICS:
        (A) LENGTH: 1205 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:16:

```
Met Asp Ala Lys Ala Arg Asn Cys Leu Leu Gln His Arg Glu Ala Leu
 1               5                  10                  15

Glu Lys Asp Ile Lys Thr Ser Tyr Ile Met Asp His Met Ile Ser Asp
                20                  25                  30

Gly Phe Leu Thr Ile Ser Glu Glu Lys Val Arg Asn Glu Pro Thr
            35                  40                  45

Gln Gln Gln Arg Ala Ala Met Leu Ile Lys Met Ile Leu Lys Lys Asp
        50                  55                  60

Asn Asp Ser Tyr Val Ser Phe Tyr Asn Ala Leu Leu His Glu Gly Tyr
65                  70                  75                  80

Lys Asp Leu Ala Ala Leu Leu His Asp Gly Ile Pro Val Val Ser Ser
                85                  90                  95

Ser Ser Gly Lys Asp Ser Val Ser Gly Ile Thr Ser Tyr Val Arg Thr
            100                 105                 110

Val Leu Cys Glu Gly Gly Val Pro Gln Arg Pro Val Val Phe Val Thr
        115                 120                 125

Arg Lys Lys Leu Val Asn Ala Ile Gln Gln Lys Leu Ser Lys Leu Lys
    130                 135                 140

Gly Glu Pro Gly Trp Val Thr Ile His Gly Met Ala Gly Cys Gly Lys
145                 150                 155                 160

Ser Val Leu Ala Ala Glu Ala Val Arg Asp His Ser Leu Leu Glu Gly
                165                 170                 175

Cys Phe Pro Gly Gly Val His Trp Val Ser Val Gly Lys Gln Asp Lys
            180                 185                 190

Ser Gly Leu Leu Met Lys Leu Gln Asn Leu Cys Thr Arg Leu Asp Gln
        195                 200                 205

Asp Glu Ser Phe Ser Gln Arg Leu Pro Leu Asn Ile Glu Glu Ala Lys
    210                 215                 220

Asp Arg Leu Arg Ile Leu Met Leu Arg Lys His Pro Arg Ser Leu Leu
225                 230                 235                 240

Ile Leu Asp Asp Val Trp Asp Ser Trp Val Leu Lys Ala Phe Asp Ser
                245                 250                 255

Gln Cys Gln Ile Leu Leu Thr Thr Arg Asp Lys Ser Val Thr Asp Ser
            260                 265                 270

Val Met Gly Pro Lys Tyr Val Val Pro Val Glu Ser Ser Leu Gly Lys
        275                 280                 285

Glu Lys Gly Leu Glu Ile Leu Ser Leu Phe Val Asn Met Lys Lys Ala
    290                 295                 300

Asp Leu Pro Glu Gln Ala His Ser Ile Ile Lys Glu Cys Lys Gly Ser
305                 310                 315                 320

Pro Leu Val Val Ser Leu Ile Gly Ala Leu Leu Arg Asp Phe Pro Asn
                325                 330                 335

Arg Trp Glu Tyr Tyr Leu Lys Gln Leu Gln Asn Lys Gln Phe Lys Arg
```

-continued

```
            340             345             350
Ile Arg Lys Ser Ser Ser Tyr Asp Tyr Glu Ala Leu Asp Glu Ala Met
        355             360             365
Ser Ile Ser Val Glu Met Leu Arg Glu Asp Ile Lys Asp Tyr Tyr Thr
    370             375             380
Asp Leu Ser Ile Leu Gln Lys Asp Val Lys Val Pro Thr Lys Val Leu
385             390             395             400
Cys Ile Leu Trp Asp Met Glu Thr Glu Val Glu Asp Ile Leu Gln
            405             410             415
Glu Phe Val Asn Lys Ser Leu Leu Phe Cys Asp Arg Asn Gly Lys Ser
            420             425             430
Phe Arg Tyr Tyr Leu His Asp Leu Gln Val Asp Phe Leu Thr Glu Lys
        435             440             445
Asn Cys Ser Gln Leu Gln Asp Leu His Lys Lys Ile Ile Thr Gln Phe
        450             455             460
Gln Arg Tyr His Gln Pro His Thr Leu Ser Pro Asp Gln Glu Asp Cys
465             470             475             480
Met Tyr Trp Tyr Asn Phe Leu Ala Tyr His Met Ala Ser Ala Lys Met
            485             490             495
His Lys Glu Leu Cys Ala Leu Met Phe Ser Leu Asp Trp Ile Lys Ala
            500             505             510
Lys Thr Glu Leu Val Gly Pro Ala His Leu Ile His Glu Phe Val Glu
        515             520             525
Tyr Arg His Ile Leu Asp Glu Lys Asp Cys Ala Val Ser Glu Asn Phe
        530             535             540
Gln Glu Phe Leu Ser Leu Asn Gly His Leu Leu Gly Arg Gln Pro Phe
545             550             555             560
Pro Asn Ile Val Gln Leu Gly Leu Cys Glu Pro Glu Thr Ser Glu Val
            565             570             575
Tyr Gln Gln Ala Lys Leu Gln Ala Lys Gln Glu Val Asp Asn Gly Met
            580             585             590
Leu Tyr Leu Glu Trp Ile Asn Lys Lys Asn Ile Thr Asn Leu Ser Arg
        595             600             605
Leu Val Val Arg Pro His Thr Asp Ala Val Tyr His Ala Cys Phe Ser
    610             615             620
Glu Asp Gly Gln Arg Ile Ala Ser Cys Gly Ala Asp Lys Thr Leu Gln
625             630             635             640
Val Phe Lys Ala Glu Thr Gly Glu Lys Leu Leu Glu Ile Lys Ala His
            645             650             655
Glu Asp Glu Val Leu Cys Cys Ala Phe Ser Thr Asp Arg Phe Ile
            660             665             670
Ala Thr Cys Ser Val Asp Lys Lys Val Lys Ile Trp Asn Ser Met Thr
        675             680             685
Gly Glu Leu Val His Thr Tyr Asp Glu His Ser Glu Gln Val Asn Cys
        690             695             700
Cys His Phe Thr Asn Ser Ser His Leu Leu Leu Ala Thr Gly Ser
705             710             715             720
Ser Asp Cys Phe Leu Lys Leu Trp Asp Leu Asn Gln Lys Glu Cys Arg
            725             730             735
Asn Thr Met Phe Gly His Thr Asn Ser Val Asn His Cys Arg Phe Ser
            740             745             750
Pro Asp Asp Lys Leu Leu Ala Ser Cys Ser Ala Asp Gly Thr Leu Lys
        755             760             765
```

-continued

```
Leu Trp Asp Ala Thr Ser Ala Asn Glu Arg Lys Ser Ile Asn Val Lys
770                 775                 780
Gln Phe Phe Leu Asn Leu Glu Asp Pro Gln Glu Asp Met Glu Val Ile
785                 790                 795                 800
Val Lys Cys Cys Ser Trp Ser Ala Asp Gly Ala Arg Ile Met Val Ala
            805                 810                 815
Ala Lys Asn Lys Ile Phe Leu Trp Asn Thr Asp Ser Arg Ser Lys Val
            820                 825                 830
Ala Asp Cys Arg Gly His Leu Ser Trp Val His Gly Val Met Phe Ser
            835                 840                 845
Pro Asp Gly Ser Ser Phe Leu Thr Ser Ser Asp Asp Gln Thr Ile Arg
            850                 855                 860
Leu Trp Glu Thr Lys Lys Val Cys Lys Asn Ser Ala Val Met Leu Lys
865                 870                 875                 880
Gln Glu Val Asp Val Val Phe Gln Gly Asn Glu Val Met Val Leu Ala
            885                 890                 895
Val Asp His Ile Arg Arg Leu Gln Leu Ile Asn Gly Arg Thr Gly Gln
            900                 905                 910
Ile Asp Tyr Leu Thr Glu Ala Gln Val Ser Cys Cys Cys Leu Ser Pro
            915                 920                 925
His Leu Gln Tyr Ile Ala Phe Gly Asp Glu Asn Gly Ala Ile Glu Ile
            930                 935                 940
Leu Glu Leu Val Asn Asn Arg Ile Phe Gln Ser Arg Phe Gln His Lys
945                 950                 955                 960
Lys Thr Val Trp His Ile Gln Phe Thr Ala Asp Glu Lys Thr Leu Ile
            965                 970                 975
Ser Ser Ser Asp Asp Ala Glu Ile Gln Val Trp Asn Trp Gln Leu Asp
            980                 985                 990
Lys Cys Ile Phe Leu Arg Gly His Gln Glu Thr Val Lys Asp Phe Arg
            995                 1000                1005
Leu Leu Lys Asn Ser Arg Leu Leu Ser Trp Ser Phe Asp Gly Thr Val
            1010                1015                1020
Lys Val Trp Asn Ile Ile Thr Gly Asn Lys Glu Lys Asp Phe Val Cys
1025                1030                1035                1040
His Gln Gly Thr Val Leu Ser Cys Asp Ile Ser His Asp Ala Thr Lys
            1045                1050                1055
Phe Ser Ser Thr Ser Ala Asp Lys Thr Ala Lys Ile Trp Ser Phe Asp
            1060                1065                1070
Leu Leu Leu Pro Leu His Glu Leu Arg Gly His Asn Gly Cys Val Arg
            1075                1080                1085
Cys Ser Ala Phe Ser Val Asp Ser Thr Leu Leu Ala Thr Gly Asp Asp
            1090                1095                1100
Asn Gly Glu Ile Arg Ile Trp Asn Val Ser Asn Gly Glu Leu Leu His
1105                1110                1115                1120
Leu Cys Ala Pro Leu Ser Glu Glu Gly Ala Ala Thr His Gly Gly Trp
            1125                1130                1135
Val Thr Asp Leu Cys Phe Ser Pro Asp Gly Lys Met Leu Ile Ser Ala
            1140                1145                1150
Gly Gly Tyr Ile Lys Trp Trp Asn Val Val Thr Gly Glu Ser Ser Gln
            1155                1160                1165
Thr Phe Tyr Thr Asn Gly Thr Asn Leu Lys Lys Ile His Val Ser Pro
            1170                1175                1180
```

```
-continued

Asp Phe Lys Thr Tyr Val Thr Val Asp Asn Leu Gly Ile Leu Tyr Ile
1185                1190                1195                1200

Leu Gln Thr Leu Glu
            1205
```